United States Patent
Sun

(10) Patent No.: US 11,510,895 B2
(45) Date of Patent: Nov. 29, 2022

(54) COMPOSITIONS AND FORMULATIONS INCLUDING CABAZITAXEL AND HUMAN SERUM ALBUMIN

(71) Applicant: Zhuhai Beihai Biotech Co., Ltd., Jinwan Zhuhai (CN)

(72) Inventor: Qun Sun, Princeton, NJ (US)

(73) Assignee: Zhuhai Beihai Biotech Co., Ltd., Zhuhai (CN)

( * ) Notice: Subject to any disclaimer, the term of this patent is extended or adjusted under 35 U.S.C. 154(b) by 70 days.

(21) Appl. No.: 16/886,415

(22) Filed: May 28, 2020

(65) Prior Publication Data

US 2020/0345681 A1    Nov. 5, 2020

Related U.S. Application Data

(63) Continuation of application No. 16/069,047, filed as application No. PCT/US2017/013194 on Jan. 12, 2017, now abandoned.

(60) Provisional application No. 62/420,986, filed on Nov. 11, 2016, provisional application No. 62/279,074, filed on Jan. 15, 2016.

(51) Int. Cl.
| | | |
|---|---|---|
| *A61K 31/337* | (2006.01) | |
| *A61K 9/00* | (2006.01) | |
| *A61K 9/19* | (2006.01) | |
| *A61K 38/38* | (2006.01) | |
| *A61P 35/00* | (2006.01) | |
| *A61K 47/42* | (2017.01) | |
| *A61K 9/08* | (2006.01) | |
| *C07D 305/14* | (2006.01) | |

(52) U.S. Cl.
CPC .......... *A61K 31/337* (2013.01); *A61K 9/0019* (2013.01); *A61K 9/08* (2013.01); *A61K 9/19* (2013.01); *A61K 38/385* (2013.01); *A61K 47/42* (2013.01); *A61P 35/00* (2018.01); *C07D 305/14* (2013.01)

(58) Field of Classification Search
CPC ...... A61K 38/385; A61K 9/19; A61K 31/337; A61K 9/0019; A61K 9/08; A61P 35/00
See application file for complete search history.

(56) References Cited

U.S. PATENT DOCUMENTS

| | | |
|---|---|---|
| 6,506,405 B1 | 1/2003 | Soon-Shiong et al. |
| 8,735,611 B2 | 5/2014 | Henschke et al. |
| 8,901,322 B2 | 12/2014 | Lahiri et al. |
| 9,012,665 B2 | 4/2015 | Kung et al. |
| 9,199,953 B2 | 12/2015 | Lahiri et al. |
| 9,309,210 B2 | 4/2016 | Didier et al. |
| 9,353,076 B2 | 5/2016 | Li et al. |
| 9,394,266 B2 | 7/2016 | Vraspir et al. |
| 2005/0282734 A1 | 12/2005 | Kadima et al. |
| 2012/0076862 A1 | 3/2012 | Desai et al. |
| 2015/0141673 A1 | 5/2015 | Song et al. |
| 2015/0315164 A1 | 11/2015 | Rampalli et al. |
| 2016/0000726 A1 | 1/2016 | Li et al. |
| 2016/0244420 A1 | 8/2016 | Cabri et al. |
| 2016/0257663 A1 | 9/2016 | Cabri et al. |
| 2016/0340327 A1 | 11/2016 | Rampalli et al. |
| 2019/0083448 A1 | 3/2019 | Sun |
| 2021/0052540 A1 | 2/2021 | Sun |

FOREIGN PATENT DOCUMENTS

| | | | |
|---|---|---|---|
| CN | 103393632 | 11/2013 | |
| CN | 104224750 | 12/2014 | |
| CN | 104490797 | 4/2015 | |
| CN | 105012251 | 11/2015 | |
| CN | 105012251 A | * 11/2015 | ............ A61K 47/42 |
| CN | 105727303 | 7/2016 | |
| CN | 106852911 | 6/2017 | |
| WO | WO 2014067207 | 5/2014 | |
| WO | WO 2014115168 | 7/2014 | |
| WO | WO 2014128728 | 8/2014 | |
| WO | WO 2015058960 | 4/2015 | |
| WO | WO 2015087228 | 6/2015 | |
| WO | WO 2018059304 | 4/2018 | |
| WO | WO 2017123760 | 1/2020 | |

OTHER PUBLICATIONS

English translation of CN-105012251-A made Apr. 2020. (Year: 2020).*
PCT International Preliminary Report on Patentability in International Appln. No. PCT/US2019/028337, dated Oct. 20, 2020, 7 pages.
PCT International Search Report and Written Opinion in International Appln. No. PCT/US2019/028337, dated Jun. 25, 2019, 9 pages.
Bosse et al., "Phase I comparability of recombinant human albumin and human serum albumin.", J. Clin. Pharmacol., 45: 57-67, 2005.
Briggs et al., "An adverse reaction to the administration of disoprofol", Anesthesia, 37, 1099, 1982.
Bruno et al., "Population pharmacokinetics/pharmacodynamics of docetaxel in phase II studies in patients with cancer.", J. Clin. Oncol., 16: 187-96, 1998.
Carter et al., "Structure of serum albumin.", Adv. Protein. Chem., 45, 153-203, 1994.
Chen et al., "Human serum albumin from recombinant DNA technology: challenges and strategies.", Biochim. Biophys. Acta., 1830: 5515-5525, 2013.

(Continued)

*Primary Examiner* — Michael B. Pallay
(74) *Attorney, Agent, or Firm* — Fish & Richardson P.C.

(57) ABSTRACT

This document relates to non-covalently bound complexes comprising cabazitaxel and human serum albumin. This document also relates to compositions comprising non-covalently bound complexes comprising cabazitaxel and human serum albumin. This document also relates to compositions comprising cabazitaxel and human serum albumin. This document also relates to compositions consisting essentially of cabazitaxel and human serum albumin.

8 Claims, No Drawings

(56) References Cited

OTHER PUBLICATIONS

Chen, "Removal of fatty acids from serum albumin by charcoal treatment.", J. Biol. Chem. 242: 173-181, 1967.
Cohn et al., "Preparation and properties of serum and plasma proteins; a system for the separation into fractions of the protein and lipoprotein components of biological tissues and fluids.", J. Am. Chem. Soc., 68: 459-475, 1946.
Curry et al., "Crystal structure of human serum albumin complexed with fatty acid reveals an asymmetric distribution of binding sites.", Nat. Struct. Biol., 5, 827-35, 1998.
Curry et al., "Fatty acid binding to human serum albumin: new insights from crystallographic studies", Biochemica et Biophysica Acta., 1441, 131-140, 1999.
Extended European Search Report in Application No. 17738932, dated Jan. 18, 2019.
Fehske et al., "The location of drug binding sites in human serum albumin.", Biochem. Pharmcol., 30, 687-92, 1981.
Finlayson, Seminars in Thrombosis and Hemostasis, 6, 85-120, 1980.
Hauser et al., "Oxygen transport responses to colloids and crystalloids in critically ill surgical patients.", Surgery, Gynecology and Obstetrics, 150, 811-816, 1980.
He et al., "Atomic structure and chemistry of human serum albumin.", Nature, 358, 209-15, 1992.
International Search Report and Written Opinion for App. Ser. No. PCT/US17/13194, dated Mar. 30, 2017, 11 pages.
Kragh-Hansen, "Structure- and ligand binding properties of human serum albumin", Dan. Med Bull., 1441, 131-40, 1990.
Lee et al. "An intravenous formulation decision tree for discovery compound formulation development.", International Journal of Pharmaceutics, 253, 111-119, 2003.
Lin et al., "Stability of human serum albumin during bioprocessing: denaturation and aggregation during processing of albumin paste.", Pharmaceutical Research 17: 391-6, 2000.
Piccart et al., "Docetaxel: an active new drug for treatment of advanced epithelial ovarian cancer.", J. Natl. Cancer Inst., 87: 676-81, 1995.
Sugio et al., "Crystal structure of human serum albumin at 2.5 A resolution.", Protein. Eng., 12, 439-46, 1999.
Trudeau et al., "Docetaxel in patients with metastatic breast cancer: a phase II study of the National Cancer Institute of Canada-Clinical Trials Group.", J. Clin. Oncol., 14: 422-8, 1996.
Tullis, "Albumin. 1. Background and use.", JAMA, 237, 355-360, 460-463, 1977.
Vorum, "Reversible ligand binding to human serum albumin. Theoretical and clinical aspects.", Dan. Med. Bull., 46, 379-99, 1999.
Waugh et al., "Stability, compatibility, and plasticizer extraction of taxol (NSC-125973) injection diluted in infusion solutions and stored in various containers.", Am. J. Hosp. Pharmacists, 48, 1520, 1991.

\* cited by examiner

COMPOSITIONS AND FORMULATIONS INCLUDING CABAZITAXEL AND HUMAN SERUM ALBUMIN

CLAIM OF PRIORITY

This application is a continuation of U.S. application Ser. No. 16/069,047, which is an U.S. National application from PCT/US2017/013194 filed on Jan. 12, 2017, which claims the benefit of U.S. provisional application No. 62/420,986 filed Nov. 11, 2016, and U.S. provisional application No. 62/279,074 filed Jan. 15, 2016. The entire contents of the foregoing are hereby incorporated by reference.

TECHNICAL FIELD

This document relates to complexes and compositions for the treatment of proliferative diseases.

BACKGROUND

Many drugs for parenteral use are insoluble in water, and are thus formulated with solubilizing agents, surfactants, solvents, and/or emulsifiers that are irritating, allergenic, or toxic when administered to patients. See, e.g., Briggs et al., *Anesthesis* 37, 1099 (1982), and Waugh et al., *Am. J. Hosp. Pharmacists*, 48, 1520 (1991)). Further, many of these drugs, especially those administered intravenously, cause undesirable side effects such as venous irritation, phlebitis, burning and pain on injection, venous thrombosis, extravasation, and other administration related side effects. Additionally, often free drugs present in formulations induce pain or irritation upon administration.

Taxanes play an important role in the treatment of various solid tumors. Cabazitaxel (trade name Jevtana®) is a semi-synthetic taxane derivative. It was developed by Sanofi-Aventis and was approved by the U.S. FDA for the treatment of hormone-refractory prostate cancer on Jun. 17, 2010. Cabazitaxel in combination with prednisone is a treatment option for hormone-refractory prostate cancer following cabazitaxel-based treatment. JEVTANA is supplied as a kit consisting of (a) a JEVTANA injection, which contains 60 mg cabazitaxel in 1.5 mL polysorbate 80; and (b) a diluent, containing approximately 5.7 mL 13% (W/W) ethanol. Prior to administration, the JEVTANA injection must first be mixed with the diluent, which dilutes the amount of Cabazitaxel to 10 mg/mL, and then further diluted with either 0.9% sodium chloride solution or 5% dextrose solution for infusion. See JEVTANA Prescribing Information.

Other taxane compounds include cabazitaxel, which is marketed as Taxotere® and is FDA-approved for breast cancer, non-small cell lung cancer, hormone refractory prostate cancer, gastric adenocarcinoma, and squamous cell carcinoma of head and neck cancer. The clinical intravenous administration of commercially available cabazitaxel (Taxotere®) is formulated in a highly concentrated solution containing 40 mg cabazitaxel and 1040 mg Polysorbate 80 per mL. See TAXOTERE Prescribing Information.

The presence of polysorbate 80 in JEVTANA, as well as TAXOTERE, can result in serious side effects. It has been reported that cabazitaxel administration is associated with the occurrence of unpredictable (acute) hypersensitivity reactions and cumulative fluid retention. See, e.g., Trudeau M E et al., *J Clin Oncol* 1996; 14:422-8, Piccart M J et al., *J Natl Cancer Inst* 1995; 87:676-81, Bruno R et al., *J Clin Oncol* 1998; 16:187-96. These side-effects have been attributed, in part, to the presence of polysorbate 80.

In order to reduce the side effects induced by polysorbate 80, patients may be treated with dexamethasone prior to each dose of JEVTANA. Dexamethasone is a steroid that suppresses the immune response in patients, which can be especially detrimental in cancer patients under chemotherapy, whose immunity may already be compromised due to the destruction of healthy cells by the chemotherapeutic treatment. As a result, these patients can be susceptible to bacterial and fungal infections. Further, despite receiving the dexamethasone pre-medication, patients can report hypersensitivity side effects from the taxane compound treatment. Due to these side effects, patients may stop taxane compound therapy, skip a dose, or continue further therapy at a reduced dose.

Therefore, new formulations of cabazitaxel or other taxane compounds are needed to avoid these side effects, pre-medication requirements, and patient noncompliance issues associated with the currently marketed formulation.

SUMMARY

Provided herein are non-covalently bound complexes comprising cabazitaxel and human serum albumin, e.g., non-covalently bound complexes prepared by a process of contacting (e.g., mixing, e.g., in a solution such as an aqueous solution) cabazitaxel and human serum albumin, wherein the cabazitaxel and the human serum albumin used to prepare the non-covalently bound complexes are in a ratio by weight from about 1:10 to about 1:3000.

In some embodiments, the human serum albumin is a native human serum albumin. In some embodiments, the human serum albumin is a recombinant human serum albumin. In some embodiments, the human serum albumin is a fatty acid free human serum albumin. In some embodiments, the human serum albumin is essentially fatty acid free.

Also, provided herein is a composition comprising non-covalently bound complexes comprising cabazitaxel and human serum albumin, wherein the cabazitaxel and the human serum albumin in the composition have a ratio by weight from about 1:10 to about 1:3000. In some embodiments, the pH of the composition is neutral (e.g., pH of the composition is from about 5 to about 8, from about 5.5 to about 7.5, or from about 6 to about 7, or the pH of the composition is about 5, about 5.5, about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8). In some embodiments, the human serum albumin is essentially fatty acid free.

In some embodiments, the composition is a solid formulation. For example, the solid formulation can be produced in a uniform manner by lyophilization. A skilled artisan would recognize other methods, such as rotary evaporation, that can also produce solid formulations.

In some embodiments, the composition is an aqueous formulation. In some embodiments, the aqueous formulation is substantially free of solvent other than water. In some embodiments, the aqueous formulation is free of solvent other than water. In some embodiments, the aqueous formulation includes water and water-miscible organic solvents including at least one of polyethylene glycol 300, polyethylene glycol 400, ethanol, methanol, propylene glycol, glycerin, N-methyl-2-pyrrolidone, dimethylacetamide, and dimethylsulfoxide. For example, the water-miscible organic solvent can include ethanol. In some embodiments, the aqueous formulation includes water and ethanol. In some embodiments, the water-miscible organic solvent can be a mixture of water-miscible organic solvents.

In some embodiments, the aqueous formulation is a clear aqueous solution. In some embodiments, the aqueous formulation is a clear aqueous solution for at least 6 hours. For example, the formulation can be a clear and stable aqueous solution reconstituted from a sterile lyophilized powder. In some embodiments, the aqueous formulation is a clear aqueous solution, wherein the aqueous formulation is substantially free of solvent other than water. In some embodiments, the aqueous formulation is a clear aqueous solution, wherein the aqueous formulation is free of solvent other than water.

Also, provided herein is a pharmaceutical composition comprising the non-covalently bound complexes or the composition comprising the non-covalently bound complexes of the cabazitaxel and the human serum albumin as described herein, and a pharmaceutically acceptable carrier.

Also, provided herein is a method of treating a cancer, the method comprising the step of administering to a subject in need thereof of a therapeutically effective amount of a pharmaceutical composition comprising non-covalently bound complexes or the composition comprising the cabazitaxel and the human serum albumin as described herein, and a pharmaceutically acceptable carrier.

In some embodiments, the cancer is a solid tumor cancer. In some embodiments, the cancer is a prostate cancer.

In some embodiments, the method of treating a prostate cancer comprises the step of administering to a subject in need thereof of a therapeutically effective amount of a pharmaceutical composition comprising non-covalently bound complexes or the composition comprising the cabazitaxel and the human serum albumin as described herein, prednisone, and a pharmaceutically acceptable carrier.

Also, provided herein is a composition comprising cabazitaxel and human serum albumin, wherein the cabazitaxel and the human serum albumin in the composition have a ratio by weight from about 1:10 to about 1:3000, wherein the composition is a clear aqueous solution when the composition is dissolved in an aqueous solvent, and wherein the composition has a solubility in an aqueous solution of at least 10 mg/mL. In some embodiments, the pH of the composition is neutral (e.g., pH of the composition is from about 5 to about 8, from about 5.5 to about 7.5, or from about 6 to about 7, or the pH of the composition is about 5, about 5.5, about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8).

In some embodiments, the human serum albumin is a native human serum albumin. In some embodiments, the human serum albumin is a recombinant human serum albumin. In some embodiments, the human serum albumin is a fatty acid free human serum albumin. In some embodiments, the human serum albumin is essentially fatty acid free.

In some embodiments, the composition is a clear aqueous solution for at least 6 hours when the composition is dissolved in an aqueous solvent. In some embodiments, the composition is a clear aqueous solution for at least 24 hours when the composition is dissolved in an aqueous solvent. In some embodiments, the composition is a clear aqueous solution for at least 3 days when the composition is dissolved in an aqueous solvent. In some embodiments, the aqueous solution is substantially free of solvent other than water. In some embodiments, the aqueous solution is free of solvent other than water.

In some embodiments, the composition is a solid formulation. For example, the solid formulation can be produced in a uniform manner by lyophilization. A skilled artisan would recognize other methods, such as rotary evaporation, that can also produce solid formulations.

In some embodiments, the composition is an aqueous formulation. In some embodiments, the aqueous formulation is substantially free of solvent other than water. In some embodiments, the aqueous formulation is free of solvent other than water.

In some embodiments, the aqueous formulation can be free of a surfactant, such as CREMOPHOR® surfactants and Polysorbate 80. In some embodiments, the aqueous formulation can be substantially free of a surfactant, such as CREMOPHOR® surfactants and Polysorbate 80.

In some embodiments, the aqueous formulation is a clear aqueous solution. For example, the formulation can be a clear and stable aqueous solution reconstituted from a sterile lyophilized powder. In some embodiments, the aqueous formulation is a clear aqueous solution, wherein the aqueous formulation is substantially free of solvent other than water. In some embodiments, the aqueous formulation is a clear aqueous solution, wherein the aqueous formulation is free of solvent other than water.

Also, provided herein is a pharmaceutical composition comprising the composition comprising the cabazitaxel and the human serum albumin as described herein, and a pharmaceutically acceptable carrier.

Also, provided herein is a method of treating a cancer, the method comprising the step of administering to a subject in need thereof of a therapeutically effective amount of a pharmaceutical composition comprising the composition comprising the cabazitaxel and the human serum albumin as described herein, and a pharmaceutically acceptable carrier.

In some embodiments, the cancer is a solid tumor cancer. In some embodiments, the cancer is a prostate cancer.

In some embodiments, the method of treating a prostate cancer comprises the step of administering to a subject in need thereof of a therapeutically effective amount of a pharmaceutical composition comprising the composition comprising the cabazitaxel and the human serum albumin as described herein, prednisone, and a pharmaceutically acceptable carrier.

Also, provided herein is a composition consisting essentially of cabazitaxel and human serum albumin, wherein the cabazitaxel and the human serum albumin in the composition have a ratio by weight from about 1:10 to about 1:3000. In some embodiments, the pH of the composition is neutral (e.g., pH of the composition is from about 5 to about 8, from about 5.5 to about 7.5, or from about 6 to about 7, or the pH of the composition is about 5, about 5.5, about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8).

In some embodiments, the human serum albumin is a native human serum albumin. In some embodiments, the human serum albumin is a recombinant human serum albumin. In some embodiments, the human serum albumin is a fatty acid free human serum albumin. In some embodiments, the human serum albumin is essentially fatty acid free.

In some embodiments, the composition is a clear aqueous solution when the composition is dissolved in an aqueous solvent. In some embodiments, the aqueous solution is substantially free of solvent other than water.

In some embodiments, the composition is a clear aqueous solution for at least 6 hours when the composition is dissolved in an aqueous solvent. In some embodiments, the composition is a clear aqueous solution for at least 24 hours when the composition is dissolved in an aqueous solvent. In some embodiments, the composition is a clear aqueous solution for at least 3 days when the composition is dissolved in an aqueous solvent. In some embodiments, the aqueous solution is substantially free of solvent other than water.

In some embodiments, the composition is a solid formulation. In some embodiments, the composition is an aqueous formulation. In some embodiments, the aqueous formulation is substantially free of solvent other than water. In some embodiments, the aqueous formulation is free of a surfactant, such as CREMOPHOR® surfactants and Polysorbate 80. In some embodiments, the aqueous formulation is a clear aqueous solution.

Also, provided herein is a pharmaceutical composition comprising the composition consisting essentially of the cabazitaxel and the human serum albumin as described herein, and a pharmaceutically acceptable carrier.

Also, provided herein is a method of treating cancer comprising the step of administering to a subject in need thereof a therapeutically effective amount of a pharmaceutical composition comprising the composition consisting essentially of the cabazitaxel and the human serum albumin as described herein, and a pharmaceutically acceptable carrier.

In some embodiments, the cancer is a solid tumor cancer. In some embodiments, the cancer is a prostate cancer.

In some embodiments, the method of treating a prostate cancer comprises the step of administering to a subject in need thereof of a therapeutically effective amount of a pharmaceutical composition comprising the composition consisting essentially of the cabazitaxel and the human serum albumin as described herein, prednisone, and a pharmaceutically acceptable carrier.

Also, provided herein is a composition comprising cabazitaxel and human serum albumin, wherein the cabazitaxel and the human serum albumin in the composition have a ratio by weight from about 1:100 to about 1:3000. In some embodiments, the pH of the composition is neutral (e.g., pH of the composition is from about 5 to about 8, from about 5.5 to about 7.5, or from about 6 to about 7, or the pH of the composition is about 5, about 5.5, about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8).

In some embodiments, the human serum albumin is a native human serum albumin. In some embodiments, the human serum albumin is a recombinant human serum albumin. In some embodiments, the human serum albumin is essentially fatty acid free.

In some embodiments, the composition is a clear aqueous solution when the composition is dissolved in an aqueous solvent. In some embodiments, the aqueous solution is substantially free of solvent other than water.

In some embodiments, the composition is a clear aqueous solution for at least 3 hours when the composition is dissolved in an aqueous solvent. In some embodiments, the composition is a clear aqueous solution for at least 6 hours when the composition is dissolved in an aqueous solvent. In some embodiments, the composition is a clear aqueous solution for at least 24 hours when the composition is dissolved in an aqueous solvent. In some embodiments, the composition is a clear aqueous solution for at least 3 days when the composition is dissolved in an aqueous solvent. In some embodiments, the aqueous solution is substantially free of solvent other than water.

In some embodiments, the composition is a solid formulation. In some embodiments, the composition is an aqueous formulation. In some embodiments, the aqueous formulation is substantially free of solvent other than water. In some embodiments, the aqueous formulation is free of a surfactant, such as CREMOPHOR® surfactants and Polysorbate 80. In some embodiments, the aqueous formulation is a clear aqueous solution.

Also, provided herein is a pharmaceutical composition comprising the composition comprising the cabazitaxel and the human serum albumin as described herein, and a pharmaceutically acceptable carrier.

Also, provided herein is a method of treating cancer comprising the step of administering to a subject in need thereof a therapeutically effective amount of a pharmaceutical composition comprising the composition comprising the cabazitaxel and the human serum albumin as described herein, and a pharmaceutically acceptable carrier.

In some embodiments, the cancer is a solid tumor cancer. In some embodiments, the cancer is a prostate cancer.

In some embodiments, the method of treating a prostate cancer comprises the step of administering to a subject in need thereof of a therapeutically effective amount of a pharmaceutical composition comprising the composition comprising the cabazitaxel and the human serum albumin as described herein, prednisone, and a pharmaceutically acceptable carrier.

Also, provided herein is a composition consisting essentially of human serum albumin and non-covalently bound complexes of cabazitaxel and human serum albumin, wherein the cabazitaxel and the human serum albumin in the composition have a ratio by weight from about 1:10 to about 1:3000.

Also, provided herein is a composition comprising non-covalently bound complexes consisting essentially of cabazitaxel and human serum albumin, wherein the cabazitaxel and the human serum albumin in the composition have a ratio by weight from about 1:10 to about 1:3000.

DETAILED DESCRIPTION

Provided herein are non-covalently bound complexes comprising cabazitaxel and human serum albumin, e.g., non-covalently bound complexes prepared by a process of contacting (e.g., mixing, e.g., in a solution such as an aqueous solution) cabazitaxel and human serum albumin, wherein the cabazitaxel and the human serum albumin used to prepare the non-covalently bound complexes are in a ratio by weight from about 1:10 to about 1:3000.

Also, provided herein is a composition comprising a non-covalently bound complex comprising cabazitaxel and human serum albumin, wherein the cabazitaxel and the human serum albumin in the composition have a ratio by weight from about 1:10 to about 1:3000.

Also, provided herein is a composition comprising a non-covalently bound complex comprising cabazitaxel and human serum albumin, wherein the cabazitaxel and the human serum albumin in the complex have a ratio by weight from about 1:10 to about 1:3000.

In some embodiments, the cabazitaxel and the human serum albumin in the composition have a ratio by weight from about 1:100 to about 1:2000. In some embodiments, the cabazitaxel and the human serum albumin in the composition have a ratio by weight from about 1:150 to about 1:1000. In some embodiments, the cabazitaxel and the human serum albumin in the composition have a ratio by weight from about 1:150 to about 1:800. In some embodiments, the cabazitaxel and the human serum albumin in the composition have a ratio by weight from about 1:150 to about 1:600. In some embodiments, the cabazitaxel and the human serum albumin in the composition have a ratio by weight from about 1:150 to about 1:500. In some embodiments, the cabazitaxel and the human serum albumin in the composition have a ratio by weight from about 1:150 to about 1:400. In some embodiments, the cabazitaxel and the human serum albumin in the composition have a ratio by weight from about 1:200 to about 1:1000. In some embodiments, the cabazitaxel and the human serum albumin in the composition have a ratio by weight from about 1:200 to about 1:800. In some embodiments, the cabazitaxel and the human serum albumin in the composition have a ratio by weight from about 1:200 to about 1:600. In some embodiments, the cabazitaxel and the human serum albumin in the composition have a ratio by weight from about 1:200 to about 1:500. In some embodiments, the cabazitaxel and the human serum albumin in the composition have a ratio by weight from about 1:200 to about 1:400. In some embodiments, the cabazitaxel and the human serum albumin in the composition have a ratio by weight from about 1:250 to about 1:1000. In some embodiments, the cabazitaxel and the human serum albumin in the composition have a ratio by weight from about 1:250 to about 1:800. In some embodiments, the cabazitaxel and the human serum albumin in the composition have a ratio by weight from about 1:250 to about 1:600. In some embodiments, the cabazitaxel and the human serum albumin in the composition have a ratio by weight from about 1:250 to about 1:500. In some embodiments, the cabazitaxel and the human serum albumin in the composition have a ratio by weight from about 1:250 to about 1:400. In some embodiments, the cabazitaxel and the human serum albumin in the composition have a ratio by weight from about 1:300 to about 1:600. In some embodiments, the cabazitaxel and the human serum albumin in the composition have a ratio by weight from about 1:300 to about 1:400. In some embodiments, the cabazitaxel and the human serum albumin in the composition have a ratio by weight from about 1:100 to about 1:1000. In some embodiments, the cabazitaxel and the human serum albumin in the composition have a ratio by weight from about 1:220 to about 1:600. In some embodiments, the cabazitaxel and the human serum albumin in the composition have a ratio by weight of about 1:200, 1:210, 1:220, about 1:230, about 1:240, about 1:250, about 1:260, about 1:270, about 1:280, about 1:290, about 1:300, about 1:310, about 1:320, about 1:330, about 1:340, about 1:350, about 1:360, about 1:370, about 1:380, about 1:390, about 1:400, about 1:450, about 1:460, about 1:500 or about 1:600.

In some embodiments, the non-covalent interaction between cabazitaxel and human serum albumin in the complex comprises hydrogen bonding. In some embodiments, the non-covalent interaction between cabazitaxel and human serum albumin in the complex comprises electrostatic interaction. In some embodiments, the non-covalent interaction between cabazitaxel and human serum albumin in the complex comprises hydrophobic interaction. In some embodiments, the non-covalent interaction between cabazitaxel and human serum albumin in the complex comprises Van der Waals forces. In some embodiments, the non-covalent interaction between cabazitaxel and human serum albumin in the complex comprises hydrogen bonding, electrostatic interaction, hydrophobic interactions and Van der Waals forces.

In some embodiments, the non-covalent interaction between cabazitaxel and human serum albumin in the composition comprises hydrogen bonding. In some embodiments, the non-covalent interaction between cabazitaxel and human serum albumin in the composition comprises electrostatic interaction. In some embodiments, the non-covalent interaction between cabazitaxel and human serum albumin in the composition comprises hydrophobic interaction. In some embodiments, the non-covalent interaction between cabazitaxel and human serum albumin in the composition comprises Van der Waals forces. In some embodiments, the non-covalent interaction between cabazitaxel and human serum albumin in the composition comprises hydrogen bonding, electrostatic interaction, hydrophobic interactions and Van der Waals forces.

As used herein, the term "human serum albumin" refers to native and recombinant human serum albumin. Native human serum albumin and other plasma proteins can be precipitated from human plasma by varying the pH and adding ethanol, in what is known as the Cohn fractionation process (Cohn E J et al., *J. Am. Chem. Soc.* 1946; 68:459-475). By controlling the pH and ethanol content, semi-purified fractions of plasma proteins can be produced. One of the last proteins to precipitate in the Cohn process is native human serum albumin. After precipitation, a wet paste of crude native human serum albumin is obtained. Subsequent bioprocessing steps (purification, filtration, pasteurization, etc.) can be used to produce a purified, stabilized form of native human serum albumin for commercial use (Lin J J et al., *Pharmaceutical Research* 2000; 17:391-6). Recombinant human serum albumin is a highly purified animal-, virus-, and prion-free product as alternative to native human serum albumin, to which it is structurally equivalent (Bosse D et al., *J. Clin. Pharmacol.* 2005; 45:57-67). Recombinant human serum albumin has been produced by various hosts, both prokaryotic and eukaryotic (Chen Z et al., *Biochimica et Biophysica Acta* 2013; 1830:5515-5525). A fatty acid free human serum albumin can be prepared by treatment of human serum albumin with charcoal at low pH. Likewise, treatment of human serum albumin with charcoal at low pH can be used to remove fatty acids from human serum albumin (Chen R F, *J. Biol. Chem.* 1967; 242:173-181).

Human serum albumin (HSA) is a highly soluble globular protein of $M_r$ 65K and consists of 585 amino acids. HSA is the most abundant protein in the plasma and accounts for 70-80% of the colloid osmotic pressure of human plasma. The amino acid sequence of HSA contains a total of 17 disulphide bridges, one free thiol (Cys 34), and a single tryptophan (Trp 214). Intravenous use of HSA solution has been indicated for the prevention and treatment of hypovolumic shock (see, e.g., Tullis, *JAMA*, 237, 355-360, 460-463, (1977)) and Houser et al., *Surgery, Gynecology and Obstetrics*, 150, 811-816 (1980)) and in conjunction with exchange transfusion in the treatment of neonatal hyperbilirubinemia (see, e.g., Finlayson, *Seminars in Thrombosis and Hemostasis*, 6, 85-120, (1980)).

Human serum albumin (HSA) has multiple hydrophobic binding sites (a total of seven for medium and long-chain fatty acids, an endogenous ligand of HSA) and binds a diverse set of drugs, especially neutral and negatively charged hydrophobic compounds (Goodman et al., *The Pharmacological Basis of Therapeutics*, 9th ed, McGraw-Hill New York (1996)). Two high affinity binding sites have been proposed in subdomains IIA and IIIA of HSA, which are highly elongated hydrophobic pockets with charged lysine and arginine residues near the surface which function as attachment points for polar ligand features (see, e.g., Fehske et al., *Biochem. Pharmcol.*, 30, 687-92 (1981), Vorum, *Dan. Med. Bull.*, 46, 379-99 (1999), Kragh-Hansen, *Dan. Med Bull.*, 1441, 131-40 (1990), Curry et al., *Nat. Struct. Biol.*, 5, 827-35 (1998), Sugio et al., *Protein. Eng.*, 12, 439-46 (1999), He et al., *Nature,* 358, 209-15 (1992), and Carter et al., *Adv. Protein. Chem.,* 45, 153-203 (1994)).

In some embodiments, the human serum albumin is a native human serum albumin. In some embodiments, the human serum albumin is a recombinant human serum albumin. In some embodiments, the human serum albumin is a fatty acid free human serum albumin. In some embodiments, the human serum albumin is essentially fatty acid free. In some embodiments, the human serum albumin contains no more than two moles of fatty acids bound to one mole of human serum albumin. In some embodiments, the human serum albumin contains no more than one mole of fatty acids bound to one mole of human serum albumin. In some embodiments, human serum albumin contains no more than 0.5 moles of fatty acids bound to one mole of human serum albumin. In some embodiments, the human serum albumin contains no more than 0.1 moles of fatty acids bound to one mole of human serum albumin. In some embodiments, the human serum albumin contains no more than 0.05 moles of fatty acids bound to one mole of human serum albumin. In some embodiments, the human serum albumin contains no more than 0.01 moles of fatty acids bound to one mole of human serum albumin. In some embodiments, the human serum albumin contains no more than 0.001 moles of fatty acids bound to one mole of human serum albumin. In some embodiments, the human serum albumin contains no more than 0.0005 moles of fatty acids bound to one mole of human serum albumin. In some embodiments, the human serum albumin contains no more than 0.0001 moles of fatty acids bound to one mole of human serum albumin.

As used herein, the term "non-covalently bound complex" refers to a complex in which the bonds between the components of the complex are non-covalent bonds (e.g., weak bonds such as hydrogen bonds, electrostatic effects, π-effects, hydrophobic effects and Van der Waals forces). Further, human serum albumin (HSA) has multiple hydrophobic binding sites (a total of seven for medium and long-chain fatty acids, an endogenous ligand of HSA) and binds a diverse set of drugs, especially neutral and negatively charged hydrophobic compounds (Goodman et al., The Pharmacological Basis of Therapeutics, 9th ed, McGraw-Hill New York (1996)). Additionally, after the drug molecule binds to HSA, the drug molecule and HSA form a non-covalently bound drug and protein complex through the binding sites of HSA. This concept is commonly understood by one of ordinary skill in the art to which this disclosure belongs. One example of a non-covalently bound complex is a non-covalently bound complex of HSA and fatty acids, in which the fatty acids bind to HSA through HSA's multiple binding sites.

As used herein, the term "stable" refers to non-covalently bound complexes that do not readily disassociate and aggregate into their separate parts, e.g., do not readily dissociate and aggregate for a period of time of greater than 6 hours, 12 hours, 24 hours, or 3 days). For example, a solution including stable non-covalently bound complexes will often appear transparent whereas a solution including unstable non-covalently bound complexes will appear translucent or cloudy. Further, it will be appreciated by those of ordinary skill in the art, that after a period of time, stable non-covalently bound complexes can disassociate and aggregate into their separate parts. Thus, a solution including stable non-covalently bound complexes can become translucent or cloudy after a period of time (e.g., 6 hours, 12 hours, 24 hours, or 3 days).

In vitro, the binding of cabazitaxel to human serum proteins was 89 to 92% and was not saturable up to 50,000 ng/mL, which covers the maximum concentration observed in clinical trials. Cabazitaxel is mainly bound to human serum albumin (82%). See JEVTANA Prescribing Information.

As used herein, the term "essentially fatty acid free" refers to proteins (e.g. serum albumin) that contain less than about 0.02% fatty acid by weight. For example, human serum albumin that is essentially fatty acid free can contain less than 0.02% fatty acid by weight.

As used herein, the term "fatty acids" refers to non-esterified fatty acids (e.g. linoleic acid, α-linoleic acid, γ-linoleic acid).

As used herein the term cabazitaxel is a compound that has the CAS No. 183133-96-2 and the following chemical structure:

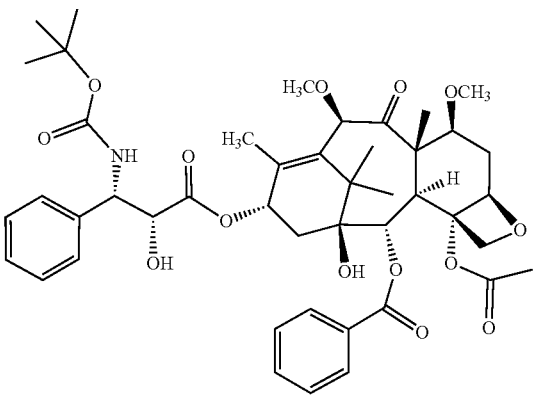

Cabazitaxel is lipophilic, practically insoluble in water and soluble in alcohol.

Further, cabazitaxel is a microtubule inhibitor indicated in combination with prednisone for treatment of patients with hormone-refractory metastatic prostate cancer previously treated with a cabazitaxel-containing treatment regimen.

In some embodiments, the cabazitaxel can be a pharmaceutically acceptable salt of cabazitaxel.

As used herein, the term "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free acid or free base form with a suitable base or acid, respectively. In some embodiments, pharmaceutically acceptable salts may be preferred over the respective free base or free acid because such salts impart greater stability or solubility to the molecule thereby facilitating formulation into a dosage form. Basic compounds are generally capable of forming pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), napthalene-2-sulfonate, ethanedisulfonate, hydrogen bisulfide, bitartrate, gluconate, glucuronate, para-bromophenylsulfonate, carbonate, pyrosulfate, sulfite, bisulfate, monohydrogen phosphate, dihydrogen phosphate, metaphosphate, pyrophosphate, chloride, bromide, iodide, decanoate, caprylate, caprate, propiolate, suberate, sebacate, butyne-1,4-dioate, hexyne-1,6-dioate, terephthalate, sulfonate, xylenesulfonate, phenylpropionate, phenylbutyrate, β-hydroxybutyrate, glycolate, propanesulfonate, naphthalene-1-sulfonate, naphthalene-2-sulfonate and 2,5-dihydroxybenzoate. Suitable bases include pharmaceutically acceptable inorganic bases and pharmaceutically acceptable organic bases. Representative pharmaceutically acceptable base addition salts include hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

In some embodiments, the cabazitaxel can be a cabazitaxel with one equivalent of the acetone solvate. In some embodiments, cabazitaxel, or a salt thereof, may be crystalline or amorphous. In some embodiments, cabazitaxel, or a salt thereof, may be in a form of a hydrate. In some embodiments, the cabazitaxel can be any one of cabazitaxel solvates, hydrates, and/or crystal forms disclosed, for example, in US application publication No. 20150315164, US application publication No. 20160257663, US application publication No. 20160340327, US application publication No. 20160244420, US application publication No. 20150141673, U.S. Pat. Nos. 9,012,665, 9,353,076, 9,394,266, 9,309,210, 9,199,953, 8,735,611, 8,735,611, 8,901,322, PCT publication No. WO2014115168, PCT publication No. WO2015087228, PCT publication No. WO2014067207, PCT publication No. WO2014128728 or PCT publication No. WO2015058960, the disclosures of each of the above are incorporated herein by reference in their entirety.

Also, provided herein is a composition comprising a non-covalently bound complex comprising cabazitaxel and human serum albumin, wherein the cabazitaxel and the human serum albumin in the composition have a ratio by weight from about 1:10 to about 1:3000. In some embodiments, the pH of the composition is neutral (e.g., pH of the composition is from about 5 to about 8, from about 5.5 to about 7.5, or from about 6 to about 7, or the pH of the composition is about 5, about 5.5, about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8).

In some embodiments, the cabazitaxel and the human serum albumin in the composition have a ratio by weight from about 1:100 to about 1:2000. In some embodiments, the cabazitaxel and the human serum albumin in the composition have a ratio by weight from about 1:150 to about 1:1000. In some embodiments, the cabazitaxel and the human serum albumin in the composition have a ratio by weight from about 1:150 to about 1:800. In some embodiments, the cabazitaxel and the human serum albumin in the composition have a ratio by weight from about 1:150 to about 1:600. In some embodiments, the cabazitaxel and the human serum albumin in the composition have a ratio by weight from about 1:150 to about 1:500. In some embodiments, the cabazitaxel and the human serum albumin in the composition have a ratio by weight from about 1:150 to about 1:400. In some embodiments, the cabazitaxel and the human serum albumin in the composition have a ratio by weight from about 1:200 to about 1:1000. In some embodiments, the cabazitaxel and the human serum albumin in the composition have a ratio by weight from about 1:200 to about 1:800. In some embodiments, the cabazitaxel and the human serum albumin in the composition have a ratio by weight from about 1:200 to about 1:600. In some embodiments, the cabazitaxel and the human serum albumin in the composition have a ratio by weight from about 1:200 to about 1:500. In some embodiments, the cabazitaxel and the human serum albumin in the composition have a ratio by weight from about 1:200 to about 1:400. In some embodiments, the cabazitaxel and the human serum albumin in the composition have a ratio by weight from about 1:250 to about 1:1000. In some embodiments, the cabazitaxel and the human serum albumin in the composition have a ratio by weight from about 1:250 to about 1:800. In some embodiments, the cabazitaxel and the human serum albumin in the composition have a ratio by weight from about 1:250 to about 1:600. In some embodiments, the cabazitaxel and the human serum albumin in the composition have a ratio by weight from about 1:250 to about 1:500. In some embodiments, the cabazitaxel and the human serum albumin in the composition have a ratio by weight from about 1:250 to about 1:400. In some embodiments, the cabazitaxel and the human serum albumin in the composition have a ratio by weight from about 1:300 to about 1:600. In some embodiments, the cabazitaxel and the human serum albumin in the composition have a ratio by weight from about 1:300 to about 1:400. In some embodiments, the cabazitaxel and the human serum albumin in the composition have a ratio by weight from about 1:100 to about 1:1000. In some embodiments, the cabazitaxel and the human serum albumin in the composition have a ratio by weight from about 1:220 to about 1:600. In some embodiments, the cabazitaxel and the human serum albumin in the composition have a ratio by weight of about 1:200, 1:210, 1:220, about 1:230, about 1:240, about 1:250, about 1:260, about 1:270, about 1:280, about 1:290, about 1:300, about 1:310, about 1:320, about 1:330, about 1:340, about 1:350, about 1:360, about 1:370, about 1:380, about 1:390, about 1:400, about 1:450, about 1:460, about 1:500 or about 1:600.

In some embodiments, the human serum albumin is a native human serum albumin. In some embodiments, the human serum albumin is a recombinant human serum albumin. In some embodiments, the human serum albumin is a fatty acid free human serum albumin. In some embodiments, the human serum albumin is essentially fatty acid free. In some embodiments, the human serum albumin contains no more than two moles of fatty acids bound to one mole of human serum albumin. In some embodiments, the human serum albumin contains no more than one mole of fatty acids bound to one mole of human serum albumin. In some embodiments, human serum albumin contains no more than 0.5 moles of fatty acids bound to one mole of human serum albumin. In some embodiments, the human serum albumin contains no more than 0.1 moles of fatty acids bound to one mole of human serum albumin. In some embodiments, the human serum albumin contains no more than 0.05 moles of fatty acids bound to one mole of human serum albumin. In some embodiments, the human serum albumin contains no more than 0.01 moles of fatty acids bound to one mole of human serum albumin. In some embodiments, the human serum albumin contains no more than 0.001 moles of fatty acids bound to one mole of human serum albumin. In some embodiments, the human serum albumin contains no more than 0.0005 moles of fatty acids bound to one mole of human serum albumin. In some embodiments, the human serum albumin contains no more than 0.0001 moles of fatty acids bound to one mole of human serum albumin.

In some embodiments, the cabazitaxel can be a pharmaceutically acceptable salt of cabazitaxel. In some embodiments, cabazitaxel can be any one of crystal forms, amorphous forms, solvates and hydrates as described herein.

In some embodiments, the composition is a clear aqueous solution when the composition is dissolved in an aqueous solution. In some embodiments, the aqueous solution is substantially free of solvent other than water. In some embodiments, the aqueous solution is free of solvent other than water.

As used herein, the term "clear aqueous solution" refers to an aqueous solution containing cabazitaxel and HSA that is transparent and substantially free of visible particles or precipitation of undissolved cabazitaxel when visually observed. For example, the term "clear aqueous solution" excludes a milky aqueous solution. Further, the term "transparent aqueous solution" excludes a cloudy or hazy aqueous solution.

As used herein, the term "substantially free of visible particles or precipitation of undissolved cabazitaxel" can be assessed as follows: after a clear aqueous solution is filtered with a 0.22 micron filter, the amount of cabazitaxel in the filtered clear aqueous solution is at least 95% of the total amount of cabazitaxel in the clear aqueous solution before filtration. The total amount of cabazitaxel in the aqueous solution before filtration includes the particles or precipitation of undissolved cabazitaxel in the aqueous solution or with the aqueous solution. The amount of the cabazitaxel in a clear aqueous solution can be measured by methods using HPLC. The methods of measuring the amount of the cabazitaxel in a clear aqueous solution are illustrated in the experimental examples described herein. The methods are commonly understood by one of ordinary skill in the art to which this disclosure belongs.

As used herein, the term "micron" refers to a unit of measure of one one-thousandth of a millimeter. In some embodiments, the term "micron" refers to a micrometer.

As used herein, "substantially free of solvent," in reference to an aqueous solution, refers to an aqueous solution that contains less than 0.5%, by weight, of any non-water solvent. In some embodiments, the aqueous solution contains less than 0.1%, by weight, of any non-water solvent. In some embodiments, the aqueous solution contains less than 0.05%, by weight, of any non-water solvent.

As used herein, the term "aqueous solution" refers to a solution, wherein at least one solvent is water and the weight % of water in the mixture of solvents is at least 50%, at least 60%, at least 70% or at least 90%. In some embodiments, aqueous solution is a solution in which water is the only solvent. In some embodiments, aqueous solution is 0.9% saline solution. In some embodiments, aqueous solution is 5% dextrose water solution. In some embodiments, aqueous solution is a buffer (e.g., phosphate buffer or a carbonate buffer). In some embodiments, the buffer is physiological buffer or a pharmaceutically acceptable buffer. In some embodiments, the buffer is any one of buffers described, for example, in Y.-C. Lee et al. International Journal of Pharmaceutics 253 (2003) 111-119, the disclosure of which is incorporated herein by reference in its entirety. In some embodiments, the buffer comprises maleic acid, tartaric acid, lactic acid, citric acid, acetic acid, sodium bicarbonate, sodium phosphate, or mixtures thereof. In some embodiments, the pH range of the buffer is from about 3 to about 9, from about 4 to about 8, from about 5 to about 7, from about 6 to about 7, from about 3 to about 5, from about 3 to about 7, from about 4 to about 6, or from about 6 to about 6. In some embodiments, the pH of the buffer is about 4, about 5, about 6, about 6.4, about 6.5, about 6.6, about 7, about 7.5, or about 8.

As used herein, the term "aqueous solvent" refer to a liquid comprising at least 50%, at least 60%, at least 70%, at least 90% or at least 95% water. In some embodiments, aqueous solvent is water.

In some embodiments, provided herein is a composition comprising a non-covalently bound complex comprising cabazitaxel and human serum albumin, wherein the cabazitaxel and the human serum albumin in the composition have a ratio by weight from about 1:150 to about 1:1000, wherein the composition is a clear aqueous solution when the composition is dissolved in an aqueous solvent, and wherein the clear aqueous solution has pH value from about 5 to about 8.

In some embodiments, provided herein is a composition comprising a non-covalently bound complex comprising cabazitaxel and human serum albumin, wherein the cabazitaxel and the human serum albumin in the composition have a ratio by weight from about 1:150 to about 1:1000, wherein the composition is a clear aqueous solution when the composition is dissolved in an aqueous solvent, and wherein the clear aqueous solution has pH value from about 6 to about 7.5.

In some embodiments, provided herein is a composition comprising a non-covalently bound complex comprising cabazitaxel and human serum albumin, wherein the cabazitaxel and the human serum albumin in the composition have a ratio by weight from about 1:200 to about 1:600, wherein the composition is a clear aqueous solution when the composition is dissolved in an aqueous solvent, and wherein the clear aqueous solution has pH value from about 5 to about 8.

In some embodiments, provided herein is a composition comprising a non-covalently bound complex comprising cabazitaxel and human serum albumin, wherein the cabazitaxel and the human serum albumin in the composition have a ratio by weight from about 1:200 to about 1:600, wherein the composition is a clear aqueous solution when the composition is dissolved in an aqueous solvent, and wherein the clear aqueous solution has pH value from about 6 to about 7.5.

In some embodiments, provided herein is a composition comprising a non-covalently bound complex comprising cabazitaxel and human serum albumin, wherein the cabazitaxel and the human serum albumin in the composition have a ratio by weight from about 1:250 to about 1:500, wherein the composition is a clear aqueous solution when the composition is dissolved in an aqueous solvent, and wherein the clear aqueous solution has pH value from about 5 to about 8.

In some embodiments, provided herein is a composition comprising a non-covalently bound complex comprising cabazitaxel and human serum albumin, wherein the cabazitaxel and the human serum albumin in the composition have a ratio by weight from about 1:250 to about 1:500, wherein the composition is a clear aqueous solution when the composition is dissolved in an aqueous solvent, and wherein the clear aqueous solution has pH value from about 6 to about 7.5.

In some embodiments, provided herein is a composition comprising a non-covalently bound complex comprising cabazitaxel and human serum albumin, wherein the cabazitaxel and the human serum albumin in the composition have a ratio by weight from about 1:150 to about 1:1000, wherein the composition is a clear aqueous solution when the composition is dissolved in an aqueous solvent, and wherein the clear aqueous solution has pH value from about 5 to about 8, and wherein the clear aqueous solution is substantially free of solvent other than water. In some embodiments, provided herein is a composition comprising a non-covalently bound complex comprising cabazitaxel and human serum albumin, wherein the cabazitaxel and the human serum albumin in the composition have a ratio by weight from about 1:150 to about 1:1000, wherein the composition is a clear aqueous solution when the composition is dissolved in an aqueous solvent, and wherein the clear aqueous solution has pH value from about 5 to about 8, and wherein the clear aqueous solution is free of solvent other than water.

In some embodiments, provided herein is a composition comprising a non-covalently bound complex comprising cabazitaxel and human serum albumin, wherein the cabazitaxel and the human serum albumin in the composition have a ratio by weight from about 1:200 to about 1:600, wherein the composition is a clear aqueous solution when the composition is dissolved in an aqueous solvent, and wherein the clear aqueous solution has pH value from about 5 to about 8, and wherein the clear aqueous solution is substantially free of solvent other than water. In some embodiments, provided herein is a composition comprising a non-covalently bound complex comprising cabazitaxel and human serum albumin, wherein the cabazitaxel and the human serum albumin in the composition have a ratio by weight from about 1:200 to about 1:600, wherein the composition is a clear aqueous solvent when the composition is dissolved in an aqueous solution, and wherein the clear aqueous solution has pH value from about 5 to about 8, and wherein the clear aqueous solution is free of solvent other than water.

In some embodiments, provided herein is a composition comprising a non-covalently bound complex comprising cabazitaxel and human serum albumin, wherein the cabazitaxel and the human serum albumin in the composition have a ratio by weight from about 1:250 to about 1:500, wherein the composition is a clear aqueous solution when the composition is dissolved in an aqueous solvent, and wherein the clear aqueous solution has pH value from about 5 to about 8, and wherein the clear aqueous solution is substantially free of solvent other than water. In some embodiments, provided herein is a composition comprising a non-covalently bound complex comprising cabazitaxel and human serum albumin, wherein the cabazitaxel and the human serum albumin in the composition have a ratio by weight from about 1:250 to about 1:500, wherein the composition is a clear aqueous solution when the composition is dissolved in an aqueous solvent, and wherein the clear aqueous solution has pH value from about 5 to about 8, and wherein the clear aqueous solution is free of solvent other than water.

In some embodiments, provided herein is a composition comprising a non-covalently bound complex comprising cabazitaxel and human serum albumin, wherein the cabazitaxel and the human serum albumin in the composition have a ratio by weight from about 1:150 to about 1:1000, wherein the composition is a clear aqueous solution when the composition is dissolved in an aqueous solvent, and wherein the clear aqueous solution has pH value from about 6 to about 7.5, and wherein the clear aqueous solution is substantially free of solvent other than water. In some embodiments, provided herein is a composition comprising a non-covalently bound complex comprising cabazitaxel and human serum albumin, wherein the cabazitaxel and the human serum albumin in the composition have a ratio by weight from about 1:150 to about 1:1000, wherein the composition is a clear aqueous solution when the composition is dissolved in an aqueous solvent, and wherein the clear aqueous solution has pH value from about 6 to about 7.5, and wherein the clear aqueous solution is free of solvent other than water.

In some embodiments, provided herein is a composition comprising a non-covalently bound complex comprising cabazitaxel and human serum albumin, wherein the cabazitaxel and the human serum albumin in the composition have a ratio by weight from about 1:200 to about 1:600, wherein the composition is a clear aqueous solution when the composition is dissolved in an aqueous solvent, and wherein the clear aqueous solution has pH value from about 6 to about 7.5, and wherein the clear aqueous solution is substantially free of solvent other than water. In some embodiments, provided herein is a composition comprising a non-covalently bound complex comprising cabazitaxel and human serum albumin, wherein the cabazitaxel and the human serum albumin in the composition have a ratio by weight from about 1:200 to about 1:600, wherein the composition is a clear aqueous solution when the composition is dissolved in an aqueous solvent, and wherein the clear aqueous solution has pH value from about 6 to about 7.5, and wherein the clear aqueous solution is free of solvent other than water.

In some embodiments, provided herein is a composition comprising a non-covalently bound complex comprising cabazitaxel and human serum albumin, wherein the cabazitaxel and the human serum albumin in the composition have a ratio by weight from about 1:250 to about 1:500, wherein the composition is a clear aqueous solution when the composition is dissolved in an aqueous solvent, and wherein the clear aqueous solution has pH value from about 6 to about 7.5, and wherein the clear aqueous solution is substantially free of solvent other than water. In some embodiments, provided herein is a composition comprising a non-covalently bound complex comprising cabazitaxel and human serum albumin, wherein the cabazitaxel and the human serum albumin in the composition have a ratio by weight from about 1:250 to about 1:500, wherein the composition is a clear aqueous solution when the composition is dissolved in an aqueous solvent, and wherein the clear aqueous solution has pH value from about 6 to about 7.5, and wherein the clear aqueous solution is free of solvent other than water.

In some embodiments, the composition is a clear aqueous solution when the composition is dissolved in water. In some embodiments, the composition is a clear aqueous solution when the composition is dissolved in 0.9% saline. In some embodiments, the composition is a clear aqueous solution when the composition is dissolved in 5% dextrose solution.

In some embodiments, the composition forms a clear aqueous solution, when the composition is dissolved in an aqueous solvent, wherein the clear aqueous solution has pH value from about 5 to about 8. In some embodiments, the composition forms a clear aqueous solution, when the composition is dissolved in an aqueous solvent, wherein the clear aqueous solution has pH value from about 5.5 to about 7.8. In some embodiments, the composition forms a clear aqueous solution, when the composition is dissolved in an aqueous solvent, wherein the clear aqueous solution has pH value from about 6 to about 7.5. In some embodiments, the composition forms a clear aqueous solution, when the composition is dissolved in an aqueous solvent, wherein the clear aqueous solution has pH value from about 6.5 to about 7.5. In some embodiments, the composition forms a clear aqueous solution, when the composition is dissolved in an aqueous solvent, wherein the clear aqueous solution has pH value from about 6 to about 6.5. In some embodiments, the composition forms a clear aqueous solution, when the composition is dissolved in an aqueous solvent, wherein the clear aqueous solution has pH value from about 6.5 to about 7. In some embodiments, the composition forms a clear aqueous solution, when the composition is dissolved in an aqueous solvent, wherein the clear aqueous solution has pH value from about 7 to about 7.5. In some embodiments, the composition forms a clear aqueous solution, when the composition is dissolved in an aqueous solvent, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5. In some embodiments, the aqueous solution is substantially free of solvent other than water. In some embodiments, the aqueous solution is free of solvent other than water.

In some embodiments, the composition forms a clear aqueous solution, when the composition is dissolved in water, wherein the clear aqueous solution has pH value from about 5 to about 8. In some embodiments, the composition forms a clear aqueous solution, when the composition is dissolved in water, wherein the clear aqueous solution has pH value from about 5.5 to about 7.8. In some embodiments, the composition forms a clear aqueous solution, when the composition is dissolved in water, wherein the clear aqueous solution has pH value from about 6 to about 7.5. In some embodiments, the composition forms a clear aqueous solution, when the composition is dissolved in water, wherein the clear aqueous solution has pH value from about 6.5 to about 7.5. In some embodiments, the composition forms a clear aqueous solution, when the composition is dissolved in water, wherein the clear aqueous solution has pH value from about 6 to about 6.5. In some embodiments, the composition forms a clear aqueous solution, when the composition is dissolved in water, wherein the clear aqueous solution has pH value from about 6.5 to about 7. In some embodiments, the composition forms a clear aqueous solution, when the composition is dissolved in water, wherein the clear aqueous solution has pH value from about 7 to about 7.5. In some embodiments, the composition forms a clear aqueous solution, when the composition is dissolved in water, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5.

In some embodiments, the composition forms a clear aqueous solution, when the composition is dissolved in 0.9% saline, wherein the clear aqueous solution has pH value from about 5 to about 8. In some embodiments, the composition forms a clear aqueous solution, when the composition is dissolved in 0.9% saline, wherein the clear aqueous solution has pH value from about 5.5 to about 7.8. In some embodiments, the composition forms a clear aqueous solution, when the composition is dissolved in 0.9% saline, wherein the clear aqueous solution has pH value from about 6 to about 7.5. In some embodiments, the composition forms a clear aqueous solution, when the composition is dissolved in 0.9% saline, wherein the clear aqueous solution has pH value from about 6.5 to about 7.5. In some embodiments, the composition forms a clear aqueous solution, when the composition is dissolved in 0.9% saline, wherein the clear aqueous solution has pH value from about 6 to about 6.5. In some embodiments, the composition forms a clear aqueous solution, when the composition is dissolved in 0.9% saline, wherein the clear aqueous solution has pH value from about 6.5 to about 7. In some embodiments, the composition forms a clear aqueous solution, when the composition is dissolved in 0.9% saline, wherein the clear aqueous solution has pH value from about 7 to about 7.5. In some embodiments, the composition forms a clear aqueous solution, when the composition is dissolved in 0.9% saline, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5.

In some embodiments, the composition forms a clear aqueous solution, when the composition is dissolved in 5% dextrose solution, wherein the clear aqueous solution has pH value from about 5 to about 8. In some embodiments, the composition forms a clear aqueous solution, when the composition is dissolved in 5% dextrose solution, wherein the clear aqueous solution has pH value from about 5.5 to about 7.8. In some embodiments, the composition forms a clear aqueous solution, when the composition is dissolved in 5% dextrose solution, wherein the clear aqueous solution has pH value from about 6 to about 7.5. In some embodiments, the composition forms a clear aqueous solution, when the composition is dissolved in 5% dextrose solution, wherein the clear aqueous solution has pH value from about 6.5 to about 7.5. In some embodiments, the composition forms a clear aqueous solution, when the composition is dissolved in 5% dextrose solution, wherein the clear aqueous solution has pH value from about 6 to about 6.5. In some embodiments, the composition forms a clear aqueous solution, when the composition is dissolved in 5% dextrose solution, wherein the clear aqueous solution has pH value from about 6.5 to about 7. In some embodiments, the composition forms a clear aqueous solution, when the composition is dissolved in 5% dextrose solution, wherein the clear aqueous solution has pH value from about 7 to about 7.5. In some embodiments, the composition forms a clear aqueous solution, when the composition is dissolved in 5% dextrose solution, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5.

In some embodiments, the composition is a clear aqueous solution when the composition is dissolved in an aqueous solvent (e.g. water, 0.9% saline, or 5% dextrose solution), wherein after the clear aqueous solution is filtered by a 0.22 micron filter, the amount of cabazitaxel in the filtered aqueous solution is at least 95% of the total amount of cabazitaxel in the aqueous solution before the filtration. In some embodiments, the composition is a clear aqueous solution when the composition is dissolved in an aqueous solvent (e.g. water, 0.9% saline, or 5% dextrose solution), wherein after the clear aqueous solution is filtered by a 0.22 micron filter, the amount of cabazitaxel in the filtered aqueous solution is at least 96% of the total amount of cabazitaxel in the aqueous solution before the filtration. In some embodiments, the composition is a clear aqueous solution when the composition is dissolved in an aqueous solvent (e.g. water, 0.9% saline, or 5% dextrose solution), wherein after the clear aqueous solution is filtered by a 0.22 micron filter, the amount of cabazitaxel in the filtered aqueous solution is at least 97% of the total amount of cabazitaxel in the aqueous solution before the filtration. In some embodiments, the composition is a clear aqueous solution when the composition is dissolved in an aqueous solution (e.g. water, 0.9% saline, or 5% dextrose solution), wherein after the clear aqueous solution is filtered by a 0.22 micron filter, the amount of cabazitaxel in the filtered aqueous solution is at least 98% of the total amount of cabazitaxel in the aqueous solution before the filtration. In some embodiments, the composition is a clear aqueous solution when the composition is dissolved in an aqueous solution (e.g. water, 0.9% saline, or 5% dextrose solution), wherein after the clear aqueous solution is filtered by a 0.22 micron filter, the amount of cabazitaxel in the filtered aqueous solution is at least 99% of the total amount of cabazitaxel in the aqueous solution before the filtration. In some embodiments, the composition is a clear aqueous solution when the composition is dissolved in an aqueous solution (e.g. water, 0.9% saline, or 5% dextrose solution), wherein after the clear aqueous solution is filtered by a 0.22 micron filter, the amount of cabazitaxel in the filtered aqueous solution is at least 99.5% of the total amount of cabazitaxel in the aqueous solution before the filtration. In some embodiments, the aqueous solution is free of solvent other than water. In some embodiments, the aqueous solution is substantially free of solvent other than water.

In some embodiments, the composition is a clear aqueous solution when the composition is dissolved in an aqueous solution, wherein after the clear aqueous solution is filtered by a 0.22 micron filter, the amount of cabazitaxel in the filtered aqueous solution is at least 95%, 96%, 97%, 98%, 99%, or 99.5% of the total amount of cabazitaxel in the aqueous solution before the filtration, wherein the clear aqueous solution has pH value from about 5 to about 8, and wherein the clear aqueous solution is substantially free of solvent other than water. In some embodiments, the composition is a clear aqueous solution when the composition is dissolved in an aqueous solution, wherein after the clear aqueous solution is filtered by a 0.22 micron filter, the amount of cabazitaxel in the filtered aqueous solution is at least 95%, 96%, 97%, 98%, 99%, or 99.5% of the total amount of cabazitaxel in the aqueous solution before the filtration, wherein the clear aqueous solution has pH value from about 6 to about 7.5, and wherein the clear aqueous solution is substantially free of solvent other than water. In some embodiments, the composition is a clear aqueous solution when the composition is dissolved in an aqueous solution, wherein after the clear aqueous solution is filtered by a 0.22 micron filter, the amount of cabazitaxel in the filtered aqueous solution is at least 95%, 96%, 97%, 98%, 99%, or 99.5% of the total amount of cabazitaxel in the aqueous solution before the filtration, wherein the clear aqueous solution has pH value from about 5 to about 8, and wherein the clear aqueous solution is free of solvent other than water. In some embodiments, the composition is a clear aqueous solution when the composition is dissolved in an aqueous solution, wherein after the clear aqueous solution is filtered by a 0.22 micron filter, the amount of cabazitaxel in the filtered aqueous solution is at least 95%, 96%, 97%, 98%, 99%, or 99.5% of the total amount of cabazitaxel in the aqueous solution before the filtration, wherein the clear aqueous solution has pH value from about 6 to about 7.5, and wherein the clear aqueous solution is free of solvent other than water.

In some embodiments, the amount of cabazitaxel that is bound to the HSA (e.g., non-covalently) in the aqueous solution (e.g., clear aqueous solution) comprising the composition comprising a non-covalently bound complex comprising cabazitaxel and human serum albumin (as described herein) is at least 40%, at least 50%, at least 60%, at least 70%, at least 80%, at least 90%, at least 95%, at least 99%, or about 100% of the total about of cabazitaxel in the aqueous solution.

In some embodiments, the composition is an aqueous solution, wherein after the aqueous solution is filtered by a 0.22 micron filter, the amount of cabazitaxel in the filtered aqueous solution is at least 80% of the total amount of cabazitaxel in the aqueous solution before the filtration. In some embodiments, the composition is an aqueous solution, wherein after the aqueous solution is filtered by a 0.22 micron filter, the amount of cabazitaxel in the filtered aqueous solution is at least 85% of the total amount of cabazitaxel in the aqueous solution before the filtration. In some embodiments, the composition is an aqueous solution, wherein after the aqueous solution is filtered by a 0.22 micron filter, the amount of cabazitaxel in the filtered aqueous solution is at least 90% of the total amount of cabazitaxel in the aqueous solution before the filtration. In some embodiments, the aqueous solution is free of solvent other than water. In some embodiments, the aqueous solution is substantially free of solvent other than water.

In some embodiments, the composition is a clear aqueous solution for at least 1 hour when the composition is dissolved in an aqueous solution (e.g. water, 0.9% saline, or 5% dextrose solution). In some embodiments, the composition is a clear aqueous solution for at least 2 hours when the composition is dissolved in an aqueous solution (e.g. water, 0.9% saline, or 5% dextrose solution). In some embodiments, the composition is a clear aqueous solution for at least 3 hours when the composition is dissolved in an aqueous solution (e.g. water, 0.9% saline, or 5% dextrose solution). In some embodiments, the composition is a clear aqueous solution for at least 4 hours when the composition is dissolved in an aqueous solution (e.g. water, 0.9% saline, or 5% dextrose solution). In some embodiments, the composition is a clear aqueous solution for at least 5 hours when the composition is dissolved in an aqueous solution (e.g. water, 0.9% saline, or 5% dextrose solution). In some embodiments, the composition is a clear aqueous solution for at least 6 hours when the composition is dissolved in an aqueous solution (e.g. water, 0.9% saline, or 5% dextrose solution). In some embodiments, the composition is a clear aqueous solution for at least 8 hours when the composition is dissolved in an aqueous solution (e.g. water, 0.9% saline, or 5% dextrose solution). In some embodiments, the composition is a clear aqueous solution for at least 24 hours when the composition is dissolved in an aqueous solution (e.g. water, 0.9% saline, or 5% dextrose solution). In some embodiments, the composition is a clear aqueous solution for at least 3 days when the composition is dissolved in an aqueous solution (e.g. water, 0.9% saline, or 5% dextrose solution). In some embodiments, the aqueous solution is substantially free of solvent other than water. In some embodiments, the aqueous solution is free of solvent other than water.

In some embodiments, the composition is a solid formulation. For example, the solid formulation can be produced in a uniform manner by lyophilization. A skilled artisan would recognize other methods, such as rotary evaporation, that can also produce solid formulations.

In some embodiments, the composition is an aqueous formulation. In some embodiments, the aqueous formulation is substantially free of solvent other than water. In some embodiments, the aqueous formulation is free of solvent other than water. In some embodiments, the aqueous formulation includes water and water-miscible organic solvents including at least one of polyethylene glycol 300, polyethylene glycol 400, ethanol, methanol, propylene glycol, glycerin, N-methyl-2-pyrrolidone, dimethylacetamide, and dimethylsulfoxide. For example, the water-miscible organic solvent can include ethanol. In some embodiments, the aqueous formulation includes water and ethanol. In some embodiments, the water-miscible organic solvent can be a mixture of water-miscible organic solvents. In some embodiments, the pH of the aqueous formulation (e.g., clear aqueous solution) is neutral (e.g., pH of the composition is from about 5 to about 8, from about 5.5 to about 7.5, or from about 6 to about 7, or the pH od the composition is about 5, about 5.5, about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5 or about 8).

In some embodiments, the aqueous formulation can be free of a surfactant. In some embodiments, the aqueous formulation can be free of a surfactant, such as CREMOPHOR® surfactants and Polysorbate 80. In some embodiments, the aqueous formulation can be substantially free of a surfactant, such as CREMOPHOR® surfactants and Polysorbate 80. In some embodiments, the aqueous formulation can be substantially free of a surfactant selected from the group consisting of CREMOPHOR® surfactants and Polysorbate 80.

As used herein, the term "substantially free of surfactant" refers to a formulation containing less than 0.0005%, less than 0.0003%, or less than 0.0001% of surfactants and/or less than 0.0005%, less than 0.0003%, or less than 0.0001% of surfactant.

In some embodiments, the aqueous formulation is a clear aqueous solution. For example, the formulation can be a clear and stable aqueous solution reconstituted from a sterile lyophilized powder. In some embodiments, the aqueous formulation is a clear aqueous solution, wherein the aqueous formulation is substantially free of solvent other than water. In some embodiments, the aqueous formulation is a clear aqueous solution, wherein the aqueous formulation is free of solvent other than water.

In some embodiments, the aqueous formulation is a clear aqueous solution reconstituted from the solid formulation (e.g. the sterile lyophilized powder) in water. In some embodiments, the aqueous formulation is a clear aqueous solution reconstituted from the solid formulation (e.g. the sterile lyophilized powder) in 0.9% saline. In some embodiments, the aqueous formulation is a clear aqueous solution reconstituted from the solid formulation (e.g. the sterile lyophilized powder) in 5% dextrose solution.

In some embodiments, the aqueous formulation is a clear aqueous solution reconstituted from the solid formulation (e.g. the sterile lyophilized powder) in water, wherein the aqueous formulation has pH value from about 5 to about 8. In some embodiments, the aqueous formulation is a clear aqueous solution reconstituted from the solid formulation (e.g. the sterile lyophilized powder) in 0.9% saline, wherein the aqueous formulation has pH value from about 5 to about 8. In some embodiments, the aqueous formulation is a clear aqueous solution reconstituted from the solid formulation (e.g. the sterile lyophilized powder) in 5% dextrose solution, wherein the aqueous formulation has pH value from about 5 to about 8.

In some embodiments, the aqueous formulation is a clear aqueous solution reconstituted from the solid formulation (e.g. the sterile lyophilized powder) in water, wherein the pH of water is about 7, and wherein the aqueous formulation has pH value from about 5 to about 8. In some embodiments, the aqueous formulation is a clear aqueous solution reconstituted from the solid formulation (e.g. the sterile lyophilized powder) in 0.9% saline solution, wherein the pH of 0.9% saline solution is about 5.4, and wherein the aqueous formulation has pH value from about 5 to about 8. In some embodiments, the aqueous formulation is a clear aqueous solution reconstituted from the solid formulation (e.g. the sterile lyophilized powder) in 5% dextrose water solution, wherein the pH of 5% dextrose solution is about 4.4, and wherein the aqueous formulation has pH value from about 5 to about 8. In some aspects of the aforementioned embodiments, the concentration of the reconstituted solid in the aqueous formulation is about 25 mg, about 50 mg, about 75 mg, about 100 mg, about 150 mg or 200 mg per 1 mL of the aqueous solvent. In some aspects of the aforementioned embodiments, the concentration of the reconstituted solid in the aqueous formulation is from about 10 mg to about 200 mg per 1 mL of the aqueous solvent.

In some embodiments, the aqueous formulation is a clear aqueous solution reconstituted from the solid formulation (e.g. the sterile lyophilized powder) in water, wherein the aqueous formulation has pH value from about 6 to about 7.5. In some embodiments, the aqueous formulation is a clear aqueous solution reconstituted from the solid formulation (e.g. the sterile lyophilized powder) in 0.9% saline, wherein the aqueous formulation has pH value from about 6 to about 7.5. In some embodiments, the aqueous formulation is a clear aqueous solution reconstituted from the solid formulation (e.g. the sterile lyophilized powder) in 5% dextrose solution, wherein the aqueous formulation has pH value from about 6 to about 7.5.

In some embodiments, the aqueous formulation is a clear aqueous solution reconstituted from the solid formulation (e.g. the sterile lyophilized powder) in water, wherein the pH of water is about 7, and wherein the aqueous formulation has pH value from about 6 to about 7.5. In some embodiments, the aqueous formulation is a clear aqueous solution reconstituted from the solid formulation (e.g. the sterile lyophilized powder) in 0.9% saline solution, wherein the pH of 0.9% saline solution is about 5.4, and wherein the aqueous formulation has pH value from about 6 to about 7.5. In some embodiments, the aqueous formulation is a clear aqueous solution reconstituted from the solid formulation (e.g. the sterile lyophilized powder) in 5% dextrose water solution, wherein pH of the 5% dextrose solution is about 4.4, and wherein the aqueous formulation has pH value from about 6 to about 7.5.

In some embodiments, the aqueous formulation is a clear aqueous solution reconstituted from the solid formulation (e.g. the sterile lyophilized powder) in water, wherein the pH of water is about 7, and wherein the aqueous formulation has pH value of about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8. In some embodiments, the aqueous formulation is a clear aqueous solution reconstituted from the solid formulation (e.g. the sterile lyophilized powder) in 0.9% saline solution, wherein the pH of 0.9% saline solution is about 5.4, and wherein the aqueous formulation has pH value of about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8. In some embodiments, the aqueous formulation is a clear aqueous solution reconstituted from the solid formulation (e.g. the sterile lyophilized powder) in 5% dextrose water solution, wherein pH of the 5% dextrose solution is about 4.4, and wherein the aqueous formulation has pH value of about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8.

In some embodiments, the aqueous formulation has pH value from about 5 to about 8. In some embodiments, the aqueous formulation has pH value from about 5.5 to about 7.8. In some embodiments, the aqueous formulation has pH value from about 6 to about 7.5. In some embodiments, the aqueous formulation has pH value from about 6.5 to about 7.5. In some embodiments, the aqueous formulation has pH value from about 6 to about 6.5. In some embodiments, the aqueous formulation has pH value from about 6.5 to about 7. In some embodiments, the aqueous formulation has pH value from about 7 to about 7.5. In some embodiments, the aqueous formulation has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5. In some embodiments, the aqueous formulation is substantially free of solvent other than water. In some embodiments, the aqueous formulation is free of solvent other than water.

In some embodiments, the aqueous formulation is a clear aqueous solution, wherein the aqueous formulation has pH value from about 5 to about 8, and wherein the aqueous formulation is substantially free of solvent other than water. In some embodiments, the aqueous formulation is a clear aqueous solution, wherein the aqueous formulation has pH value from about 5 to about 8, and wherein the aqueous formulation is free of solvent other than water. In some embodiments, the aqueous formulation is a clear aqueous solution, wherein the aqueous formulation has pH value from about 5.5 to about 7.8, and wherein the aqueous formulation is substantially free of solvent other than water. In some embodiments, the aqueous formulation is a clear aqueous solution, wherein the aqueous formulation has pH value from about 5.5 to about 7.8, and wherein the aqueous formulation is free of solvent other than water. In some embodiments, the aqueous formulation is a clear aqueous solution, wherein the aqueous formulation has pH value from about 6 to about 7.5, and wherein the aqueous formulation is substantially free of solvent other than water. In some embodiments, the aqueous formulation is a clear aqueous solution, wherein the aqueous formulation has pH value from about 6 to about 7.5, and wherein the aqueous formulation is free of solvent other than water. In some embodiments, the aqueous formulation is a clear aqueous solution, wherein the aqueous formulation has pH value from about 6.5 to about 7.5, and wherein the aqueous formulation is substantially free of solvent other than water. In some embodiments, the aqueous formulation is a clear aqueous solution, wherein the aqueous formulation has pH value from about 6.5 to about 7.5, and wherein the aqueous formulation is free of solvent other than water. In some embodiments, the aqueous formulation is a clear aqueous solution, wherein the aqueous formulation has pH value from about 6 to about 6.5, and wherein the aqueous formulation is substantially free of solvent other than water. In some embodiments, the aqueous formulation is a clear aqueous solution, wherein the aqueous formulation has pH value from about 6 to about 6.5, and wherein the aqueous formulation is free of solvent other than water. In some embodiments, the aqueous formulation is a clear aqueous solution, wherein the aqueous formulation has pH value from about 6.5 to about 7, and wherein the aqueous formulation is substantially free of solvent other than water. In some embodiments, the aqueous formulation is a clear aqueous solution, wherein the aqueous formulation has pH value from about 6.5 to about 7, and wherein the aqueous formulation is free of solvent other than water. In some embodiments, the aqueous formulation is a clear aqueous solution, wherein the aqueous formulation has pH value from about 7 to about 7.5, and wherein the aqueous formulation is substantially free of solvent other than water. In some embodiments, the aqueous formulation is a clear aqueous solution, wherein the aqueous formulation has pH value from about 7 to about 7.5, and wherein the aqueous formulation is free of solvent other than water. In some embodiments, the aqueous formulation is a clear aqueous solution, wherein the aqueous formulation has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5, and wherein the aqueous formulation is substantially free of solvent other than water. In some embodiments, the aqueous formulation is a clear aqueous solution, wherein the aqueous formulation has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5, and wherein the aqueous formulation is free of solvent other than water.

In some embodiments, after the aqueous formulation is filtered by a 0.22 micron filter, the amount of cabazitaxel in the filtered aqueous solution is at least 95% of the total amount of cabazitaxel in the aqueous solution before the filtration. In some embodiments, after the aqueous formulation is filtered by a 0.22 micron filter, the amount of cabazitaxel in the filtered aqueous solution is at least 96% of the total amount of cabazitaxel in the aqueous solution before the filtration. In some embodiments, after the aqueous formulation is filtered by a 0.22 micron filter, the amount of cabazitaxel in the filtered aqueous solution is at least 97% of the total amount of cabazitaxel in the aqueous solution before the filtration. In some embodiments, after the aqueous formulation is filtered by a 0.22 micron filter, the amount of cabazitaxel in the filtered aqueous solution is at least 98% of the total amount of cabazitaxel in the aqueous solution before the filtration. In some embodiments, after the aqueous formulation is filtered by a 0.22 micron filter, the amount of cabazitaxel in the filtered aqueous solution is at least 99% of the total amount of cabazitaxel in the aqueous solution before the filtration. In some embodiments, after the aqueous formulation is filtered by a 0.22 micron filter, the amount of cabazitaxel in the filtered aqueous solution is at least 99.5% of the total amount of cabazitaxel in the aqueous solution before the filtration. In some aspects of these embodiments, the aqueous formulation is filtered by a 0.22-micron filter at a time period selected from 1 hour, 2 hours, 3, hours, 4 hours, 5 hours, 6 hours, 8 hours, 12 hours, 18 hours and 24 hours. In some embodiments, the aqueous formulation is free of solvent other than water. In some embodiments, the aqueous formulation is substantially free of solvent other than water.

In some embodiments, after the aqueous formulation (e.g. a clear aqueous solution) is filtered by a 0.22 micron filter, the amount of cabazitaxel in the filtered aqueous solution is at least 95%, 96%, 97%, 98%, 99%, or 99.5% of the total amount of cabazitaxel in the aqueous solution before filtration, wherein the clear aqueous solution has pH value from about 5 to about 8, and wherein the clear aqueous solution is substantially free of solvent other than water. In some embodiments, after the aqueous formulation (e.g. a clear aqueous solution) is filtered by a 0.22 micron filter, the amount of cabazitaxel in the filtered aqueous solution is at least 95%, 96%, 97%, 98%, 99%, or 99.5% of the total amount of cabazitaxel in the aqueous solution before filtration, wherein the clear aqueous solution has pH value from about 6 to about 7.5, and wherein the clear aqueous solution is substantially free of solvent other than water. In some embodiments, after the aqueous formulation (e.g. a clear aqueous solution) is filtered by a 0.22 micron filter, the amount of cabazitaxel in the filtered aqueous solution is at least 95%, 96%, 97%, 98%, 99%, or 99.5% of the total amount of cabazitaxel in the aqueous solution before filtration, wherein the clear aqueous solution has pH value from about 5 to about 8, and wherein the clear aqueous solution is free of solvent other than water. In some embodiments, after the aqueous formulation (e.g. a clear aqueous solution) is filtered by a 0.22 micron filter, the amount of cabazitaxel in the filtered aqueous solution is at least 95%, 96%, 97%, 98%, 99%, or 99.5% of the total amount of cabazitaxel in the aqueous solution before filtration, wherein the clear aqueous solution has pH value from about 6 to about 7.5, and wherein the clear aqueous solution is free of solvent other than water. In some aspects of these embodiments, the aqueous formulation is filtered by a 0.22-micron filter at a time period selected from 1 hour, 2 hours, 3, hours, 4 hours, 5 hours, 6 hours, 8 hours, 12 hours, 18 hours and 24 hours.

In some embodiments, after the aqueous formulation is filtered by a 0.22 micron filter, the amount of cabazitaxel in the filtered aqueous solution is at least 80% of the total amount of cabazitaxel in the aqueous solution before the filtration. In some embodiments, after the aqueous formulation is filtered by a 0.22 micron filter, the amount of cabazitaxel in the filtered aqueous solution is at least 85% of the total amount of cabazitaxel in the aqueous solution before the filtration. In some embodiments, after the aqueous formulation is filtered by a 0.22 micron filter, the amount of cabazitaxel in the filtered aqueous solution is at least 90% of the total amount of cabazitaxel in the aqueous solution before the filtration. In some aspects of these embodiments, the aqueous formulation is filtered by a 0.22-micron filter at a time period selected from 1 hour, 2 hours, 3, hours, 4 hours, 5 hours, 6 hours, 8 hours, 12 hours, 18 hours and 24 hours. In some embodiments, the aqueous formulation is free of solvent other than water. In some embodiments, the aqueous formulation is substantially free of solvent other than water.

In some embodiments, the aqueous formulation is a clear aqueous solution for at least 1 hour. In some embodiments, the aqueous formulation is a clear aqueous solution for at least 2 hours. In some embodiments, the aqueous formulation is a clear aqueous solution for at least 3 hours. In some embodiments, the aqueous formulation is a clear aqueous solution for at least 4 hours. In some embodiments, the aqueous formulation is a clear aqueous solution for at least 5 hours. In some embodiments, the aqueous formulation is a clear aqueous solution for at least 6 hours. In some embodiments, the aqueous formulation is a clear aqueous solution for at least 8 hours. In some embodiments, the aqueous formulation is a clear aqueous solution for at least 24 hours. In some embodiments, the aqueous formulation is a clear aqueous solution for at least 6 hours at a concentration of from about 5 mg/mL to about 250 mg/mL, from about 10 mg/mL to about 200 mg/mL, from about 25 mg/mL to about 150 mg/mL, from about 10 mg/mL to about 50 mg/mL, from about 50 mg/mL to about 100 mg/mL, from about 100 mg/mL to about 150 mg/mL, from about 150 mg/mL to about 200 mg/mL, or about 5 mg/mL, about 10 mg/mL, about 20 mg/mL, about 30 mg/mL, about 40 mg/mL, about 50 mg/mL, about 60 mg/mL, about 70 mg/mL, about 80 mg/mL, about 90 mg/mL, or about 100 mg/mL at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 24 hours. In some embodiments, the aqueous formulation is a transparent aqueous solution for at least 24 hours at a concentration of from about 5 mg/mL to about 250 mg/mL, from about 10 mg/mL to about 200 mg/mL, from about 25 mg/mL to about 150 mg/mL, from about 10 mg/mL to about 50 mg/mL, from about 50 mg/mL to about 100 mg/mL, from about 100 mg/mL to about 150 mg/mL, from about 150 mg/mL to about 200 mg/mL, or about 5 mg/mL, about 10 mg/mL, about 20 mg/mL, about 30 mg/mL, about 40 mg/mL, about 50 mg/mL, about 60 mg/mL, about 70 mg/mL, about 80 mg/mL, about 90 mg/mL, or about 100 mg/mL at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 3 days. In some embodiments, the aqueous formulation is a transparent aqueous solution for at least 3 days when dissolved in an aqueous solution at a concentration of from about 5 mg/mL to about 250 mg/mL, from about 10 mg/mL to about 200 mg/mL, from about 25 mg/mL to about 150 mg/mL, from about 10 mg/mL to about 50 mg/mL, from about 50 mg/mL to about 100 mg/mL, from about 100 mg/mL to about 150 mg/mL, from about 150 mg/mL to about 200 mg/mL, or about 5 mg/mL, about 10 mg/mL, about 20 mg/mL, about 30 mg/mL, about 40 mg/mL, about 50 mg/mL, about 60 mg/mL, about 70 mg/mL, about 80 mg/mL, about 90 mg/mL, or about 100 mg/mL at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is substantially free of solvent other than water. In some embodiments, the aqueous formulation is free of solvent other than water.

Also, provided herein is a pharmaceutical composition comprising the composition comprising a non-covalently bound complex comprising cabazitaxel and human serum albumin as described herein, and a pharmaceutically acceptable carrier.

In some embodiments, the pharmaceutical composition further comprises at least one anti-cancer drug (e.g., any one of the anti-cancer drugs as described herein).

As used herein, the term "pharmaceutically acceptable carrier" is meant any solution used to solubilize and deliver an agent to a subject. A desirable pharmaceutically acceptable carrier is saline. Other pharmaceutically acceptable carrier and their formulation are known to one skilled in the art and described, for example, in Remington's Pharmaceutical Sciences. (20th edition), ed. A. Gennaro, 2003, Lippincon Williams & Wilkins.

Pharmaceutically acceptable carriers that may be used in the pharmaceutical compositions of the present application include, but are not limited to, ion exchangers, alumina, aluminum stearate, lecithin, serum proteins (other than HSA), buffer substances such as phosphates, glycine, sorbic acid, potassium sorbate, salts or electrolytes, such as protamine sulfate, disodium hydrogen phosphate, potassium hydrogen phosphate, sodium chloride, zinc salts, colloidal silica, magnesium trisilicate, and cellulose-based substances.

Formulations suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

In some embodiments, the pharmaceutical composition is free of a surfactant, such as CREMOPHOR® surfactants and Polysorbate 80. In some embodiments, the pharmaceutical composition is substantially free of a surfactant, such as CREMOPHOR® surfactants and Polysorbate 80. In some embodiments, the pharmaceutical composition can be substantially free of a surfactant selected from the group consisting of CREMOPHOR® surfactants and Polysorbate 80.

Also, provided herein is a method of treating a proliferative disease comprising the step of administering to a subject in need thereof a therapeutically effective amount of a pharmaceutical composition comprising the composition comprising a non-covalently bound complex comprising cabazitaxel and human serum albumin as described herein, and a pharmaceutically acceptable carrier.

As used herein, the terms "individual", "patient", or "subject" are used interchangeably and refer to any animal, including mammals, preferably mice, rats, other rodents, rabbits, dogs, cats, swine, cattle, sheep, horses, or primates, and most preferably humans.

As used herein, the term "proliferative disease" refers to a disease caused by excessive proliferation of cells and turnover of cellular matrix. Non-limiting examples of proliferative diseases include cancer, atherosclerosis, arthritis (e.g. rheumatoid arthritis), psoriasis, fibrosis (e.g. pulmonary fibrosis, idiopathic pulmonary fibrosis), scleroderma and cirrhosis (e.g. cirrhosis of the liver).

Also, provided herein is a method of treating a cancer (e.g., any one of cancers described herein), the method comprising the step of administering to a subject in need thereof a therapeutically effective amount of a pharmaceutical composition comprising the composition comprising a non-covalently bound complex comprising cabazitaxel and human serum albumin as described herein, and a pharmaceutically acceptable carrier.

In some embodiments, the cancer is selected from the group consisting of bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer.

In some embodiments, cancer is selected from sarcoma, angiosarcoma, fibrosarcoma, rhabdomyosarcoma, liposarcoma, myxoma, rhabdomyoma, fibroma, lipoma, teratoma, non-small cell lung cancer (NSCLC), bronchogenic carcinoma squamous cell, undifferentiated small cell, undifferentiated large cell, adenocarcinoma, alveolar bronchiolar carcinoma, bronchial adenoma, sarcoma, lymphoma, chondromatous hamartoma, mesothelioma, gastrointestinal cancer, cancer of the esophagus, squamous cell carcinoma, adenocarcinoma, leiomyosarcoma, lymphoma, cancer of the stomach, carcinoma, lymphoma, leiomyosarcoma, cancer of the pancreas, ductal adenocarcinoma, insulinoma, glucagonoma, gastrinoma, carcinoid tumor, vipoma, cancer of the small bowel, adenocarcinoma, lymphoma, carcinoid tumors, Kaposi's sarcoma, leiomyoma, hemangioma, lipoma, neurofibroma, fibroma, cancer of the large bowel or colon, tubular adenoma, villous adenoma, hamartoma, leiomyoma, genitourinary tract cancer, cancer of the kidney adenocarcinoma, Wilm's tumor (nephroblastoma), lymphoma, leukemia, cancer of the bladder, cancer of the urethra, squamous cell carcinoma, transitional cell carcinoma, cancer of the prostate, cancer of the testis, seminoma, teratoma, embryonal carcinoma, teratocarcinoma, choriocarcinoma, sarcoma, interstitial cell carcinoma, fibroma, fibroadenoma, adenomatoid tumors, lipoma, liver cancer, hepatoma hepatocellular carcinoma, cholangiocarcinoma, hepatoblastoma, angiosarcoma, hepatocellular adenoma, hemangioma, bone cancer, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochrondroma (osteocartilaginous exostoses), benign chondroma, chondroblastoma, chondromyxofibroma, osteoid osteoma giant cell tumor, nervous system cancer, cancer of the skull, osteoma, hemangioma, granuloma, xanthoma, osteitis deformans, cancer of the meninges meningioma, meningiosarcoma, gliomatosis, cancer of the brain, astrocytoma, medulloblastoma, glioma, ependymoma, germinoma (pinealoma), glioblastoma multiforme, oligodendroglioma, schwannoma, retinoblastoma, congenital tumors, cancer of the spinal cord, neurofibroma, meningioma, glioma, sarcoma, gynecological cancer, cancer of the uterus, endometrial carcinoma, cancer of the cervix, cervical carcinoma, pre tumor cervical dysplasia, cancer of the ovaries, ovarian carcinoma, serous cystadenocarcinoma, mucinous cystadenocarcinoma, unclassified carcinoma, granulosa-theca cell tumor, Sertoli Leydig cell tumor, dysgerminoma, malignant teratoma, cancer of the vulva, squamous cell carcinoma, intraepithelial carcinoma, adenocarcinoma, fibrosarcoma, melanoma, cancer of the vagina, clear cell carcinoma, squamous cell carcinoma, botryoid sarcoma, embryonal rhabdomyosarcoma, cancer of the fallopian tubes, hematologic cancer, cancer of the blood, acute myeloid leukemia (AML), chronic myeloid leukemia (CML), acute lymphoblastic leukemia (ALL), chronic lymphoblastic leukemia, chronic lymphocytic leukemia, myeloproliferative diseases, multiple myeloma, myelodysplastic syndrome, Hodgkin's lymphoma, non-Hodgkin's lymphoma (malignant lymphoma), Waldenstrom's macroglobulinemia, skin cancer, malignant melanoma, basal cell carcinoma, squamous cell carcinoma, Kaposi's sarcoma, moles dysplastic nevi, lipoma, angioma, dermatofibroma, keloids, psoriasis, adrenal gland cancer, and neuroblastoma.

As used herein, an "effective amount," "therapeutically effective amount," or a "pharmaceutically-effective amount" in reference to the compounds or compositions of the instant invention refers to the amount sufficient to induce a desired biological, pharmacological, or therapeutic outcome in a subject. That result can be reduction, mitigation, delay, shortening the time to resolution of, alleviation of the signs or symptoms of, or exert a medically-beneficial effect upon the underlying pathophysiology or pathogenesis of an expected or observed side-effect, toxicity, disorder or condition, or any other desired alteration of a biological system. In cancer treatment, the result will generally include the reduction, mitigation, limitation, and/or, delay of the deleterious physiological manifestations, growth or metastases of neoplasms.

In some embodiments, the cancer is a solid tumor cancer. In some embodiments, the cancer is a prostate cancer.

In some embodiments, the method of treating a prostate cancer comprises the step of administering to a subject in need thereof of a therapeutically effective amount of a pharmaceutical composition comprising the composition comprising a non-covalently bound complex comprising cabazitaxel and human serum albumin as described herein, prednisone, and a pharmaceutically acceptable carrier.

In some embodiments, the method of treating cancer (e.g. any one of cancers described herein) comprises the step of administering to a subject in need thereof of a therapeutically effective amount of a composition comprising the composition comprising a non-covalently bound complex comprising cabazitaxel and human serum albumin as described herein, and a therapeutically effective amount of at least one inhibitor of the following kinases for the treatment of cancer: PIM, Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGHβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf.

In some embodiments, the method of treating cancer (e.g. any one of cancers described herein) comprises the step of administering to a subject in need thereof of a therapeutically effective amount of a pharmaceutical composition comprising the composition comprising a non-covalently bound complex comprising cabazitaxel and human serum albumin as described herein, and a therapeutically effective amount of at least one anti-cancer drug. Examples of an anti-cancer drug include aberaterone, aberaterone acetate, abarelix, aldesleukin, alemtuzumab, alitretinoin, allopurinol, altretamine, anastrozole, arsenic trioxide, asparaginase, azacitidine, bavituximab, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, cabazitaxel, doxorubicin, dromostanolone propionate, eculizumab, enzalutamide, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate.

In some embodiments, a composition comprising the composition comprising a non-covalently bound complex comprising cabazitaxel and human serum albumin as described herein and an anti-cancer drug are administered simultaneously.

In some embodiments, a composition comprising the composition comprising a non-covalently bound complex comprising cabazitaxel and human serum albumin as described herein and an anti-cancer drug are administered consecutively.

The composition comprising a non-covalently bound complex comprising the cabazitaxel and the human serum albumin described herein can be administered to an individual, such as human, via various routes, such as parenterally, including intravenous, intra-arterial, intraperitoneal, intrapulmonary, oral, inhalation, intravesicular, intramuscular, intra-tracheal, subcutaneous, intraocular, intrathecal, or transdermal. For example, the composition can be administered by inhalation to treat conditions of the respiratory tract. The composition can be used to treat respiratory conditions such as pulmonary fibrosis, broncheolitis obliterans, lung cancer, bronchoalveolar carcinoma, and the like. In some embodiments, the composition described herein is administrated intravenously.

The methods described herein may be performed alone or in conjunction with another therapy, such as surgery, radiation, chemotherapy, immunotherapy, gene therapy, and the like. Additionally, a person having a greater risk of developing the proliferative disease may receive treatments to inhibit and/or delay the development of the disease.

As will be understood by those of ordinary skill in the art, the appropriate doses of cabazitaxel will be approximately those already employed in clinical therapies wherein cabazitaxel is administered alone or in combination with other chemotherapeutic agents. Variation in dosage will likely occur depending on the condition being treated. Appropriate effective doses will also vary, as recognized by those skilled in the art, depending on the severity of the disease, the route of administration, the sex, age and general health condition of the subject, excipient usage, the possibility of co-usage with other therapeutic treatments such as use of other agents, and the judgment of the treating physician. For example, guidance for selecting an effective dose can be determined by reference to the prescribing information for cabazitaxel.

Also, provided herein is a composition consisting essentially of human serum albumin and non-covalently bound complexes of cabazitaxel and human serum albumin, wherein the cabazitaxel and the human serum albumin in the composition have a ratio by weight from about 1:10 to about 1:3000.

Also, provided herein is a composition comprising a non-covalently bound complex consisting essentially of the cabazitaxel and the human serum albumin, wherein the cabazitaxel and the human serum albumin in the composition have a ratio by weight from about 1:10 to about 1:3000.

Also, provided herein is a composition comprising cabazitaxel and human serum albumin, wherein the cabazitaxel and the human serum albumin in the composition have a ratio by weight from about 1:10 to about 1:3000, wherein the composition is a clear aqueous solution when the composition is dissolved in an aqueous solvent, and wherein the composition has a solubility in an aqueous solution of at least 10 mg/mL. In some embodiments, the composition has a solubility in an aqueous solution of about 10 mg/mL, about 20 mg/mL, about 30 mg/mL, about 40 mg/mL, about 50 mg/mL, 60 mg/mL, about 70 mg/mL, about 80 mg/mL, about 90 mg/mL, about 100 mg/mL, about 150 mg/mL, or about 200 mg/mL. In some embodiments, the pH of the composition is neutral (e.g., pH of the composition is from about 5 to about 8, from about 5.5 to about 7.5, or from about 6 to about 7, or the pH of the composition is about 5, about 5.5, about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8).

In some embodiments, the cabazitaxel and the human serum albumin in the composition have a ratio by weight from about 1:50 to about 1:1500, from about 1:100 to about 1:800, from about 1:150 to about 1:600, or from about 1:200 to about 1:500. In some embodiments, the cabazitaxel and the human serum albumin in the composition have a ratio by weight from about 1:100 to about 1:2000. In some embodiments, the cabazitaxel and the human serum albumin in the composition have a ratio by weight from about 1:150 to about 1:1000. In some embodiments, the cabazitaxel and the human serum albumin in the composition have a ratio by weight from about 1:150 to about 1:800. In some embodiments, the cabazitaxel and the human serum albumin in the composition have a ratio by weight from about 1:150 to about 1:600. In some embodiments, the cabazitaxel and the human serum albumin in the composition have a ratio by weight from about 1:150 to about 1:500. In some embodiments, the cabazitaxel and the human serum albumin in the composition have a ratio by weight from about 1:150 to about 1:400. In some embodiments, the cabazitaxel and the human serum albumin in the composition have a ratio by weight from about 1:200 to about 1:1000. In some embodiments, the cabazitaxel and the human serum albumin in the composition have a ratio by weight from about 1:200 to about 1:800. In some embodiments, the cabazitaxel and the human serum albumin in the composition have a ratio by weight from about 1:200 to about 1:600. In some embodiments, the cabazitaxel and the human serum albumin in the composition have a ratio by weight from about 1:200 to about 1:500. In some embodiments, the cabazitaxel and the human serum albumin in the composition have a ratio by weight from about 1:200 to about 1:400. In some embodiments, the cabazitaxel and the human serum albumin in the composition have a ratio by weight from about 1:250 to about 1:1000. In some embodiments, the cabazitaxel and the human serum albumin in the composition have a ratio by weight from about 1:250 to about 1:800. In some embodiments, the cabazitaxel and the human serum albumin in the composition have a ratio by weight from about 1:250 to about 1:600. In some embodiments, the cabazitaxel and the human serum albumin in the composition have a ratio by weight from about 1:250 to about 1:500. In some embodiments, the cabazitaxel and the human serum albumin in the composition have a ratio by weight from about 1:250 to about 1:400. In some embodiments, the cabazitaxel and the human serum albumin in the composition have a ratio by weight from about 1:300 to about 1:600. In some embodiments, the cabazitaxel and the human serum albumin in the composition have a ratio by weight from about 1:300 to about 1:400. In some embodiments, the cabazitaxel and the human serum albumin in the composition have a ratio by weight from about 1:100 to about 1:1000. In some embodiments, the cabazitaxel and the human serum albumin in the composition have a ratio by weight from about 1:220 to about 1:600. In some embodiments, the cabazitaxel and the human serum albumin in the composition have a ratio by weight of about 1:200, 1:210, 1:220, about 1:230, about 1:240, about 1:250, about 1:260, about 1:270, about 1:280, about 1:290, about 1:300, about 1:310, about 1:320, about 1:330, about 1:340, about 1:350, about 1:360, about 1:370, about 1:380, about 1:390, about 1:400, about 1:450, about 1:460, about 1:500 or about 1:600.

In some embodiments, the human serum albumin is a native human serum albumin. In some embodiments, the human serum albumin is a recombinant human serum albumin. In some embodiments, the human serum albumin is a fatty acid free human serum albumin. In some embodiments, the human serum albumin is essentially fatty acid free. In some embodiments, the human serum albumin contains no more than two moles of fatty acids bound to one mole of human serum albumin. In some embodiments, the human serum albumin contains no more than one mole of fatty acids bound to one mole of human serum albumin. In some embodiments, human serum albumin contains no more than 0.5 moles of fatty acids bound to one mole of human serum albumin. In some embodiments, the human serum albumin contains no more than 0.1 moles of fatty acids bound to one mole of human serum albumin. In some embodiments, the human serum albumin contains no more than 0.05 moles of fatty acids bound to one mole of human serum albumin. In some embodiments, the human serum albumin contains no more than 0.01 moles of fatty acids bound to one mole of human serum albumin. In some embodiments, the human serum albumin contains no more than 0.001 moles of fatty acids bound to one mole of human serum albumin. In some embodiments, the human serum albumin contains no more than 0.0005 moles of fatty acids bound to one mole of human serum albumin. In some embodiments, the human serum albumin contains no more than 0.0001 moles of fatty acids bound to one mole of human serum albumin.

In some embodiments, the cabazitaxel can be a pharmaceutically acceptable salt of cabazitaxel. In some embodiments, the cabazitaxel can be any one of crystal forms, amorphous forms, solvates and hydrates as described herein.

In some embodiments, provided herein is a composition comprising cabazitaxel and human serum albumin, wherein the cabazitaxel and the human serum albumin in the composition have a ratio by weight from about 1:150 to about 1:1000, wherein the composition is a clear aqueous solution when the composition is dissolved in an aqueous solvent, wherein the composition has a solubility in an aqueous solution of at least 10 mg/mL, and wherein the clear aqueous solution has pH value from about 5 to about 8.

In some embodiments, provided herein is a composition comprising cabazitaxel and human serum albumin, wherein the cabazitaxel and the human serum albumin in the composition have a ratio by weight from about 1:150 to about 1:1000, wherein the composition is a clear aqueous solution when the composition is dissolved in an aqueous solvent, wherein the composition has a solubility in an aqueous solution of at least 10 mg/mL, and wherein the clear aqueous solution has pH value from about 6 to about 7.5.

In some embodiments, provided herein is a composition comprising cabazitaxel and human serum albumin, wherein the cabazitaxel and the human serum albumin in the composition have a ratio by weight from about 1:200 to about 1:600, wherein the composition is a clear aqueous solution when the composition is dissolved in an aqueous solvent, wherein the composition has a solubility in an aqueous solution of at least 10 mg/mL, and wherein the clear aqueous solution has pH value from about 5 to about 8.

In some embodiments, provided herein is a composition comprising cabazitaxel and human serum albumin, wherein the cabazitaxel and the human serum albumin in the composition have a ratio by weight from about 1:200 to about 1:600, wherein the composition is a clear aqueous solution when the composition is dissolved in an aqueous solvent, wherein the composition has a solubility in an aqueous solution of at least 10 mg/mL, and wherein the clear aqueous solution has pH value from about 6 to about 7.5.

In some embodiments, provided herein is a composition comprising cabazitaxel and human serum albumin, wherein the cabazitaxel and the human serum albumin in the composition have a ratio by weight from about 1:250 to about 1:500, wherein the composition is a clear aqueous solution when the composition is dissolved in an aqueous solvent, wherein the composition has a solubility in an aqueous solution of at least 10 mg/mL, and wherein the clear aqueous solution has pH value from about 5 to about 8.

In some embodiments, provided herein is a composition comprising cabazitaxel and human serum albumin, wherein the cabazitaxel and the human serum albumin in the composition have a ratio by weight from about 1:250 to about 1:500, wherein the composition is a clear aqueous solution when the composition is dissolved in an aqueous solvent, wherein the composition has a solubility in an aqueous solution of at least 10 mg/mL, and wherein the clear aqueous solution has pH value from about 6 to about 7.5.

In some embodiments, the composition is a clear aqueous solution when the composition is dissolved in water. In some embodiments, the composition is a clear aqueous solution when the composition is dissolved in 0.9% saline. In some embodiments, the composition is a clear aqueous solution when the composition is dissolved in 5% dextrose solution.

In some embodiments, the composition forms a clear aqueous solution, when the composition is dissolved in an aqueous solvent, wherein the clear aqueous solution has pH value from about 5 to about 8. In some embodiments, the composition forms a clear aqueous solution, when the composition is dissolved in an aqueous solvent, wherein the clear aqueous solution has pH value from about 5.5 to about 7.8. In some embodiments, the composition forms a clear aqueous solution, when the composition is dissolved in an aqueous solvent, wherein the clear aqueous solution has pH value from about 6 to about 7.5. In some embodiments, the composition forms a clear aqueous solution, when the composition is dissolved in an aqueous solvent, wherein the clear aqueous solution has pH value from about 6.5 to about 7.5. In some embodiments, the composition forms a clear aqueous solvent, when the composition is dissolved in an aqueous solution, wherein the clear aqueous solution has pH value from about 6 to about 6.5. In some embodiments, the composition forms a clear aqueous solution, when the composition is dissolved in an aqueous solvent, wherein the clear aqueous solution has pH value from about 6.5 to about 7. In some embodiments, the composition forms a clear aqueous solution, when the composition is dissolved in an aqueous solvent, wherein the clear aqueous solution has pH value from about 7 to about 7.5. In some embodiments, the composition forms a clear aqueous solution, when the composition is dissolved in an aqueous solvent, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5. In some embodiments, the aqueous solution is substantially free of solvent other than water. In some embodiments, the aqueous solution is free of solvent other than water.

In some embodiments, provided herein is a composition comprising cabazitaxel and human serum albumin, wherein the cabazitaxel and the human serum albumin in the composition have a ratio by weight from about 1:200 to about 1:600, wherein the composition is a clear aqueous solution when the composition is dissolved in an aqueous solvent, wherein the composition has a solubility in an aqueous solution of at least 10 mg/mL, and wherein the clear aqueous solution has pH value from about 5 to about 8, and wherein the clear aqueous solution is substantially free of solvent other than water. In some embodiments, provided herein is a composition comprising cabazitaxel and human serum albumin, wherein the cabazitaxel and the human serum albumin in the composition have a ratio by weight from about 1:200 to about 1:600, wherein the composition is a clear aqueous solution when the composition is dissolved in an aqueous solvent, wherein the composition has a solubility in an aqueous solution of at least 10 mg/mL, and wherein the clear aqueous solution has pH value from about 5 to about 8, and wherein the clear aqueous solution is free of solvent other than water.

In some embodiments, provided herein is a composition comprising cabazitaxel and human serum albumin, wherein the cabazitaxel and the human serum albumin in the composition have a ratio by weight from about 1:200 to about 1:600, wherein the composition is a clear aqueous solution when the composition is dissolved in an aqueous solvent, wherein the composition has a solubility in an aqueous solution of at least 10 mg/mL, and wherein the clear aqueous solution has pH value from about 6 to about 7.5, and wherein the clear aqueous solution is substantially free of solvent other than water. In some embodiments, provided herein is a composition comprising cabazitaxel and human serum albumin, wherein the cabazitaxel and the human serum albumin in the composition have a ratio by weight from about 1:200 to about 1:600, wherein the composition is a clear aqueous solution when the composition is dissolved in an aqueous solvent, wherein the composition has a solubility in an aqueous solution of at least 10 mg/mL, and wherein the clear aqueous solution has pH value from about 6 to about 7.5, and wherein the clear aqueous solution is free of solvent other than water.

In some embodiments, provided herein is a composition comprising cabazitaxel and human serum albumin, wherein the cabazitaxel and the human serum albumin in the composition have a ratio by weight from about 1:250 to about 1:500, wherein the composition is a clear aqueous solution when the composition is dissolved in an aqueous solvent, wherein the composition has a solubility in an aqueous solution of at least 10 mg/mL, and wherein the clear aqueous solution has pH value from about 5 to about 8, and wherein the clear aqueous solution is substantially free of solvent other than water. In some embodiments, provided herein is a composition comprising cabazitaxel and human serum albumin, wherein the cabazitaxel and the human serum albumin in the composition have a ratio by weight from about 1:250 to about 1:500, wherein the composition is a clear aqueous solution when the composition is dissolved in an aqueous solvent, wherein the composition has a solubility in an aqueous solution of at least 10 mg/mL, and wherein the clear aqueous solution has pH value from about 5 to about 8, and wherein the clear aqueous solution is free of solvent other than water.

In some embodiments, provided herein is a composition comprising cabazitaxel and human serum albumin, wherein the cabazitaxel and the human serum albumin in the composition have a ratio by weight from about 1:250 to about 1:500, wherein the composition is a clear aqueous solution when the composition is dissolved in an aqueous solvent, wherein the composition has a solubility in an aqueous solution of at least 10 mg/mL, and wherein the clear aqueous solution has pH value from about 6 to about 7.5, and wherein the clear aqueous solution is substantially free of solvent other than water. In some embodiments, provided herein is a composition comprising cabazitaxel and human serum albumin, wherein the cabazitaxel and the human serum albumin in the composition have a ratio by weight from about 1:250 to about 1:500, wherein the composition is a clear aqueous solution when the composition is dissolved in an aqueous solvent, wherein the composition has a solubility in an aqueous solution of at least 10 mg/mL, and wherein the clear aqueous solution has pH value from about 6 to about 7.5, and wherein the clear aqueous solution is free of solvent other than water.

In some embodiments, the composition forms a clear aqueous solution, when the composition is dissolved in water, wherein the clear aqueous solution has pH value from about 5 to about 8. In some embodiments, the composition forms a clear aqueous solution, when the composition is dissolved in water, wherein the clear aqueous solution has pH value from about 5.5 to about 7.8. In some embodiments, the composition forms a clear aqueous solution, when the composition is dissolved in water, wherein the clear aqueous solution has pH value from about 6 to about 7.5. In some embodiments, the composition forms a clear aqueous solution, when the composition is dissolved in water, wherein the clear aqueous solution has pH value from about 6.5 to about 7.5. In some embodiments, the composition forms a clear aqueous solution, when the composition is dissolved in water, wherein the clear aqueous solution has pH value from about 6 to about 6.5. In some embodiments, the composition forms a clear aqueous solution, when the composition is dissolved in water, wherein the clear aqueous solution has pH value from about 6.5 to about 7. In some embodiments, the composition forms a clear aqueous solution, when the composition is dissolved in water, wherein the clear aqueous solution has pH value from about 7 to about 7.5. In some embodiments, the composition forms a clear aqueous solution, when the composition is dissolved in water, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5.

In some embodiments, the composition forms a clear aqueous solution, when the composition is dissolved in 0.9% saline, wherein the clear aqueous solution has pH value from about 5 to about 8. In some embodiments, the composition forms a clear aqueous solution, when the composition is dissolved in 0.9% saline, wherein the clear aqueous solution has pH value from about 5.5 to about 7.8. In some embodiments, the composition forms a clear aqueous solution, when the composition is dissolved in 0.9% saline, wherein the clear aqueous solution has pH value from about 6 to about 7.5. In some embodiments, the composition forms a clear aqueous solution, when the composition is dissolved in 0.9% saline, wherein the clear aqueous solution has pH value from about 6.5 to about 7.5. In some embodiments, the composition forms a clear aqueous solution, when the composition is dissolved in 0.9% saline, wherein the clear aqueous solution has pH value from about 6 to about 6.5. In some embodiments, the composition forms a clear aqueous solution, when the composition is dissolved in 0.9% saline, wherein the clear aqueous solution has pH value from about 6.5 to about 7. In some embodiments, the composition forms a clear aqueous solution, when the composition is dissolved in 0.9% saline, wherein the clear aqueous solution has pH value from about 7 to about 7.5. In some embodiments, the composition forms a clear aqueous solution, when the composition is dissolved in 0.9% saline, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5.

In some embodiments, the composition forms a clear aqueous solution, when the composition is dissolved in 5% dextrose solution, wherein the clear aqueous solution has pH value from about 5 to about 8. In some embodiments, the composition forms a clear aqueous solution, when the composition is dissolved in 5% dextrose solution, wherein the clear aqueous solution has pH value from about 5.5 to about 7.8. In some embodiments, the composition forms a clear aqueous solution, when the composition is dissolved in 5% dextrose solution, wherein the clear aqueous solution has pH value from about 6 to about 7.5. In some embodiments, the composition forms a clear aqueous solution, when the composition is dissolved in 5% dextrose solution, wherein the clear aqueous solution has pH value from about 6.5 to about 7.5. In some embodiments, the composition forms a clear aqueous solution, when the composition is dissolved in 5% dextrose solution, wherein the clear aqueous solution has pH value from about 6 to about 6.5. In some embodiments, the composition forms a clear aqueous solution, when the composition is dissolved in 5% dextrose solution, wherein the clear aqueous solution has pH value from about 6.5 to about 7. In some embodiments, the composition forms a clear aqueous solution, when the composition is dissolved in 5% dextrose solution, wherein the clear aqueous solution has pH value from about 7 to about 7.5. In some embodiments, the composition forms a clear aqueous solution, when the composition is dissolved in 5% dextrose solution, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5.

In some embodiments, the composition is a clear aqueous solution when the composition is dissolved in an aqueous solvent (e.g. water, 0.9% saline, or 5% dextrose solution), wherein after the clear aqueous solution is filtered by a 0.22 micron filter, the amount of cabazitaxel in the filtered aqueous solution is at least 95% of the total amount of cabazitaxel in the aqueous solution before the filtration. In some embodiments, the composition is a clear aqueous solution when the composition is dissolved in an aqueous solvent (e.g. water, 0.9% saline, or 5% dextrose solution), wherein after the clear aqueous solution is filtered by a 0.22 micron filter, the amount of cabazitaxel in the filtered aqueous solution is at least 96% of the total amount of cabazitaxel in the aqueous solution before the filtration. In some embodiments, the composition is a clear aqueous solution when the composition is dissolved in an aqueous solvent (e.g. water, 0.9% saline, or 5% dextrose solution), wherein after the clear aqueous solution is filtered by a 0.22 micron filter, the amount of cabazitaxel in the filtered aqueous solution is at least 97% of the total amount of cabazitaxel in the aqueous solution before the filtration. In some embodiments, the composition is a clear aqueous solution when the composition is dissolved in an aqueous solution (e.g. water, 0.9% saline, or 5% dextrose solution), wherein after the clear aqueous solution is filtered by a 0.22 micron filter, the amount of cabazitaxel in the filtered aqueous solution is at least 98% of the total amount of cabazitaxel in the aqueous solution before the filtration. In some embodiments, the composition is a clear aqueous solution when the composition is dissolved in an aqueous solution (e.g. water, 0.9% saline, or 5% dextrose solution), wherein after the clear aqueous solution is filtered by a 0.22 micron filter, the amount of cabazitaxel in the filtered aqueous solution is at least 99% of the total amount of cabazitaxel in the aqueous solution before the filtration. In some embodiments, the composition is a clear aqueous solution when the composition is dissolved in an aqueous solution (e.g. water, 0.9% saline, or 5% dextrose solution), wherein after the clear aqueous solution is filtered by a 0.22 micron filter, the amount of cabazitaxel in the filtered aqueous solution is at least 99.5% of the total amount of cabazitaxel in the aqueous solution before the filtration. In some embodiments, the aqueous solution is free of solvent other than water. In some embodiments, the aqueous solution is substantially free of solvent other than water.

In some embodiments, the composition is a clear aqueous solution when the composition is dissolved in an aqueous solution, wherein after the clear aqueous solution is filtered by a 0.22 micron filter, the amount of cabazitaxel in the filtered aqueous solution is at least 95%, 96%, 97%, 98%, 99%, or 99.5% of the total amount of cabazitaxel in the aqueous solution before the filtration, wherein the clear aqueous solution has pH value from about 5 to about 8, and wherein the clear aqueous solution is substantially free of solvent other than water. In some embodiments, the composition is a clear aqueous solution when the composition is dissolved in an aqueous solution, wherein after the clear aqueous solution is filtered by a 0.22 micron filter, the amount of cabazitaxel in the filtered aqueous solution is at least 95%, 96%, 97%, 98%, 99%, or 99.5% of the total amount of cabazitaxel in the aqueous solution before the filtration, wherein the clear aqueous solution has pH value from about 6 to about 7.5, and wherein the clear aqueous solution is substantially free of solvent other than water. In some embodiments, the composition is a clear aqueous solution when the composition is dissolved in an aqueous solution, wherein after the clear aqueous solution is filtered by a 0.22 micron filter, the amount of cabazitaxel in the filtered aqueous solution is at least 95%, 96%, 97%, 98%, 99%, or 99.5% of the total amount of cabazitaxel in the aqueous solution before the filtration, wherein the clear aqueous solution has pH value from about 5 to about 8, and wherein the clear aqueous solution is free of solvent other than water. In some embodiments, the composition is a clear aqueous solution when the composition is dissolved in an aqueous solution, wherein after the clear aqueous solution is filtered by a 0.22 micron filter, the amount of cabazitaxel in the filtered aqueous solution is at least 95%, 96%, 97%, 98%, 99%, or 99.5% of the total amount of cabazitaxel in the aqueous solution before the filtration, wherein the clear aqueous solution has pH value from about 6 to about 7.5, and wherein the clear aqueous solution is free of solvent other than water.

In some embodiments, the amount of cabazitaxel that is bound to the HSA (e.g., non-covalently) in the aqueous solution (e.g., clear aqueous solution) comprising the composition comprising cabazitaxel and HSA (as described herein) is at least 40%, at least 50%, at least 60%, at least 70%, at least 80%, at least 90%, at least 95%, at least 99%, or about 100% of the total about of cabazitaxel in the aqueous solution.

In some embodiments, the composition is an aqueous solution, wherein after the aqueous solution is filtered by a 0.22 micron filter, the amount of cabazitaxel in the filtered aqueous solution is at least 80% of the total amount of cabazitaxel in the aqueous solution before the filtration. In some embodiments, the composition is an aqueous solution, wherein after the aqueous solution is filtered by a 0.22 micron filter, the amount of cabazitaxel in the filtered aqueous solution is at least 85% of the total amount of cabazitaxel in the aqueous solution before the filtration. In some embodiments, the composition is an aqueous solution, wherein after the aqueous solution is filtered by a 0.22 micron filter, the amount of cabazitaxel in the filtered aqueous solution is at least 90% of the total amount of cabazitaxel in the aqueous solution before the filtration. In some embodiments, the aqueous solution is free of solvent other than water. In some embodiments, the aqueous solution is substantially free of solvent other than water.

In some embodiments, the composition is a clear aqueous solution for at least 1 hour when the composition is dissolved in an aqueous solution (e.g. water, 0.9% saline, or 5% dextrose solution). In some embodiments, the composition is a clear aqueous solution for at least 2 hours when the composition is dissolved in an aqueous solution (e.g. water, 0.9% saline, or 5% dextrose solution). In some embodiments, the composition is a clear aqueous solution for at least 3 hours when the composition is dissolved in an aqueous solution (e.g. water, 0.9% saline, or 5% dextrose solution). In some embodiments, the composition is a clear aqueous solution for at least 4 hours when the composition is dissolved in an aqueous solution (e.g. water, 0.9% saline, or 5% dextrose solution). In some embodiments, the composition is a clear aqueous solution for at least 5 hours when the composition is dissolved in an aqueous solution (e.g. water, 0.9% saline, or 5% dextrose solution). In some embodiments, the composition is a clear aqueous solution for at least 6 hours when the composition is dissolved in an aqueous solution (e.g. water, 0.9% saline, or 5% dextrose solution). In some embodiments, the composition is a clear aqueous solution for at least 8 hours when the composition is dissolved in an aqueous solution (e.g. water, 0.9% saline, or 5% dextrose solution). In some embodiments, the composition is a clear aqueous solution for at least 24 hours when the composition is dissolved in an aqueous solution (e.g. water, 0.9% saline, or 5% dextrose solution). In some embodiments, the composition is a clear aqueous solution for at least 3 days when the composition is dissolved in an aqueous solution (e.g. water, 0.9% saline, or 5% dextrose solution). In some embodiments, the aqueous solution is substantially free of solvent other than water. In some embodiments, the aqueous solution is free of solvent other than water.

In some embodiments, the composition is a solid formulation. For example, the solid formulation can be produced in a uniform manner by lyophilization. A skilled artisan would recognize other methods, such as rotary evaporation, that can also produce solid formulations.

In some embodiments, the composition is an aqueous formulation. In some embodiments, the aqueous formulation is substantially free of solvent other than water. In some embodiments, the aqueous formulation is free of solvent other than water. In some embodiments, the pH of the aqueous formulation (e.g., clear aqueous solution) is neutral (e.g., pH of the composition is from about 5 to about 8, from about 5.5 to about 7.5, or from about 6 to about 7, or the pH od the composition is about 5, about 5.5, about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5 or about 8).

In some embodiments, the aqueous formulation can be free of a surfactant, such as CREMOPHOR® surfactants and Polysorbate 80. In some embodiments, the aqueous formulation can be substantially free of a surfactant, such as CREMOPHOR® surfactants and Polysorbate 80. In some embodiments, the aqueous formulation can be substantially free of a surfactant selected from the group consisting of CREMOPHOR® surfactants and Polysorbate 80.

In some embodiments, the aqueous formulation is a clear aqueous solution. For example, the formulation can be a clear and stable aqueous solution reconstituted from a sterile lyophilized powder. In some embodiments, the aqueous formulation is a clear aqueous solution, wherein the aqueous formulation is substantially free of solvent other than water. In some embodiments, the aqueous formulation is a clear aqueous solution, wherein the aqueous formulation is free of solvent other than water.

In some embodiments, the aqueous formulation is a clear aqueous solution reconstituted from the solid formulation (e.g. the sterile lyophilized powder) in water. In some embodiments, the aqueous formulation is a clear aqueous solution reconstituted from the solid formulation (e.g. the sterile lyophilized powder) in 0.9% saline. In some embodiments, the aqueous formulation is a clear aqueous solution reconstituted from the solid formulation (e.g. the sterile lyophilized powder) in 5% dextrose solution.

In some embodiments, the aqueous formulation is a clear aqueous solution reconstituted from the solid formulation (e.g. the sterile lyophilized powder) in water, wherein the aqueous formulation has pH value from about 5 to about 8. In some embodiments, the aqueous formulation is a clear aqueous solution reconstituted from the solid formulation (e.g. the sterile lyophilized powder) in 0.9% saline, wherein the aqueous formulation has pH value from about 5 to about 8. In some embodiments, the aqueous formulation is a clear aqueous solution reconstituted from the solid formulation (e.g. the sterile lyophilized powder) in 5% dextrose solution, wherein the aqueous formulation has pH value from about 5 to about 8.

In some embodiments, the aqueous formulation is a clear aqueous solution reconstituted from the solid formulation (e.g. the sterile lyophilized powder) in water, wherein the pH of water is about 7, and wherein the aqueous formulation has pH value from about 5 to about 8. In some embodiments, the aqueous formulation is a clear aqueous solution reconstituted from the solid formulation (e.g. the sterile lyophilized powder) in 0.9% saline solution, wherein the pH of 0.9% saline solution is about 5.4, and wherein the aqueous formulation has pH value from about 5 to about 8. In some embodiments, the aqueous formulation is a clear aqueous solution reconstituted from the solid formulation (e.g. the sterile lyophilized powder) in 5% dextrose water solution, wherein the pH of 5% dextrose solution is about 4.4, and wherein the aqueous formulation has pH value from about 5 to about 8. In some aspects of the aforementioned embodiments, the concentration of the reconstituted solid in the aqueous formulation is about 25 mg, about 50 mg, about 75 mg, about 100 mg, about 150 mg or 200 mg per 1 mL of the aqueous solvent. In some aspects of the aforementioned embodiments, the concentration of the reconstituted solid in the aqueous formulation is from about 10 mg to about 200 mg per 1 mL of the aqueous solvent.

In some embodiments, the aqueous formulation is a clear aqueous solution reconstituted from the solid formulation (e.g. the sterile lyophilized powder) in water, wherein the aqueous formulation has pH value from about 6 to about 7.5. In some embodiments, the aqueous formulation is a clear aqueous solution reconstituted from the solid formulation (e.g. the sterile lyophilized powder) in 0.9% saline, wherein the aqueous formulation has pH value from about 6 to about 7.5. In some embodiments, the aqueous formulation is a clear aqueous solution reconstituted from the solid formulation (e.g. the sterile lyophilized powder) in 5% dextrose solution, wherein the aqueous formulation has pH value from about 6 to about 7.5.

In some embodiments, the aqueous formulation is a clear aqueous solution reconstituted from the solid formulation (e.g. the sterile lyophilized powder) in water, wherein the pH of water is about 7, and wherein the aqueous formulation has pH value from about 6 to about 7.5. In some embodiments, the aqueous formulation is a clear aqueous solution reconstituted from the solid formulation (e.g. the sterile lyophilized powder) in 0.9% saline solution, wherein the pH of 0.9% saline solution is about 5.4, and wherein the aqueous formulation has pH value from about 6 to about 7.5. In some embodiments, the aqueous formulation is a clear aqueous solution reconstituted from the solid formulation (e.g. the sterile lyophilized powder) in 5% dextrose water solution, wherein pH of the 5% dextrose solution is about 4.4, and wherein the aqueous formulation has pH value from about 6 to about 7.5.

In some embodiments, the aqueous formulation is a clear aqueous solution reconstituted from the solid formulation (e.g. the sterile lyophilized powder) in water, wherein the pH of water is about 7, and wherein the aqueous formulation has pH value of about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8. In some embodiments, the aqueous formulation is a clear aqueous solution reconstituted from the solid formulation (e.g. the sterile lyophilized powder) in 0.9% saline solution, wherein the pH of 0.9% saline solution is about 5.4, and wherein the aqueous formulation has pH value of about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8. In some embodiments, the aqueous formulation is a clear aqueous solution reconstituted from the solid formulation (e.g. the sterile lyophilized powder) in 5% dextrose water solution, wherein pH of the 5% dextrose solution is about 4.4, and wherein the aqueous formulation has pH value of about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8.

In some embodiments, the aqueous formulation has pH value from about 5 to about 8. In some embodiments, the aqueous formulation has pH value from about 5.5 to about 7.8. In some embodiments, the aqueous formulation has pH value from about 6 to about 7.5. In some embodiments, the aqueous formulation has pH value from about 6.5 to about 7.5. In some embodiments, the aqueous formulation has pH value from about 6 to about 6.5. In some embodiments, the aqueous formulation has pH value from about 6.5 to about 7. In some embodiments, the aqueous formulation has pH value from about 7 to about 7.5. In some embodiments, the aqueous formulation has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5. In some embodiments, the aqueous formulation is substantially free of solvent other than water. In some embodiments, the aqueous formulation is free of solvent other than water.

In some embodiments, the aqueous formulation is a clear aqueous solution, wherein the aqueous formulation has pH value from about 5 to about 8, and wherein the aqueous formulation is substantially free of solvent other than water. In some embodiments, the aqueous formulation is a clear aqueous solution, wherein the aqueous formulation has pH value from about 5 to about 8, and wherein the aqueous formulation is free of solvent other than water. In some embodiments, the aqueous formulation is a clear aqueous solution, wherein the aqueous formulation has pH value from about 5.5 to about 7.8, and wherein the aqueous formulation is substantially free of solvent other than water. In some embodiments, the aqueous formulation is a clear aqueous solution, wherein the aqueous formulation has pH value from about 5.5 to about 7.8, and wherein the aqueous formulation is free of solvent other than water. In some embodiments, the aqueous formulation is a clear aqueous solution, wherein the aqueous formulation has pH value from about 6 to about 7.5, and wherein the aqueous formulation is substantially free of solvent other than water. In some embodiments, the aqueous formulation is a clear aqueous solution, wherein the aqueous formulation has pH value from about 6 to about 7.5, and wherein the aqueous formulation is free of solvent other than water. In some embodiments, the aqueous formulation is a clear aqueous solution, wherein the aqueous formulation has pH value from about 6.5 to about 7.5, and wherein the aqueous formulation is substantially free of solvent other than water. In some embodiments, the aqueous formulation is a clear aqueous solution, wherein the aqueous formulation has pH value from about 6.5 to about 7.5, and wherein the aqueous formulation is free of solvent other than water. In some embodiments, the aqueous formulation is a clear aqueous solution, wherein the aqueous formulation has pH value from about 6 to about 6.5, and wherein the aqueous formulation is substantially free of solvent other than water. In some embodiments, the aqueous formulation is a clear aqueous solution, wherein the aqueous formulation has pH value from about 6 to about 6.5, and wherein the aqueous formulation is free of solvent other than water. In some embodiments, the aqueous formulation is a clear aqueous solution, wherein the aqueous formulation has pH value from about 6.5 to about 7, and wherein the aqueous formulation is substantially free of solvent other than water. In some embodiments, the aqueous formulation is a clear aqueous solution, wherein the aqueous formulation has pH value from about 6.5 to about 7, and wherein the aqueous formulation is free of solvent other than water. In some embodiments, the aqueous formulation is a clear aqueous solution, wherein the aqueous formulation has pH value from about 7 to about 7.5, and wherein the aqueous formulation is substantially free of solvent other than water. In some embodiments, the aqueous formulation is a clear aqueous solution, wherein the aqueous formulation has pH value from about 7 to about 7.5, and wherein the aqueous formulation is free of solvent other than water. In some embodiments, the aqueous formulation is a clear aqueous solution, wherein the aqueous formulation has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5, and wherein the aqueous formulation is substantially free of solvent other than water. In some embodiments, the aqueous formulation is a clear aqueous solution, wherein the aqueous formulation has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5, and wherein the aqueous formulation is free of solvent other than water.

In some embodiments, after the aqueous formulation is filtered by a 0.22 micron filter, the amount of cabazitaxel in the filtered aqueous solution is at least 95% of the total amount of cabazitaxel in the aqueous solution before the filtration. In some embodiments, after the aqueous formulation is filtered by a 0.22 micron filter, the amount of cabazitaxel in the filtered aqueous solution is at least 96% of the total amount of cabazitaxel in the aqueous solution before the filtration. In some embodiments, after the aqueous formulation is filtered by a 0.22 micron filter, the amount of cabazitaxel in the filtered aqueous solution is at least 97% of the total amount of cabazitaxel in the aqueous solution before the filtration. In some embodiments, after the aqueous formulation is filtered by a 0.22 micron filter, the amount of cabazitaxel in the filtered aqueous solution is at least 98% of the total amount of cabazitaxel in the aqueous solution before the filtration. In some embodiments, after the aqueous formulation is filtered by a 0.22 micron filter, the amount of cabazitaxel in the filtered aqueous solution is at least 99% of the total amount of cabazitaxel in the aqueous solution before the filtration. In some embodiments, after the aqueous formulation is filtered by a 0.22 micron filter, the amount of cabazitaxel in the filtered aqueous solution is at least 99.5% of the total amount of cabazitaxel in the aqueous solution before the filtration. In some aspects of these embodiments, the aqueous formulation is filtered by a 0.22-micron filter at a time period selected from 1 hour, 2 hours, 3, hours, 4 hours, 5 hours, 6 hours, 8 hours, 12 hours, 18 hours and 24 hours. In some embodiments, the aqueous formulation is free of solvent other than water. In some embodiments, the aqueous formulation is substantially free of solvent other than water.

In some embodiments, after the aqueous formulation (e.g. a clear aqueous solution) is filtered by a 0.22 micron filter, the amount of cabazitaxel in the filtered aqueous solution is at least 95%, 96%, 97%, 98%, 99%, or 99.5% of the total amount of cabazitaxel in the aqueous solution before filtration, wherein the clear aqueous solution has pH value from about 5 to about 8, and wherein the clear aqueous solution is substantially free of solvent other than water. In some embodiments, after the aqueous formulation (e.g. a clear aqueous solution) is filtered by a 0.22 micron filter, the amount of cabazitaxel in the filtered aqueous solution is at least 95%, 96%, 97%, 98%, 99%, or 99.5% of the total amount of cabazitaxel in the aqueous solution before filtration, wherein the clear aqueous solution has pH value from about 6 to about 7.5, and wherein the clear aqueous solution is substantially free of solvent other than water. In some embodiments, after the aqueous formulation (e.g. a clear aqueous solution) is filtered by a 0.22 micron filter, the amount of cabazitaxel in the filtered aqueous solution is at least 95%, 96%, 97%, 98%, 99%, or 99.5% of the total amount of cabazitaxel in the aqueous solution before filtration, wherein the clear aqueous solution has pH value from about 5 to about 8, and wherein the clear aqueous solution is free of solvent other than water. In some embodiments, after the aqueous formulation (e.g. a clear aqueous solution) is filtered by a 0.22 micron filter, the amount of cabazitaxel in the filtered aqueous solution is at least 95%, 96%, 97%, 98%, 99%, or 99.5% of the total amount of cabazitaxel in the aqueous solution before filtration, wherein the clear aqueous solution has pH value from about 6 to about 7.5, and wherein the clear aqueous solution is free of solvent other than water. In some aspects of these embodiments, the aqueous formulation is filtered by a 0.22-micron filter at a time period selected from 1 hour, 2 hours, 3, hours, 4 hours, 5 hours, 6 hours, 8 hours, 12 hours, 18 hours and 24 hours.

In some embodiments, after the aqueous formulation is filtered by a 0.22 micron filter, the amount of cabazitaxel in the filtered aqueous solution is at least 80% of the total amount of cabazitaxel in the aqueous solution before the filtration. In some embodiments, after the aqueous formulation is filtered by a 0.22 micron filter, the amount of cabazitaxel in the filtered aqueous solution is at least 85% of the total amount of cabazitaxel in the aqueous solution before the filtration. In some embodiments, after the aqueous formulation is filtered by a 0.22 micron filter, the amount of cabazitaxel in the filtered aqueous solution is at least 90% of the total amount of cabazitaxel in the aqueous solution before the filtration. In some aspects of these embodiments, the aqueous formulation is filtered by a 0.22-micron filter at a time period selected from 1 hour, 2 hours, 3, hours, 4 hours, 5 hours, 6 hours, 8 hours, 12 hours, 18 hours and 24 hours. In some embodiments, the aqueous formulation is free of solvent other than water. In some embodiments, the aqueous formulation is substantially free of solvent other than water.

In some embodiments, the aqueous formulation is a clear aqueous solution for at least 1 hour. In some embodiments, the aqueous formulation is a clear aqueous solution for at least 2 hours. In some embodiments, the aqueous formulation is a clear aqueous solution for at least 3 hours. In some embodiments, the aqueous formulation is a clear aqueous solution for at least 4 hours. In some embodiments, the aqueous formulation is a clear aqueous solution for at least 5 hours. In some embodiments, the aqueous formulation is a clear aqueous solution for at least 6 hours. In some embodiments, the aqueous formulation is a clear aqueous solution for at least 8 hours. In some embodiments, the aqueous formulation is a clear aqueous solution for at least 24 hours. In some embodiments, the aqueous formulation is a clear aqueous solution for at least 6 hours at a concentration of from about 5 mg/mL to about 250 mg/mL, from about 10 mg/mL to about 200 mg/mL, from about 25 mg/mL to about 150 mg/mL, from about 10 mg/mL to about 50 mg/mL, from about 50 mg/mL to about 100 mg/mL, from about 100 mg/mL to about 150 mg/mL to about 200 mg/mL, or about 5 mg/mL, about 10 mg/mL, about 20 mg/mL, about 30 mg/mL, about 40 mg/mL, about 50 mg/mL, about 60 mg/mL, about 70 mg/mL, about 80 mg/mL, about 90 mg/mL, or about 100 mg/mL at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 24 hours. In some embodiments, the aqueous formulation is a transparent aqueous solution for at least 24 hours at a concentration of from about 5 mg/mL to about 250 mg/mL, from about 10 mg/mL to about 200 mg/mL, from about 25 mg/mL to about 150 mg/mL, from about 10 mg/mL to about 50 mg/mL, from about 50 mg/mL to about 100 mg/mL, from about 100 mg/mL to about 150 mg/mL to about 200 mg/mL, or about 5 mg/mL, about 10 mg/mL, about 20 mg/mL, about 30 mg/mL, about 40 mg/mL, about 50 mg/mL, about 60 mg/mL, about 70 mg/mL, about 80 mg/mL, about 90 mg/mL, or about 100 mg/mL at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 3 days. In some embodiments, the aqueous formulation is a transparent aqueous solution for at least 3 days when dissolved in an aqueous solution at a concentration of from about 5 mg/mL to about 250 mg/mL, from about 10 mg/mL to about 200 mg/mL, from about 25 mg/mL to about 150 mg/mL, from about 10 mg/mL to about 50 mg/mL, from about 50 mg/mL to about 100 mg/mL, from about 100 mg/mL to about 150 mg/mL, from about 150 mg/mL to about 200 mg/mL, or about 5 mg/mL, about 10 mg/mL, about 20 mg/mL, about 30 mg/mL, about 40 mg/mL, about 50 mg/mL, about 60 mg/mL, about 70 mg/mL, about 80 mg/mL, about 90 mg/mL, or about 100 mg/mL at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is substantially free of solvent other than water. In some embodiments, the aqueous formulation is free of solvent other than water.

Also, provided herein is a pharmaceutical composition comprising the composition comprising the cabazitaxel and the human serum albumin as described herein, and a pharmaceutically acceptable carrier.

In some embodiments, the pharmaceutical composition is free of a surfactant, such as CREMOPHOR® surfactants and Polysorbate 80.

In some embodiments, the pharmaceutical composition is substantially free of a surfactant, such as CREMOPHOR® surfactants and Polysorbate 80.

Also, provided herein is a method of treating a proliferative disease comprising the step of administering to a subject in need thereof a therapeutically effective amount of a pharmaceutical composition comprising the composition comprising the cabazitaxel and the human serum albumin as described herein, and a pharmaceutically acceptable carrier.

Also, provided herein is a method of treating a cancer, the method comprising the step of administering to a subject in need thereof of a therapeutically effective amount of a pharmaceutical composition comprising the composition comprising the cabazitaxel and the human serum albumin as described herein, and a pharmaceutically acceptable carrier.

In some embodiments, the cancer is any one of cancers described herein.

In some embodiments, the cancer is a solid tumor cancer. In some embodiments, the cancer is a prostate cancer.

In some embodiments, the method of treating a prostate cancer comprises the step of administering to a subject in need thereof of a therapeutically effective amount of a pharmaceutical composition comprising the composition comprising the cabazitaxel and the human serum albumin as described herein, prednisone, and a pharmaceutically acceptable carrier.

In some embodiments, the method of treating cancer (e.g. any one of cancers described herein) comprises the step of administering to a subject in need thereof a therapeutically effective amount of a pharmaceutical composition comprising the composition comprising the cabazitaxel and the human serum albumin as described herein and a therapeutically effective amount of at least one inhibitor of the kinases for the treatment of cancer described herein.

In some embodiments, the method of treating cancer (e.g. any one of cancers described herein) comprises the step of administering to a subject in need thereof a therapeutically effective amount of a pharmaceutical composition comprising the composition comprising the cabazitaxel and the human serum albumin as described herein and a therapeutically effective amount of at least one anti-cancer drug described herein.

In some embodiments, a composition comprising the cabazitaxel and the human serum albumin as described herein and an anti-cancer drug are administered simultaneously.

In some embodiments, a composition comprising the cabazitaxel and the human serum albumin as described herein and an anti-cancer drug are administered consecutively.

The compositions comprising the cabazitaxel and the human serum albumin described herein can be administered to an individual, such as human, via various routes, such as parenterally, including intravenous, intra-arterial, intraperitoneal, intrapulmonary, oral, inhalation, intravesicular, intramuscular, intra-tracheal, subcutaneous, intraocular, intrathecal, or transdermal. For example, the composition can be administered by inhalation to treat conditions of the respiratory tract. The composition can be used to treat respiratory conditions such as pulmonary fibrosis, broncheolitis obliterans, lung cancer, bronchoalveolar carcinoma, and the like. In some embodiments, the nanoparticle composition is administrated intravenously.

The methods described herein may be performed alone or in conjunction with another therapy, such as surgery, radiation, chemotherapy, immunotherapy, gene therapy, and the like. Additionally, a person having a greater risk of developing the proliferative disease may receive treatments to inhibit or and/or delay the development of the disease.

As will be understood by those of ordinary skill in the art, the appropriate doses of cabazitaxel will be approximately those already employed in clinical therapies wherein cabazitaxel is administered alone or in combination with other chemotherapeutic agents. Variation in dosage will likely occur depending on the condition being treated. Appropriate effective doses will also vary, as recognized by those skilled in the art, depending on the severity of the disease, the route of administration, the sex, age and general health condition of the subject, excipient usage, the possibility of co-usage with other therapeutic treatments such as use of other agents, and the judgment of the treating physician. For example, guidance for selecting an effective dose can be determined by reference to the prescribing information for cabazitaxel.

Also, provided herein is a composition comprising cabazitaxel and human serum albumin, wherein the cabazitaxel and the human serum albumin in the composition have a ratio by weight from about 1:100 to about 1:3000. In some embodiments, the pH of the composition is neutral (e.g., pH of the composition is from about 5 to about 8, from about 5.5 to about 7.5, or from about 6 to about 7, or the pH of the composition is about 5, about 5.5, about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8).

In some embodiments, the cabazitaxel and the human serum albumin in the composition have a ratio by weight from about 1:100 to about 1:2000. In some embodiments, the cabazitaxel and the human serum albumin in the composition have a ratio by weight from about 1:150 to about 1:1000. In some embodiments, the cabazitaxel and the human serum albumin in the composition have a ratio by weight from about 1:150 to about 1:800. In some embodiments, the cabazitaxel and the human serum albumin in the composition have a ratio by weight from about 1:150 to about 1:600. In some embodiments, the cabazitaxel and the human serum albumin in the composition have a ratio by weight from about 1:150 to about 1:500. In some embodiments, the cabazitaxel and the human serum albumin in the composition have a ratio by weight from about 1:150 to about 1:400. In some embodiments, the cabazitaxel and the human serum albumin in the composition have a ratio by weight from about 1:200 to about 1:1000. In some embodiments, the cabazitaxel and the human serum albumin in the composition have a ratio by weight from about 1:200 to about 1:800. In some embodiments, the cabazitaxel and the human serum albumin in the composition have a ratio by weight from about 1:200 to about 1:600. In some embodiments, the cabazitaxel and the human serum albumin in the composition have a ratio by weight from about 1:200 to about 1:500. In some embodiments, the cabazitaxel and the human serum albumin in the composition have a ratio by weight from about 1:200 to about 1:400. In some embodiments, the cabazitaxel and the human serum albumin in the composition have a ratio by weight from about 1:250 to about 1:1000. In some embodiments, the cabazitaxel and the human serum albumin in the composition have a ratio by weight from about 1:250 to about 1:800. In some embodiments, the cabazitaxel and the human serum albumin in the composition have a ratio by weight from about 1:250 to about 1:600. In some embodiments, the cabazitaxel and the human serum albumin in the composition have a ratio by weight from about 1:250 to about 1:500. In some embodiments, the cabazitaxel and the human serum albumin in the composition have a ratio by weight from about 1:250 to about 1:400. In some embodiments, the cabazitaxel and the human serum albumin in the composition have a ratio by weight from about 1:300 to about 1:600. In some embodiments, the cabazitaxel and the human serum albumin in the composition have a ratio by weight from about 1:300 to about 1:400. In some embodiments, the cabazitaxel and the human serum albumin in the composition have a ratio by weight from about 1:100 to about 1:1000. In some embodiments, the cabazitaxel and the human serum albumin in the composition have a ratio by weight from about 1:220 to about 1:600. In some embodiments, the cabazitaxel and the human serum albumin in the composition have a ratio by weight of about 1:200, 1:210, 1:220, about 1:230, about 1:240, about 1:250, about 1:260, about 1:270, about 1:280, about 1:290, about 1:300, about 1:310, about 1:320, about 1:330, about 1:340, about 1:350, about 1:360, about 1:370, about 1:380, about 1:390, about 1:400, about 1:450, about 1:460, about 1:500 or about 1:600.

In some embodiments, the human serum albumin is a native human serum albumin. In some embodiments, the human serum albumin is a recombinant human serum albumin. In some embodiments, the human serum albumin is a fatty acid free human serum albumin. In some embodiments, the human serum albumin is essentially fatty acid free. In some embodiments, the human serum albumin contains no more than two moles of fatty acids bound to one mole of human serum albumin. In some embodiments, the human serum albumin contains no more than one mole of fatty acids bound to one mole of human serum albumin. In some embodiments, human serum albumin contains no more than 0.5 moles of fatty acids bound to one mole of human serum albumin. In some embodiments, the human serum albumin contains no more than 0.1 moles of fatty acids bound to one mole of human serum albumin. In some embodiments, the human serum albumin contains no more than 0.05 moles of fatty acids bound to one mole of human serum albumin. In some embodiments, the human serum albumin contains no more than 0.01 moles of fatty acids bound to one mole of human serum albumin. In some embodiments, the human serum albumin contains no more than 0.001 moles of fatty acids bound to one mole of human serum albumin. In some embodiments, the human serum albumin contains no more than 0.0005 moles of fatty acids bound to one mole of human serum albumin. In some embodiments, the human serum albumin contains no more than 0.0001 moles of fatty acids bound to one mole of human serum albumin.

In some embodiments, the cabazitaxel can be a pharmaceutically acceptable salt of cabazitaxel. In some embodiments, cabazitaxel can be any one of crystal forms, amorphous forms, solvates and hydrates as described herein.

In some embodiments, the composition is a clear aqueous solution when the composition is dissolved in an aqueous solvent. In some embodiments, the aqueous solution is substantially free of solvent other than water. In some embodiments, the aqueous solution is free of solvent other than water.

In some embodiments, the composition is a clear aqueous solution when the composition is dissolved in water. In some embodiments, the composition is a clear aqueous solution when the composition is dissolved in 0.9% saline. In some embodiments, the composition is a clear aqueous solution when the composition is dissolved in 5% dextrose solution.

As used herein, the term "aqueous solution" refers to a solution, wherein at least one solvent is water and the weight % of water in the mixture of solvents is at least 50%, at least 60%, at least 70% or at least 90%. In some embodiments, aqueous solution is a solution in which water is the only solvent. In some embodiments, aqueous solution is 0.9% saline solution. In some embodiments, aqueous solution is 5% dextrose water solution. In some embodiments, aqueous solution is a buffer (e.g., phosphate buffer or a carbonate buffer). In some embodiments, the buffer is physiological buffer or a pharmaceutically acceptable buffer. In some embodiments, the buffer is any one of buffers described, for example, in Y.-C. Lee et al. International Journal of Pharmaceutics 253 (2003) 111-119, the disclosure of which is incorporated herein by reference in its entirety. In some embodiments, the buffer comprises maleic acid, tartaric acid, lactic acid, citric acid, acetic acid, sodium bicarbonate, sodium phosphate, or mixtures thereof. In some embodiments, the pH range of the buffer is from about 3 to about 9, from about 4 to about 8, from about 5 to about 7, from about 6 to about 7, from about 3 to about 5, from about 3 to about 7, from about 4 to about 6, or from about 6 to about 6. In some embodiments, the pH of the buffer is about 4, about 5, about 6, about 6.4, about 6.5, about 6.6, about 7, about 7.5, or about 8.

As used herein, the term "aqueous solvent" refer to a liquid comprising at least 50%, at least 60%, at least 70%, at least 90% or at least 95% water. In some embodiments, aqueous solvent is water.

As used herein, "substantially free of solvent," in reference to an aqueous solution, refers to an aqueous solution that contains less than 0.5%, by weight, of any non-water solvent. In some embodiments, the aqueous solution contains less than 0.1%, by weight, of any non-water solvent. In some embodiments, the aqueous solution contains less than 0.05%, by weight, of any non-water solvent.

In some embodiments, provided herein is a composition comprising cabazitaxel and human serum albumin, wherein the cabazitaxel and the human serum albumin in the composition have a ratio by weight from about 1:150 to about 1:1000, wherein the composition is a clear aqueous solution when the composition is dissolved in an aqueous solution, and wherein the clear aqueous solution has pH value from about 5 to about 8.

In some embodiments, provided herein is a composition comprising cabazitaxel and human serum albumin, wherein the cabazitaxel and the human serum albumin in the composition have a ratio by weight from about 1:150 to about 1:1000, wherein the composition is a clear aqueous solution when the composition is dissolved in an aqueous solution, and wherein the clear aqueous solution has pH value from about 6 to about 7.5.

In some embodiments, provided herein is a composition comprising cabazitaxel and human serum albumin, wherein the cabazitaxel and the human serum albumin in the composition have a ratio by weight from about 1:200 to about 1:600, wherein the composition is a clear aqueous solution when the composition is dissolved in an aqueous solution, and wherein the clear aqueous solution has pH value from about 5 to about 8.

In some embodiments, provided herein is a composition comprising cabazitaxel and human serum albumin, wherein the cabazitaxel and the human serum albumin in the composition have a ratio by weight from about 1:200 to about 1:600, wherein the composition is a clear aqueous solution when the composition is dissolved in an aqueous solution, and wherein the clear aqueous solution has pH value from about 6 to about 7.5.

In some embodiments, provided herein is a composition comprising cabazitaxel and human serum albumin, wherein the cabazitaxel and the human serum albumin in the composition have a ratio by weight from about 1:250 to about 1:500, wherein the composition is a clear aqueous solution when the composition is dissolved in an aqueous solution, and wherein the clear aqueous solution has pH value from about 5 to about 8.

In some embodiments, provided herein is a composition comprising cabazitaxel and human serum albumin, wherein the cabazitaxel and the human serum albumin in the composition have a ratio by weight from about 1:250 to about 1:500, wherein the composition is a clear aqueous solution when the composition is dissolved in an aqueous solution, and wherein the clear aqueous solution has pH value from about 6 to about 7.5.

In some embodiments, provided herein is a composition comprising cabazitaxel and human serum albumin, wherein the cabazitaxel and the human serum albumin in the composition have a ratio by weight from about 1:150 to about 1:1000, wherein the composition is a clear aqueous solution when the composition is dissolved in an aqueous solution, and wherein the clear aqueous solution has pH value from about 5 to about 8, and wherein the clear aqueous solution is substantially free of solvent other than water. In some embodiments, provided herein is a composition comprising cabazitaxel and human serum albumin, wherein the cabazitaxel and the human serum albumin in the composition have a ratio by weight from about 1:150 to about 1:1000, wherein the composition is a clear aqueous solution when the composition is dissolved in an aqueous solution, and wherein the clear aqueous solution has pH value from about 5 to about 8, and wherein the clear aqueous solution is free of solvent other than water.

In some embodiments, provided herein is a composition comprising cabazitaxel and human serum albumin, wherein the cabazitaxel and the human serum albumin in the composition have a ratio by weight from about 1:200 to about 1:600, wherein the composition is a clear aqueous solution when the composition is dissolved in an aqueous solution, and wherein the clear aqueous solution has pH value from about 5 to about 8, and wherein the clear aqueous solution is substantially free of solvent other than water. In some embodiments, provided herein is a composition comprising cabazitaxel and human serum albumin, wherein the cabazitaxel and the human serum albumin in the composition have a ratio by weight from about 1:200 to about 1:600, wherein the composition is a clear aqueous solution when the composition is dissolved in an aqueous solution, and wherein the clear aqueous solution has pH value from about 5 to about 8, and wherein the clear aqueous solution is free of solvent other than water.

In some embodiments, provided herein is a composition comprising cabazitaxel and human serum albumin, wherein the cabazitaxel and the human serum albumin in the composition have a ratio by weight from about 1:250 to about 1:500, wherein the composition is a clear aqueous solution when the composition is dissolved in an aqueous solution, and wherein the clear aqueous solution has pH value from about 5 to about 8, and wherein the clear aqueous solution is substantially free of solvent other than water. In some embodiments, provided herein is a composition comprising cabazitaxel and human serum albumin, wherein the cabazitaxel and the human serum albumin in the composition have a ratio by weight from about 1:250 to about 1:500, wherein the composition is a clear aqueous solution when the composition is dissolved in an aqueous solution, and wherein the clear aqueous solution has pH value from about 5 to about 8, and wherein the clear aqueous solution is free of solvent other than water.

In some embodiments, provided herein is a composition comprising cabazitaxel and human serum albumin, wherein the cabazitaxel and the human serum albumin in the composition have a ratio by weight from about 1:150 to about 1:1000, wherein the composition is a clear aqueous solution when the composition is dissolved in an aqueous solution, and wherein the clear aqueous solution has pH value from about 6 to about 7.5, and wherein the clear aqueous solution is substantially free of solvent other than water. In some embodiments, provided herein is a composition comprising cabazitaxel and human serum albumin, wherein the cabazitaxel and the human serum albumin in the composition have a ratio by weight from about 1:150 to about 1:1000, wherein the composition is a clear aqueous solution when the composition is dissolved in an aqueous solution, and wherein the clear aqueous solution has pH value from about 6 to about 7.5, and wherein the clear aqueous solution is free of solvent other than water.

In some embodiments, provided herein is a composition comprising cabazitaxel and human serum albumin, wherein the cabazitaxel and the human serum albumin in the composition have a ratio by weight from about 1:200 to about 1:600, wherein the composition is a clear aqueous solution when the composition is dissolved in an aqueous solution, and wherein the clear aqueous solution has pH value from about 6 to about 7.5, and wherein the clear aqueous solution is substantially free of solvent other than water. In some embodiments, provided herein is a composition comprising cabazitaxel and human serum albumin, wherein the cabazitaxel and the human serum albumin in the composition have a ratio by weight from about 1:200 to about 1:600, wherein the composition is a clear aqueous solution when the composition is dissolved in an aqueous solution, and wherein the clear aqueous solution has pH value from about 6 to about 7.5, and wherein the clear aqueous solution is free of solvent other than water.

In some embodiments, provided herein is a composition comprising cabazitaxel and human serum albumin, wherein the cabazitaxel and the human serum albumin in the composition have a ratio by weight from about 1:250 to about 1:500, wherein the composition is a clear aqueous solution when the composition is dissolved in an aqueous solution, and wherein the clear aqueous solution has pH value from about 6 to about 7.5, and wherein the clear aqueous solution is substantially free of solvent other than water. In some embodiments, provided herein is a composition comprising cabazitaxel and human serum albumin, wherein the cabazitaxel and the human serum albumin in the composition have a ratio by weight from about 1:250 to about 1:500, wherein the composition is a clear aqueous solution when the composition is dissolved in an aqueous solution, and wherein the clear aqueous solution has pH value from about 6 to about 7.5, and wherein the clear aqueous solution is free of solvent other than water.

In some embodiments, the composition forms a clear aqueous solution, when the composition is dissolved in an aqueous solvent, wherein the clear aqueous solution has pH value from about 5 to about 8. In some embodiments, the composition forms a clear aqueous solution, when the composition is dissolved in an aqueous solvent, wherein the clear aqueous solution has pH value from about 5.5 to about 7.8. In some embodiments, the composition forms a clear aqueous solution, when the composition is dissolved in an aqueous solvent, wherein the clear aqueous solution has pH value from about 6 to about 7.5. In some embodiments, the composition forms a clear aqueous solution, when the composition is dissolved in an aqueous solvent, wherein the clear aqueous solution has pH value from about 6.5 to about 7.5. In some embodiments, the composition forms a clear aqueous solution, when the composition is dissolved in an aqueous solvent, wherein the clear aqueous solution has pH value from about 6 to about 6.5. In some embodiments, the composition forms a clear aqueous solution, when the composition is dissolved in an aqueous solvent, wherein the clear aqueous solution has pH value from about 6.5 to about 7. In some embodiments, the composition forms a clear aqueous solution, when the composition is dissolved in an aqueous solvent, wherein the clear aqueous solution has pH value from about 7 to about 7.5. In some embodiments, the composition forms a clear aqueous solution, when the composition is dissolved in an aqueous solvent wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5. In some embodiments, the aqueous solution is substantially free of solvent other than water. In some embodiments, the aqueous solution is free of solvent other than water.

In some embodiments, the composition forms a clear aqueous solution, when the composition is dissolved in water, wherein the clear aqueous solution has pH value from about 5 to about 8. In some embodiments, the composition forms a clear aqueous solution, when the composition is dissolved in water, wherein the clear aqueous solution has pH value from about 5.5 to about 7.8. In some embodiments, the composition forms a clear aqueous solution, when the composition is dissolved in water, wherein the clear aqueous solution has pH value from about 6 to about 7.5. In some embodiments, the composition forms a clear aqueous solution, when the composition is dissolved in water, wherein the clear aqueous solution has pH value from about 6.5 to about 7.5. In some embodiments, the composition forms a clear aqueous solution, when the composition is dissolved in water, wherein the clear aqueous solution has pH value from about 6 to about 6.5. In some embodiments, the composition forms a clear aqueous solution, when the composition is dissolved in water, wherein the clear aqueous solution has pH value from about 6.5 to about 7. In some embodiments, the composition forms a clear aqueous solution, when the composition is dissolved in water, wherein the clear aqueous solution has pH value from about 7 to about 7.5. In some embodiments, the composition forms a clear aqueous solution, when the composition is dissolved in water, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5.

In some embodiments, the composition forms a clear aqueous solution, when the composition is dissolved in 0.9% saline, wherein the clear aqueous solution has pH value from about 5 to about 8. In some embodiments, the composition forms a clear aqueous solution, when the composition is dissolved in 0.9% saline, wherein the clear aqueous solution has pH value from about 5.5 to about 7.8. In some embodiments, the composition forms a clear aqueous solution, when the composition is dissolved in 0.9% saline, wherein the clear aqueous solution has pH value from about 6 to about 7.5. In some embodiments, the composition forms a clear aqueous solution, when the composition is dissolved in 0.9% saline, wherein the clear aqueous solution has pH value from about 6.5 to about 7.5. In some embodiments, the composition forms a clear aqueous solution, when the composition is dissolved in 0.9% saline, wherein the clear aqueous solution has pH value from about 6 to about 6.5. In some embodiments, the composition forms a clear aqueous solution, when the composition is dissolved in 0.9% saline, wherein the clear aqueous solution has pH value from about 6.5 to about 7. In some embodiments, the composition forms a clear aqueous solution, when the composition is dissolved in 0.9% saline, wherein the clear aqueous solution has pH value from about 7 to about 7.5. In some embodiments, the composition forms a clear aqueous solution, when the composition is dissolved in 0.9% saline, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5.

In some embodiments, the composition forms a clear aqueous solution, when the composition is dissolved in 5% dextrose solution, wherein the clear aqueous solution has pH value from about 5 to about 8. In some embodiments, the composition forms a clear aqueous solution, when the composition is dissolved in 5% dextrose solution, wherein the clear aqueous solution has pH value from about 5.5 to about 7.8. In some embodiments, the composition forms a clear aqueous solution, when the composition is dissolved in 5% dextrose solution, wherein the clear aqueous solution has pH value from about 6 to about 7.5. In some embodiments, the composition forms a clear aqueous solution, when the composition is dissolved in 5% dextrose solution, wherein the clear aqueous solution has pH value from about 6.5 to about 7.5. In some embodiments, the composition forms a clear aqueous solution, when the composition is dissolved in 5% dextrose solution, wherein the clear aqueous solution has pH value from about 6 to about 6.5. In some embodiments, the composition forms a clear aqueous solution, when the composition is dissolved in 5% dextrose solution, wherein the clear aqueous solution has pH value from about 6.5 to about 7. In some embodiments, the composition forms a clear aqueous solution, when the composition is dissolved in 5% dextrose solution, wherein the clear aqueous solution has pH value from about 7 to about 7.5. In some embodiments, the composition forms a clear aqueous solution, when the composition is dissolved in 5% dextrose solution, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5.

In some embodiments, the composition is a clear aqueous solution when the composition is dissolved in an aqueous solvent (e.g. water, 0.9% saline, or 5% dextrose solution), wherein after the clear aqueous solution is filtered by a 0.22 micron filter, the amount of cabazitaxel in the filtered aqueous solution is at least 95% of the total amount of cabazitaxel in the aqueous solution before the filtration. In some embodiments, the composition is a clear aqueous solution when the composition is dissolved in an aqueous solvent (e.g. water, 0.9% saline, or 5% dextrose solution), wherein after the clear aqueous solution is filtered by a 0.22 micron filter, the amount of cabazitaxel in the filtered aqueous solution is at least 96% of the total amount of cabazitaxel in the aqueous solution before the filtration. In some embodiments, the composition is a clear aqueous solution when the composition is dissolved in an aqueous solvent (e.g. water, 0.9% saline, or 5% dextrose solution), wherein after the clear aqueous solution is filtered by a 0.22 micron filter, the amount of cabazitaxel in the filtered aqueous solution is at least 97% of the total amount of cabazitaxel in the aqueous solution before the filtration. In some embodiments, the composition is a clear aqueous solution when the composition is dissolved in an aqueous solvent (e.g. water, 0.9% saline, or 5% dextrose solution), wherein after the clear aqueous solution is filtered by a 0.22 micron filter, the amount of cabazitaxel in the filtered aqueous solution is at least 98% of the total amount of cabazitaxel in the aqueous solution before the filtration. In some embodiments, the composition is a clear aqueous solution when the composition is dissolved in an aqueous solution (e.g. water, 0.9% saline, or 5% dextrose solution), wherein after the clear aqueous solution is filtered by a 0.22 micron filter, the amount of cabazitaxel in the filtered aqueous solution is at least 99% of the total amount of cabazitaxel in the aqueous solution before the filtration. In some embodiments, the composition is a clear aqueous solution when the composition is dissolved in an aqueous solution (e.g. water, 0.9% saline, or 5% dextrose solution), wherein after the clear aqueous solution is filtered by a 0.22 micron filter, the amount of cabazitaxel in the filtered aqueous solution is at least 99.5% of the total amount of cabazitaxel in the aqueous solution before the filtration. In some embodiments, the aqueous solution is free of solvent other than water. In some embodiments, the aqueous solution is substantially free of solvent other than water.

In some embodiments, the composition is a clear aqueous solution when the composition is dissolved in an aqueous solution, wherein after the clear aqueous solution is filtered by a 0.22 micron filter, the amount of cabazitaxel in the filtered aqueous solution is at least 95%, 96%, 97%, 98%, 99%, or 99.5% of the total amount of cabazitaxel in the aqueous solution before the filtration, wherein the clear aqueous solution has pH value from about 5 to about 8, and wherein the clear aqueous solution is substantially free of solvent other than water. In some embodiments, the composition is a clear aqueous solution when the composition is dissolved in an aqueous solution, wherein after the clear aqueous solution is filtered by a 0.22 micron filter, the amount of cabazitaxel in the filtered aqueous solution is at least 95%, 96%, 97%, 98%, 99%, or 99.5% of the total amount of cabazitaxel in the aqueous solution before the filtration, wherein the clear aqueous solution has pH value from about 6 to about 7.5, and wherein the clear aqueous solution is substantially free of solvent other than water. In some embodiments, the composition is a clear aqueous solution when the composition is dissolved in an aqueous solution, wherein after the clear aqueous solution is filtered by a 0.22 micron filter, the amount of cabazitaxel in the filtered aqueous solution is at least 95%, 96%, 97%, 98%, 99%, or 99.5% of the total amount of cabazitaxel in the aqueous solution before the filtration, wherein the clear aqueous solution has pH value from about 5 to about 8, and wherein the clear aqueous solution is free of solvent other than water. In some embodiments, the composition is a clear aqueous solution when the composition is dissolved in an aqueous solution, wherein after the clear aqueous solution is filtered by a 0.22 micron filter, the amount of cabazitaxel in the filtered aqueous solution is at least 95%, 96%, 97%, 98%, 99%, or 99.5% of the total amount of cabazitaxel in the aqueous solution before the filtration, wherein the clear aqueous solution has pH value from about 6 to about 7.5, and wherein the clear aqueous solution is free of solvent other than water.

In some embodiments, the amount of cabazitaxel that is bound to the HSA (e.g., non-covalently) in the aqueous solution (e.g., clear aqueous solution) comprising the composition comprising cabazitaxel and HSA (as described herein) is at least 40%, at least 50%, at least 60%, at least 70%, at least 80%, at least 90%, at least 95%, at least 99%, or about 100% of the total about of cabazitaxel in the aqueous solution.

In some embodiments, the composition is an aqueous solution, wherein after the aqueous solution is filtered by a 0.22 micron filter, the amount of cabazitaxel in the filtered aqueous solution is at least 80% of the total amount of cabazitaxel in the aqueous solution before the filtration. In some embodiments, the composition is an aqueous solution, wherein after the aqueous solution is filtered by a 0.22 micron filter, the amount of cabazitaxel in the filtered aqueous solution is at least 85% of the total amount of cabazitaxel in the aqueous solution before the filtration. In some embodiments, the composition is an aqueous solution, wherein after the aqueous solution is filtered by a 0.22 micron filter, the amount of cabazitaxel in the filtered aqueous solution is at least 90% of the total amount of cabazitaxel in the aqueous solution before the filtration. In some embodiments, the aqueous solution is free of solvent other than water. In some embodiments, the aqueous solution is substantially free of solvent other than water.

In some embodiments, the composition is a clear aqueous solution for at least 1 hour when the composition is dissolved in an aqueous solution (e.g. water, 0.9% saline, or 5% dextrose solution). In some embodiments, the composition is a clear aqueous solution for at least 2 hours when the composition is dissolved in an aqueous solution (e.g. water, 0.9% saline, or 5% dextrose solution). In some embodiments, the composition is a clear aqueous solution for at least 3 hours when the composition is dissolved in an aqueous solution (e.g. water, 0.9% saline, or 5% dextrose solution). In some embodiments, the composition is a clear aqueous solution for at least 4 hours when the composition is dissolved in an aqueous solution (e.g. water, 0.9% saline, or 5% dextrose solution). In some embodiments, the composition is a clear aqueous solution for at least 5 hours when the composition is dissolved in an aqueous solution (e.g. water, 0.9% saline, or 5% dextrose solution). In some embodiments, the composition is a clear aqueous solution for at least 6 hours when the composition is dissolved in an aqueous solution (e.g. water, 0.9% saline, or 5% dextrose solution). In some embodiments, the composition is a clear aqueous solution for at least 8 hours when the composition is dissolved in an aqueous solution (e.g. water, 0.9% saline, or 5% dextrose solution). In some embodiments, the composition is a clear aqueous solution for at least 24 hours when the composition is dissolved in an aqueous solution (e.g. water, 0.9% saline, or 5% dextrose solution). In some embodiments, the composition is a clear aqueous solution for at least 3 days when the composition is dissolved in an aqueous solution (e.g. water, 0.9% saline, or 5% dextrose solution). In some embodiments, the aqueous solution is substantially free of solvent other than water. In some embodiments, the aqueous solution is free of solvent other than water.

In some embodiments, the composition is a solid formulation. For example, the solid formulation can be produced in a uniform manner by lyophilization. A skilled artisan would recognize other methods, such as rotary evaporation, that can also produce solid formulations.

In some embodiments, the composition is an aqueous formulation. In some embodiments, the aqueous formulation is substantially free of solvent other than water. In some embodiments, the aqueous formulation is free of solvent other than water. In some embodiments, the aqueous formulation includes water and water-miscible organic solvents including at least one of polyethylene glycol 300, polyethylene glycol 400, ethanol, methanol, propylene glycol, glycerin, N-methyl-2-pyrrolidone, dimethylacetamide, and dimethylsulfoxide. For example, the water-miscible organic solvent can include ethanol. In some embodiments, the aqueous formulation includes water and ethanol. In some embodiments, the water-miscible organic solvent can be a mixture of water-miscible organic solvents. In some embodiments, the pH of the aqueous formulation (e.g., clear aqueous solution) is neutral (e.g., pH of the composition is from about 5 to about 8, from about 5.5 to about 7.5, or from about 6 to about 7, or the pH od the composition is about 5, about 5.5, about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5 or about 8).

In some embodiments, the aqueous formulation can be free of a surfactant, such as CREMOPHOR® surfactants and Polysorbate 80. In some embodiments, the aqueous formulation can be substantially free of a surfactant, such as CREMOPHOR® surfactants and Polysorbate 80. In some embodiments, the aqueous formulation can be substantially free of a surfactant selected from the group consisting of CREMOPHOR® surfactants and Polysorbate 80.

As used herein, the term "substantially free of surfactant" refers to a formulation containing less than 0.0005%, less than 0.0003%, or less than 0.0001% of surfactants and/or less than 0.0005%, less than 0.0003%, or less than 0.0001% of surfactant.

In some embodiments, the aqueous formulation is a clear aqueous solution. For example, the formulation can be a clear and stable aqueous solution reconstituted from a sterile lyophilized powder. In some embodiments, the aqueous formulation is a clear aqueous solution, wherein the aqueous formulation is substantially free of solvent other than water. In some embodiments, the aqueous formulation is a clear aqueous solution, wherein the aqueous formulation is free of solvent other than water.

In some embodiments, the aqueous formulation is a clear aqueous solution reconstituted from the solid formulation (e.g. the sterile lyophilized powder) in water. In some embodiments, the aqueous formulation is a clear aqueous solution reconstituted from the solid formulation (e.g. the sterile lyophilized powder) in 0.9% saline. In some embodiments, the aqueous formulation is a clear aqueous solution reconstituted from the solid formulation (e.g. the sterile lyophilized powder) in 5% dextrose solution.

In some embodiments, the aqueous formulation is a clear aqueous solution reconstituted from the solid formulation (e.g. the sterile lyophilized powder) in water, wherein the aqueous formulation has pH value from about 5 to about 8. In some embodiments, the aqueous formulation is a clear aqueous solution reconstituted from the solid formulation (e.g. the sterile lyophilized powder) in 0.9% saline, wherein the aqueous formulation has pH value from about 5 to about 8. In some embodiments, the aqueous formulation is a clear aqueous solution reconstituted from the solid formulation (e.g. the sterile lyophilized powder) in 5% dextrose solution, wherein the aqueous formulation has pH value from about 5 to about 8.

In some embodiments, the aqueous formulation is a clear aqueous solution reconstituted from the solid formulation (e.g. the sterile lyophilized powder) in water, wherein the pH of water is about 7, and wherein the aqueous formulation has pH value from about 5 to about 8. In some embodiments, the aqueous formulation is a clear aqueous solution reconstituted from the solid formulation (e.g. the sterile lyophilized powder) in 0.9% saline solution, wherein the pH of 0.9% saline solution is about 5.4, and wherein the aqueous formulation has pH value from about 5 to about 8. In some embodiments, the aqueous formulation is a clear aqueous solution reconstituted from the solid formulation (e.g. the sterile lyophilized powder) in 5% dextrose water solution, wherein the pH of 5% dextrose solution is about 4.4, and wherein the aqueous formulation has pH value from about 5 to about 8. In some aspects of the aforementioned embodiments, the concentration of the reconstituted solid in the aqueous formulation is about 25 mg, about 50 mg, about 75 mg, about 100 mg, about 150 mg or 200 mg per 1 mL of the aqueous solvent. In some aspects of the aforementioned embodiments, the concentration of the reconstituted solid in the aqueous formulation is from about 10 mg to about 200 mg per 1 mL of the aqueous solvent.

In some embodiments, the aqueous formulation is a clear aqueous solution reconstituted from the solid formulation (e.g. the sterile lyophilized powder) in water, wherein the aqueous formulation has pH value from about 6 to about 7.5. In some embodiments, the aqueous formulation is a clear aqueous solution reconstituted from the solid formulation (e.g. the sterile lyophilized powder) in 0.9% saline, wherein the aqueous formulation has pH value from about 6 to about 7.5. In some embodiments, the aqueous formulation is a clear aqueous solution reconstituted from the solid formulation (e.g. the sterile lyophilized powder) in 5% dextrose solution, wherein the aqueous formulation has pH value from about 6 to about 7.5.

In some embodiments, the aqueous formulation is a clear aqueous solution reconstituted from the solid formulation (e.g. the sterile lyophilized powder) in water, wherein the pH of water is about 7, and wherein the aqueous formulation has pH value from about 6 to about 7.5. In some embodiments, the aqueous formulation is a clear aqueous solution reconstituted from the solid formulation (e.g. the sterile lyophilized powder) in 0.9% saline solution, wherein the pH of 0.9% saline solution is about 5.4, and wherein the aqueous formulation has pH value from about 6 to about 7.5. In some embodiments, the aqueous formulation is a clear aqueous solution reconstituted from the solid formulation (e.g. the sterile lyophilized powder) in 5% dextrose water solution, wherein pH of the 5% dextrose solution is about 4.4, and wherein the aqueous formulation has pH value from about 6 to about 7.5.

In some embodiments, the aqueous formulation is a clear aqueous solution reconstituted from the solid formulation (e.g. the sterile lyophilized powder) in water, wherein the pH of water is about 7, and wherein the aqueous formulation has pH value of about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8. In some embodiments, the aqueous formulation is a clear aqueous solution reconstituted from the solid formulation (e.g. the sterile lyophilized powder) in 0.9% saline solution, wherein the pH of 0.9% saline solution is about 5.4, and wherein the aqueous formulation has pH value of about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8. In some embodiments, the aqueous formulation is a clear aqueous solution reconstituted from the solid formulation (e.g. the sterile lyophilized powder) in 5% dextrose water solution, wherein pH of the 5% dextrose solution is about 4.4, and wherein the aqueous formulation has pH value of about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8.

In some embodiments, the aqueous formulation has pH value from about 5 to about 8. In some embodiments, the aqueous formulation has pH value from about 5.5 to about 7.8. In some embodiments, the aqueous formulation has pH value from about 6 to about 7.5. In some embodiments, the aqueous formulation has pH value from about 6.5 to about 7.5. In some embodiments, the aqueous formulation has pH value from about 6 to about 6.5. In some embodiments, the aqueous formulation has pH value from about 6.5 to about 7. In some embodiments, the aqueous formulation has pH value from about 7 to about 7.5. In some embodiments, the aqueous formulation has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5. In some embodiments, the aqueous formulation is substantially free of solvent other than water. In some embodiments, the aqueous formulation is free of solvent other than water.

In some embodiments, the aqueous formulation is a clear aqueous solution, wherein the aqueous formulation has pH value from about 5 to about 8, and wherein the aqueous formulation is substantially free of solvent other than water. In some embodiments, the aqueous formulation is a clear aqueous solution, wherein the aqueous formulation has pH value from about 5 to about 8, and wherein the aqueous formulation is free of solvent other than water. In some embodiments, the aqueous formulation is a clear aqueous solution, wherein the aqueous formulation has pH value from about 5.5 to about 7.8, and wherein the aqueous formulation is substantially free of solvent other than water. In some embodiments, the aqueous formulation is a clear aqueous solution, wherein the aqueous formulation has pH value from about 5.5 to about 7.8, and wherein the aqueous formulation is free of solvent other than water. In some embodiments, the aqueous formulation is a clear aqueous solution, wherein the aqueous formulation has pH value from about 6 to about 7.5, and wherein the aqueous formulation is substantially free of solvent other than water. In some embodiments, the aqueous formulation is a clear aqueous solution, wherein the aqueous formulation has pH value from about 6 to about 7.5, and wherein the aqueous formulation is free of solvent other than water. In some embodiments, the aqueous formulation is a clear aqueous solution, wherein the aqueous formulation has pH value from about 6.5 to about 7.5, and wherein the aqueous formulation is substantially free of solvent other than water. In some embodiments, the aqueous formulation is a clear aqueous solution, wherein the aqueous formulation has pH value from about 6.5 to about 7.5, and wherein the aqueous formulation is free of solvent other than water. In some embodiments, the aqueous formulation is a clear aqueous solution, wherein the aqueous formulation has pH value from about 6 to about 6.5, and wherein the aqueous formulation is substantially free of solvent other than water. In some embodiments, the aqueous formulation is a clear aqueous solution, wherein the aqueous formulation has pH value from about 6 to about 6.5, and wherein the aqueous formulation is free of solvent other than water. In some embodiments, the aqueous formulation is a clear aqueous solution, wherein the aqueous formulation has pH value from about 6.5 to about 7, and wherein the aqueous formulation is substantially free of solvent other than water. In some embodiments, the aqueous formulation is a clear aqueous solution, wherein the aqueous formulation has pH value from about 6.5 to about 7, and wherein the aqueous formulation is free of solvent other than water. In some embodiments, the aqueous formulation is a clear aqueous solution, wherein the aqueous formulation has pH value from about 7 to about 7.5, and wherein the aqueous formulation is substantially free of solvent other than water. In some embodiments, the aqueous formulation is a clear aqueous solution, wherein the aqueous formulation has pH value from about 7 to about 7.5, and wherein the aqueous formulation is free of solvent other than water. In some embodiments, the aqueous formulation is a clear aqueous solution, wherein the aqueous formulation has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5, and wherein the aqueous formulation is substantially free of solvent other than water. In some embodiments, the aqueous formulation is a clear aqueous solution, wherein the aqueous formulation has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5, and wherein the aqueous formulation is free of solvent other than water.

In some embodiments, after the aqueous formulation is filtered by a 0.22 micron filter, the amount of cabazitaxel in the filtered aqueous solution is at least 95% of the total amount of cabazitaxel in the aqueous solution before the filtration. In some embodiments, after the aqueous formulation is filtered by a 0.22 micron filter, the amount of cabazitaxel in the filtered aqueous solution is at least 96% of the total amount of cabazitaxel in the aqueous solution before the filtration. In some embodiments, after the aqueous formulation is filtered by a 0.22 micron filter, the amount of cabazitaxel in the filtered aqueous solution is at least 97% of the total amount of cabazitaxel in the aqueous solution before the filtration. In some embodiments, after the aqueous formulation is filtered by a 0.22 micron filter, the amount of cabazitaxel in the filtered aqueous solution is at least 98% of the total amount of cabazitaxel in the aqueous solution before the filtration. In some embodiments, after the aqueous formulation is filtered by a 0.22 micron filter, the amount of cabazitaxel in the filtered aqueous solution is at least 99% of the total amount of cabazitaxel in the aqueous solution before the filtration. In some embodiments, after the aqueous formulation is filtered by a 0.22 micron filter, the amount of cabazitaxel in the filtered aqueous solution is at least 99.5% of the total amount of cabazitaxel in the aqueous solution before the filtration. In some aspects of these embodiments, the aqueous formulation is filtered by a 0.22-micron filter at a time period selected from 1 hour, 2 hours, 3, hours, 4 hours, 5 hours, 6 hours, 8 hours, 12 hours, 18 hours and 24 hours. In some embodiments, the aqueous formulation is free of solvent other than water. In some embodiments, the aqueous formulation is substantially free of solvent other than water.

In some embodiments, after the aqueous formulation (e.g. a clear aqueous solution) is filtered by a 0.22 micron filter, the amount of cabazitaxel in the filtered aqueous solution is at least 95%, 96%, 97%, 98%, 99%, or 99.5% of the total amount of cabazitaxel in the aqueous solution before filtration, wherein the clear aqueous solution has pH value from about 5 to about 8, and wherein the clear aqueous solution is substantially free of solvent other than water. In some embodiments, after the aqueous formulation (e.g. a clear aqueous solution) is filtered by a 0.22 micron filter, the amount of cabazitaxel in the filtered aqueous solution is at least 95%, 96%, 97%, 98%, 99%, or 99.5% of the total amount of cabazitaxel in the aqueous solution before filtration, wherein the clear aqueous solution has pH value from about 6 to about 7.5, and wherein the clear aqueous solution is substantially free of solvent other than water. In some embodiments, after the aqueous formulation (e.g. a clear aqueous solution) is filtered by a 0.22 micron filter, the amount of cabazitaxel in the filtered aqueous solution is at least 95%, 96%, 97%, 98%, 99%, or 99.5% of the total amount of cabazitaxel in the aqueous solution before filtration, wherein the clear aqueous solution has pH value from about 5 to about 8, and wherein the clear aqueous solution is free of solvent other than water. In some embodiments, after the aqueous formulation (e.g. a clear aqueous solution) is filtered by a 0.22 micron filter, the amount of cabazitaxel in the filtered aqueous solution is at least 95%, 96%, 97%, 98%, 99%, or 99.5% of the total amount of cabazitaxel in the aqueous solution before filtration, wherein the clear aqueous solution has pH value from about 6 to about 7.5, and wherein the clear aqueous solution is free of solvent other than water. In some aspects of these embodiments, the aqueous formulation is filtered by a 0.22-micron filter at a time period selected from 1 hour, 2 hours, 3, hours, 4 hours, 5 hours, 6 hours, 8 hours, 12 hours, 18 hours and 24 hours.

In some embodiments, after the aqueous formulation is filtered by a 0.22 micron filter, the amount of cabazitaxel in the filtered aqueous solution is at least 80% of the total amount of cabazitaxel in the aqueous solution before the filtration. In some embodiments, after the aqueous formulation is filtered by a 0.22 micron filter, the amount of cabazitaxel in the filtered aqueous solution is at least 85% of the total amount of cabazitaxel in the aqueous solution before the filtration. In some embodiments, after the aqueous formulation is filtered by a 0.22 micron filter, the amount of cabazitaxel in the filtered aqueous solution is at least 90% of the total amount of cabazitaxel in the aqueous solution before the filtration. In some aspects of these embodiments, the aqueous formulation is filtered by a 0.22-micron filter at a time period selected from 1 hour, 2 hours, 3, hours, 4 hours, 5 hours, 6 hours, 8 hours, 12 hours, 18 hours and 24 hours. In some embodiments, the aqueous formulation is free of solvent other than water. In some embodiments, the aqueous formulation is substantially free of solvent other than water.

In some embodiments, when the composition comprising cabazitaxel and HSA as described herein (e.g., sterile solid powder) is dissolved in an aqueous solvent (e.g., water, 0.9% saline or 5% dextrose), the resultant aqueous solution, when filtered using a 0.22 micron filter, comprises at least 99% at the time of preparation, at least 99% after 1 hour, at least 99% after 2 hours, at least 98% after 3 hours, at least 98% after 4 hours, at least 98% after 5 hours, at least 98% after 6 hours, or at least 98% after 24 hours of the amount of cabazitaxel used to prepare the composition.

In some embodiments, when the composition comprising cabazitaxel and HSA as described herein (e.g., sterile solid powder) is dissolved in an aqueous solvent (e.g., water, 0.9% saline or 5% dextrose), the resultant aqueous solution, when filtered using a 0.22 micron filter, comprises at least 99% at the time of preparation, at least 99% after 1 hour, at least 99% after 2 hours, at least 99% after 3 hours, at least 99% after 4 hours, at least 99% after 5 hours, at least 99% after 6 hours, or at least 99% after 24 hours of the amount of cabazitaxel used to prepare the composition.

In some embodiments, when the composition comprising cabazitaxel and HSA as described herein (e.g., sterile solid powder) is dissolved in an aqueous solvent (e.g., water, 0.9% saline or 5% dextrose), the resultant aqueous solution, when filtered using a 0.22 micron filter, comprises at least 98% at the time of preparation, at least 98% after 1 hour, at least 98% after 2 hours, at least 98% after 3 hours, at least 98% after 4 hours, at least 98% after 5 hours, at least 98% after 6 hours, or at least 98% after 24 hours of the amount of cabazitaxel used to prepare the composition.

In some embodiments, when the composition comprising cabazitaxel and HSA as described herein (e.g., sterile solid powder) is dissolved in an aqueous solvent (e.g., water, 0.9% saline or 5% dextrose), the resultant aqueous solution, when filtered using a 0.22 micron filter, comprises at least 97% at the time of preparation, at least 97% after 1 hour, at least 97% after 2 hours, at least 97% after 3 hours, at least 97% after 4 hours, at least 97% after 5 hours, at least 97% after 6 hours, or at least 97% after 24 hours of the amount of cabazitaxel used to prepare the composition.

In some embodiments, when the composition comprising cabazitaxel and HSA as described herein (e.g., sterile solid powder) is dissolved in an aqueous solvent (e.g., water, 0.9% saline or 5% dextrose), the resultant aqueous solution, when filtered using a 0.22 micron filter, comprises at least 96% at the time of preparation, at least 96% after 1 hour, at least 96% after 2 hours, at least 96% after 3 hours, at least 96% after 4 hours, at least 96% after 5 hours, at least 96% after 6 hours, or at least 96% after 24 hours of the amount of cabazitaxel used to prepare the composition.

In some embodiments, when the composition comprising cabazitaxel and HSA as described herein (e.g., sterile solid powder) is dissolved in an aqueous solvent (e.g., water, 0.9% saline or 5% dextrose), the resultant aqueous solution, when filtered using a 0.22 micron filter, comprises at least 95% at the time of preparation, at least 95% after 1 hour, at least 95% after 2 hours, at least 95% after 3 hours, at least 95% after 4 hours, at least 95% after 5 hours, at least 95% after 6 hours, or at least 95% after 24 hours of the amount of cabazitaxel used to prepare the composition.

In some embodiments, the aqueous formulation is a clear aqueous solution for at least 1 hour. In some embodiments, the aqueous formulation is a clear aqueous solution for at least 2 hours. In some embodiments, the aqueous formulation is a clear aqueous solution for at least 3 hours. In some embodiments, the aqueous formulation is a clear aqueous solution for at least 4 hours. In some embodiments, the aqueous formulation is a clear aqueous solution for at least 5 hours. In some embodiments, the aqueous formulation is a clear aqueous solution for at least 6 hours. In some embodiments, the aqueous formulation is a clear aqueous solution for at least 8 hours. In some embodiments, the aqueous formulation is a clear aqueous solution for at least 24 hours. In some embodiments, the aqueous formulation is a clear aqueous solution for at least 6 hours at a concentration of from about 5 mg/mL to about 250 mg/mL, from about 10 mg/mL to about 200 mg/mL, from about 25 mg/mL to about 150 mg/mL, from about 10 mg/mL to about 50 mg/mL, from about 50 mg/mL to about 100 mg/mL, from about 100 mg/mL to about 150 mg/mL, from about 150 mg/mL to about 200 mg/mL, or about 5 mg/mL, about 10 mg/mL, about 20 mg/mL, about 30 mg/mL, about 40 mg/mL, about 50 mg/mL, about 60 mg/mL, about 70 mg/mL, about 80 mg/mL, about 90 mg/mL, or about 100 mg/mL at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 24 hours. In some embodiments, the aqueous formulation is a transparent aqueous solution for at least 24 hours at a concentration of from about 5 mg/mL to about 250 mg/mL, from about 10 mg/mL to about 200 mg/mL, from about 25 mg/mL to about 150 mg/mL, from about 10 mg/mL to about 50 mg/mL, from about 50 mg/mL to about 100 mg/mL, from about 100 mg/mL to about 150 mg/mL, from about 150 mg/mL to about 200 mg/mL, or about 5 mg/mL, about 10 mg/mL, about 20 mg/mL, about 30 mg/mL, about 40 mg/mL, about 50 mg/mL, about 60 mg/mL, about 70 mg/mL, about 80 mg/mL, about 90 mg/mL, or about 100 mg/mL at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 3 days. In some embodiments, the aqueous formulation is a transparent aqueous solution for at least 3 days when dissolved in an aqueous solution at a concentration of from about 5 mg/mL to about 250 mg/mL, from about 10 mg/mL to about 200 mg/mL, from about 25 mg/mL to about 150 mg/mL, from about 10 mg/mL to about 50 mg/mL, from about 50 mg/mL to about 100 mg/mL, from about 100 mg/mL to about 150 mg/mL, from about 150 mg/mL to about 200 mg/mL, or about 5 mg/mL, about 10 mg/mL, about 20 mg/mL, about 30 mg/mL, about 40 mg/mL, about 50 mg/mL, about 60 mg/mL, about 70 mg/mL, about 80 mg/mL, about 90 mg/mL, or about 100 mg/mL at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is substantially free of solvent other than water. In some embodiments, the aqueous formulation is free of solvent other than water.

In some embodiments, after the aqueous formulation is filtered by a 0.22 micron filter, the amount of cabazitaxel in the filtered aqueous solution is at least 95% of the total amount of cabazitaxel in the aqueous solution before the filtration. In some embodiments, after the aqueous formulation is filtered by a 0.22 micron filter, the amount of cabazitaxel in the filtered aqueous solution is at least 96% of the total amount of cabazitaxel in the aqueous solution before the filtration. In some embodiments, after the aqueous formulation is filtered by a 0.22 micron filter, the amount of cabazitaxel in the filtered aqueous solution is at least 97% of the total amount of cabazitaxel in the aqueous solution before the filtration. In some embodiments, after the aqueous formulation is filtered by a 0.22 micron filter, the amount of cabazitaxel in the filtered aqueous solution is at least 98% of the total amount of cabazitaxel in the aqueous solution before the filtration. In some embodiments, after the aqueous formulation is filtered by a 0.22 micron filter, the amount of cabazitaxel in the filtered aqueous solution is at least 99% of the total amount of cabazitaxel in the aqueous solution before the filtration. In some embodiments, after the aqueous formulation is filtered by a 0.22 micron filter, the amount of cabazitaxel in the filtered aqueous solution is at least 99.5% of the total amount of cabazitaxel in the aqueous solution before the filtration. In some aspects of these embodiments, the aqueous formulation is filtered by a 0.22-micron filter at a time period selected from 1 hour, 2 hours, 3, hours, 4 hours, 5 hours, 6 hours, 8 hours, 12 hours, 18 hours and 24 hours. In some embodiments, the aqueous formulation is free of solvent other than water. In some embodiments, the aqueous formulation is substantially free of solvent other than water.

In some embodiments, after the aqueous formulation (e.g. a clear aqueous solution) is filtered by a 0.22 micron filter, the amount of cabazitaxel in the filtered aqueous solution is at least 95%, 96%, 97%, 98%, 99%, or 99.5% of the total amount of cabazitaxel in the aqueous solution before filtration, wherein the clear aqueous solution has pH value from about 5 to about 8, and wherein the clear aqueous solution is substantially free of solvent other than water. In some embodiments, after the aqueous formulation (e.g. a clear aqueous solution) is filtered by a 0.22 micron filter, the amount of cabazitaxel in the filtered aqueous solution is at least 95%, 96%, 97%, 98%, 99%, or 99.5% of the total amount of cabazitaxel in the aqueous solution before filtration, wherein the clear aqueous solution has pH value from about 6 to about 7.5, and wherein the clear aqueous solution is substantially free of solvent other than water. In some embodiments, after the aqueous formulation (e.g. a clear aqueous solution) is filtered by a 0.22 micron filter, the amount of cabazitaxel in the filtered aqueous solution is at least 95%, 96%, 97%, 98%, 99%, or 99.5% of the total amount of cabazitaxel in the aqueous solution before filtration, wherein the clear aqueous solution has pH value from about 5 to about 8, and wherein the clear aqueous solution is free of solvent other than water. In some embodiments, after the aqueous formulation (e.g. a clear aqueous solution) is filtered by a 0.22 micron filter, the amount of cabazitaxel in the filtered aqueous solution is at least 95%, 96%, 97%, 98%, 99%, or 99.5% of the total amount of cabazitaxel in the aqueous solution before filtration, wherein the clear aqueous solution has pH value from about 6 to about 7.5, and wherein the clear aqueous solution is free of solvent other than water. In some aspects of these embodiments, the aqueous formulation is filtered by a 0.22-micron filter at a time period selected from 1 hour, 2 hours, 3, hours, 4 hours, 5 hours, 6 hours, 8 hours, 12 hours, 18 hours and 24 hours.

In some embodiments, after the aqueous formulation is filtered by a 0.22 micron filter, the amount of cabazitaxel in the filtered aqueous solution is at least 80% of the total amount of cabazitaxel in the aqueous solution before the filtration. In some embodiments, after the aqueous formulation is filtered by a 0.22 micron filter, the amount of cabazitaxel in the filtered aqueous solution is at least 85% of the total amount of cabazitaxel in the aqueous solution before the filtration. In some embodiments, after the aqueous formulation is filtered by a 0.22 micron filter, the amount of cabazitaxel in the filtered aqueous solution is at least 90% of the total amount of cabazitaxel in the aqueous solution before the filtration. In some aspects of these embodiments, the aqueous formulation is filtered by a 0.22-micron filter at a time period selected from 1 hour, 2 hours, 3, hours, 4 hours, 5 hours, 6 hours, 8 hours, 12 hours, 18 hours and 24 hours. In some embodiments, the aqueous formulation is free of solvent other than water. In some embodiments, the aqueous formulation is substantially free of solvent other than water.

Also, provided herein is a pharmaceutical composition comprising the composition comprising the cabazitaxel and the human serum albumin as described herein, and a pharmaceutically acceptable carrier.

In some embodiments, the pharmaceutical composition further comprises at least one anti-cancer drug (e.g., any one of the anti-cancer drugs as described herein).

In some embodiments, the pharmaceutical composition is free of a surfactant, such as CREMOPHOR® surfactants and Polysorbate 80. In some embodiments, the pharmaceutical composition is substantially free of a surfactant, such as CREMOPHOR® surfactants and Polysorbate 80. In some embodiments, the pharmaceutical composition can be substantially free of a surfactant selected from the group consisting of CREMOPHOR® surfactants and Polysorbate 80.

Also, provided herein is a method of treating a proliferative disease comprising the step of administering to a subject in need thereof a pharmaceutical composition comprising the composition comprising the cabazitaxel and the human serum albumin as described herein, and a pharmaceutically acceptable carrier.

Also, provided herein is a method of treating a cancer (e.g., any one of cancers described herein), the method comprising the step of administering to a subject in need thereof of a therapeutically effective amount of a pharmaceutical composition comprising the composition comprising the cabazitaxel and the human serum albumin as described herein, and a pharmaceutically acceptable carrier.

In some embodiments, the cancer is a solid tumor cancer. In some embodiments, the cancer is a prostate cancer.

In some embodiments, the method of treating a prostate cancer comprises the step of administering to a subject in need thereof of a therapeutically effective amount of a pharmaceutical composition comprising the composition comprising the cabazitaxel and the human serum albumin as described herein, prednisone, and a pharmaceutically acceptable carrier.

In some embodiments, the method of treating cancer (e.g., any one of cancers described herein) comprises the step of administering to a subject in need thereof a therapeutically effective amount of a pharmaceutical composition comprising the composition comprising the cabazitaxel and the human serum albumin as described herein, and a therapeutically effective amount of at least one inhibitor of the kinases for the treatment of cancer described herein.

In some embodiments, the method of treating cancer (e.g. any one of cancers described herein) comprises the step of administering to a subject in need thereof a therapeutically effective amount of a pharmaceutical composition comprising the composition comprising the cabazitaxel and the human serum albumin as described herein, and a therapeutically effective amount of at least one anti-cancer drug described herein.

In some embodiments, a composition comprising the cabazitaxel and the human serum albumin as described herein and an anti-cancer drug are administered simultaneously.

In some embodiments, a composition comprising the cabazitaxel and the human serum albumin as described herein and an anti-cancer drug are administered consecutively.

The compositions comprising the cabazitaxel and the human serum albumin described herein can be administered to an individual, such as human, via various routes, such as parenterally, including intravenous, intra-arterial, intraperitoneal, intrapulmonary, oral, inhalation, intravesicular, intramuscular, intra-tracheal, subcutaneous, intraocular, intrathecal, or transdermal. For example, the composition can be administered by inhalation to treat conditions of the respiratory tract. The composition can be used to treat respiratory conditions such as pulmonary fibrosis, broncheolitis obliterans, lung cancer, bronchoalveolar carcinoma, and the like. In some embodiments, the composition is administrated intravenously.

The methods described herein may be performed alone or in conjunction with another therapy, such as surgery, radiation, chemotherapy, immunotherapy, gene therapy, and the like. Additionally, a person having a greater risk of developing the proliferative disease may receive treatments to inhibit and/or delay the development of the disease.

As will be understood by those of ordinary skill in the art, the appropriate doses of cabazitaxel will be approximately those already employed in clinical therapies wherein cabazitaxel is administered alone or in combination with other chemotherapeutic agents. Variation in dosage will likely occur depending on the condition being treated. Appropriate effective doses will also vary, as recognized by those skilled in the art, depending on the severity of the disease, the route of administration, the sex, age and general health condition of the subject, excipient usage, the possibility of co-usage with other therapeutic treatments such as use of other agents, and the judgment of the treating physician. For example, guidance for selecting an effective dose can be determined by reference to the prescribing information for cabazitaxel.

Also, provided herein is a composition consisting essentially of cabazitaxel and human serum albumin, wherein the cabazitaxel and the human serum albumin in the composition have a ratio by weight from about 1:10 to about 1:3000. In some embodiments, the pH of the composition is neutral (e.g., pH of the composition is from about 5 to about 8, from about 5.5 to about 7.5, or from about 6 to about 7, or the pH of the composition is about 5, about 5.5, about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8).

In some embodiments, the cabazitaxel and the human serum albumin in the composition have a ratio by weight from about 1:100 to about 1:2000. In some embodiments, the cabazitaxel and the human serum albumin in the composition have a ratio by weight from about 1:150 to about 1:1000. In some embodiments, the cabazitaxel and the human serum albumin in the composition have a ratio by weight from about 1:150 to about 1:800. In some embodiments, the cabazitaxel and the human serum albumin in the composition have a ratio by weight from about 1:150 to about 1:600. In some embodiments, the cabazitaxel and the human serum albumin in the composition have a ratio by weight from about 1:150 to about 1:500. In some embodiments, the cabazitaxel and the human serum albumin in the composition have a ratio by weight from about 1:150 to about 1:400. In some embodiments, the cabazitaxel and the human serum albumin in the composition have a ratio by weight from about 1:200 to about 1:1000. In some embodiments, the cabazitaxel and the human serum albumin in the composition have a ratio by weight from about 1:200 to about 1:800. In some embodiments, the cabazitaxel and the human serum albumin in the composition have a ratio by weight from about 1:200 to about 1:600. In some embodiments, the cabazitaxel and the human serum albumin in the composition have a ratio by weight from about 1:200 to about 1:500. In some embodiments, the cabazitaxel and the human serum albumin in the composition have a ratio by weight from about 1:200 to about 1:400. In some embodiments, the cabazitaxel and the human serum albumin in the composition have a ratio by weight from about 1:250 to about 1:1000. In some embodiments, the cabazitaxel and the human serum albumin in the composition have a ratio by weight from about 1:250 to about 1:800. In some embodiments, the cabazitaxel and the human serum albumin in the composition have a ratio by weight from about 1:250 to about 1:600. In some embodiments, the cabazitaxel and the human serum albumin in the composition have a ratio by weight from about 1:250 to about 1:500. In some embodiments, the cabazitaxel and the human serum albumin in the composition have a ratio by weight from about 1:250 to about 1:400. In some embodiments, the cabazitaxel and the human serum albumin in the composition have a ratio by weight from about 1:300 to about 1:600. In some embodiments, the cabazitaxel and the human serum albumin in the composition have a ratio by weight from about 1:300 to about 1:400. In some embodiments, the cabazitaxel and the human serum albumin in the composition have a ratio by weight from about 1:100 to about 1:1000. In some embodiments, the cabazitaxel and the human serum albumin in the composition have a ratio by weight from about 1:220 to about 1:600. In some embodiments, the cabazitaxel and the human serum albumin in the composition have a ratio by weight of about 1:200, 1:210, 1:220, about 1:230, about 1:240, about 1:250, about 1:260, about 1:270, about 1:280, about 1:290, about 1:300, about 1:310, about 1:320, about 1:330, about 1:340, about 1:350, about 1:360, about 1:370, about 1:380, about 1:390, about 1:400, about 1:450, about 1:460, about 1:500 or about 1:600.

In some embodiments, the human serum albumin is a native human serum albumin. In some embodiments, the human serum albumin is a recombinant human serum albumin. In some embodiments, the human serum albumin is a fatty acid free human serum albumin. In some embodiments, the human serum albumin is essentially fatty acid free. In some embodiments, the human serum albumin contains no more than two moles of fatty acids bound to one mole of human serum albumin. In some embodiments, the human serum albumin contains no more than one mole of fatty acids bound to one mole of human serum albumin. In some embodiments, human serum albumin contains no more than 0.5 moles of fatty acids bound to one mole of human serum albumin. In some embodiments, the human serum albumin contains no more than 0.1 moles of fatty acids bound to one mole of human serum albumin. In some embodiments, the human serum albumin contains no more than 0.05 moles of fatty acids bound to one mole of human serum albumin. In some embodiments, the human serum albumin contains no more than 0.01 moles of fatty acids bound to one mole of human serum albumin. In some embodiments, the human serum albumin contains no more than 0.001 moles of fatty acids bound to one mole of human serum albumin. In some embodiments, the human serum albumin contains no more than 0.0005 moles of fatty acids bound to one mole of human serum albumin. In some embodiments, the human serum albumin contains no more than 0.0001 moles of fatty acids bound to one mole of human serum albumin.

In some embodiments, the cabazitaxel can be a pharmaceutically acceptable salt of cabazitaxel. In some embodiments, cabazitaxel can be any one of crystal forms, amorphous forms, solvates and hydrates as described herein.

In some embodiments, the composition is a clear aqueous solution when the composition is dissolved in an aqueous solvent. In some embodiments, the aqueous solution is substantially free of solvent other than water. In some embodiments, the aqueous solution is free of solvent other than water.

In some embodiments, the composition is a clear aqueous solution when the composition is dissolved in water. In some embodiments, the composition is a clear aqueous solution when the composition is dissolved in 0.9% saline. In some embodiments, the composition is a clear aqueous solution when the composition is dissolved in 5% dextrose solution.

As used herein, the term "aqueous solution" refers to a solution, wherein at least one solvent is water and the weight % of water in the mixture of solvents is at least 50%, at least 60%, at least 70% or at least 90%. In some embodiments, aqueous solution is a solution in which water is the only solvent. In some embodiments, aqueous solution is 0.9% saline solution. In some embodiments, aqueous solution is 5% dextrose water solution. In some embodiments, aqueous solution is a buffer (e.g., phosphate buffer or a carbonate buffer). In some embodiments, the buffer is physiological buffer or a pharmaceutically acceptable buffer. In some embodiments, the buffer is any one of buffers described, for example, in Y.-C. Lee et al. International Journal of Pharmaceutics 253 (2003) 111-119, the disclosure of which is incorporated herein by reference in its entirety. In some embodiments, the buffer comprises maleic acid, tartaric acid, lactic acid, citric acid, acetic acid, sodium bicarbonate, sodium phosphate, or mixtures thereof. In some embodiments, the pH range of the buffer is from about 3 to about 9, from about 4 to about 8, from about 5 to about 7, from about 6 to about 7, from about 3 to about 5, from about 3 to about 7, from about 4 to about 6, or from about 6 to about 6. In some embodiments, the pH of the buffer is about 4, about 5, about 6, about 6.4, about 6.5, about 6.6, about 7, about 7.5, or about 8.

As used herein, the term "aqueous solvent" refer to a liquid comprising at least 50%, at least 60%, at least 70%, at least 90% or at least 95% water. In some embodiments, aqueous solvent is water.

As used herein, "substantially free of solvent," in reference to an aqueous solution, refers to an aqueous solution that contains less than 0.5%, by weight, of any non-water solvent. In some embodiments, the aqueous solution contains less than 0.1%, by weight, of any non-water solvent. In some embodiments, the aqueous solution contains less than 0.05%, by weight, of any non-water solvent.

In some embodiments, provided herein is a composition consisting essentially of cabazitaxel and human serum albumin, wherein the cabazitaxel and the human serum albumin in the composition have a ratio by weight from about 1:150 to about 1:1000, wherein the composition is a clear aqueous solution when the composition is dissolved in an aqueous solution, and wherein the clear aqueous solution has pH value from about 5 to about 8.

In some embodiments, provided herein is a composition consisting essentially of cabazitaxel and human serum albumin, wherein the cabazitaxel and the human serum albumin in the composition have a ratio by weight from about 1:150 to about 1:1000, wherein the composition is a clear aqueous solution when the composition is dissolved in an aqueous solution, and wherein the clear aqueous solution has pH value from about 6 to about 7.5.

In some embodiments, provided herein is a composition consisting essentially of cabazitaxel and human serum albumin, wherein the cabazitaxel and the human serum albumin in the composition have a ratio by weight from about 1:200 to about 1:600, wherein the composition is a clear aqueous solution when the composition is dissolved in an aqueous solution, and wherein the clear aqueous solution has pH value from about 5 to about 8.

In some embodiments, provided herein is a composition consisting essentially of cabazitaxel and human serum albumin, wherein the cabazitaxel and the human serum albumin in the composition have a ratio by weight from about 1:200 to about 1:600, wherein the composition is a clear aqueous solution when the composition is dissolved in an aqueous solution, and wherein the clear aqueous solution has pH value from about 6 to about 7.5.

In some embodiments, provided herein is a composition consisting essentially of cabazitaxel and human serum albumin, wherein the cabazitaxel and the human serum albumin in the composition have a ratio by weight from about 1:250 to about 1:500, wherein the composition is a clear aqueous solution when the composition is dissolved in an aqueous solution, and wherein the clear aqueous solution has pH value from about 5 to about 8.

In some embodiments, provided herein is a composition consisting essentially of cabazitaxel and human serum albumin, wherein the cabazitaxel and the human serum albumin in the composition have a ratio by weight from about 1:250 to about 1:500, wherein the composition is a clear aqueous solution when the composition is dissolved in an aqueous solution, and wherein the clear aqueous solution has pH value from about 6 to about 7.5.

In some embodiments, provided herein is a composition consisting essentially of cabazitaxel and human serum albumin, wherein the cabazitaxel and the human serum albumin in the composition have a ratio by weight from about 1:150 to about 1:1000, wherein the composition is a clear aqueous solution when the composition is dissolved in an aqueous solution, and wherein the clear aqueous solution has pH value from about 5 to about 8, and wherein the clear aqueous solution is substantially free of solvent other than water. In some embodiments, provided herein is a composition consisting essentially of cabazitaxel and human serum albumin, wherein the cabazitaxel and the human serum albumin in the composition have a ratio by weight from about 1:150 to about 1:1000, wherein the composition is a clear aqueous solution when the composition is dissolved in an aqueous solution, and wherein the clear aqueous solution has pH value from about 5 to about 8, and wherein the clear aqueous solution is free of solvent other than water.

In some embodiments, provided herein is a composition consisting essentially of cabazitaxel and human serum albumin, wherein the cabazitaxel and the human serum albumin in the composition have a ratio by weight from about 1:200 to about 1:600, wherein the composition is a clear aqueous solution when the composition is dissolved in an aqueous solution, and wherein the clear aqueous solution has pH value from about 5 to about 8, and wherein the clear aqueous solution is substantially free of solvent other than water. In some embodiments, provided herein is a composition consisting essentially of cabazitaxel and human serum albumin, wherein the cabazitaxel and the human serum albumin in the composition have a ratio by weight from about 1:200 to about 1:600, wherein the composition is a clear aqueous solution when the composition is dissolved in an aqueous solution, and wherein the clear aqueous solution has pH value from about 5 to about 8, and wherein the clear aqueous solution is free of solvent other than water.

In some embodiments, provided herein is a composition consisting essentially of cabazitaxel and human serum albumin, wherein the cabazitaxel and the human serum albumin in the composition have a ratio by weight from about 1:250 to about 1:500, wherein the composition is a clear aqueous solution when the composition is dissolved in an aqueous solution, and wherein the clear aqueous solution has pH value from about 5 to about 8, and wherein the clear aqueous solution is substantially free of solvent other than water. In some embodiments, provided herein is a composition comprising cabazitaxel and human serum albumin, wherein the cabazitaxel and the human serum albumin in the composition have a ratio by weight from about 1:250 to about 1:500, wherein the composition is a clear aqueous solution when the composition is dissolved in an aqueous solution, and wherein the clear aqueous solution has pH value from about 5 to about 8, and wherein the clear aqueous solution is free of solvent other than water.

In some embodiments, provided herein is a composition consisting essentially of cabazitaxel and human serum albumin, wherein the cabazitaxel and the human serum albumin in the composition have a ratio by weight from about 1:150 to about 1:1000, wherein the composition is a clear aqueous solution when the composition is dissolved in an aqueous solution, and wherein the clear aqueous solution has pH value from about 6 to about 7.5, and wherein the clear aqueous solution is substantially free of solvent other than water. In some embodiments, provided herein is a composition consisting essentially of cabazitaxel and human serum albumin, wherein the cabazitaxel and the human serum albumin in the composition have a ratio by weight from about 1:150 to about 1:1000, wherein the composition is a clear aqueous solution when the composition is dissolved in an aqueous solution, and wherein the clear aqueous solution has pH value from about 6 to about 7.5, and wherein the clear aqueous solution is free of solvent other than water.

In some embodiments, provided herein is a composition consisting essentially of cabazitaxel and human serum albumin, wherein the cabazitaxel and the human serum albumin in the composition have a ratio by weight from about 1:200 to about 1:600, wherein the composition is a clear aqueous solution when the composition is dissolved in an aqueous solution, and wherein the clear aqueous solution has pH value from about 6 to about 7.5, and wherein the clear aqueous solution is substantially free of solvent other than water. In some embodiments, provided herein is a composition consisting essentially of cabazitaxel and human serum albumin, wherein the cabazitaxel and the human serum albumin in the composition have a ratio by weight from about 1:200 to about 1:600, wherein the composition is a clear aqueous solution when the composition is dissolved in an aqueous solution, and wherein the clear aqueous solution has pH value from about 6 to about 7.5, and wherein the clear aqueous solution is free of solvent other than water.

In some embodiments, provided herein is a composition consisting essentially of cabazitaxel and human serum albumin, wherein the cabazitaxel and the human serum albumin in the composition have a ratio by weight from about 1:250 to about 1:500, wherein the composition is a clear aqueous solution when the composition is dissolved in an aqueous solution, and wherein the clear aqueous solution has pH value from about 6 to about 7.5, and wherein the clear aqueous solution is substantially free of solvent other than water. In some embodiments, provided herein is a composition consisting essentially of cabazitaxel and human serum albumin, wherein the cabazitaxel and the human serum albumin in the composition have a ratio by weight from about 1:250 to about 1:500, wherein the composition is a clear aqueous solution when the composition is dissolved in an aqueous solution, and wherein the clear aqueous solution has pH value from about 6 to about 7.5, and wherein the clear aqueous solution is free of solvent other than water.

In some embodiments, the composition forms a clear aqueous solution, when the composition is dissolved in an aqueous solvent, wherein the clear aqueous solution has pH value from about 5 to about 8. In some embodiments, the composition forms a clear aqueous solution, when the composition is dissolved in an aqueous solvent, wherein the clear aqueous solution has pH value from about 5.5 to about 7.8. In some embodiments, the composition forms a clear aqueous solution, when the composition is dissolved in an aqueous solvent, wherein the clear aqueous solution has pH value from about 6 to about 7.5. In some embodiments, the composition forms a clear aqueous solution, when the composition is dissolved in an aqueous solvent, wherein the clear aqueous solution has pH value from about 6.5 to about 7.5. In some embodiments, the composition forms a clear aqueous solution, when the composition is dissolved in an aqueous solvent, wherein the clear aqueous solution has pH value from about 6 to about 6.5. In some embodiments, the composition forms a clear aqueous solution, when the composition is dissolved in an aqueous solvent, wherein the clear aqueous solution has pH value from about 6.5 to about 7. In some embodiments, the composition forms a clear aqueous solution, when the composition is dissolved in an aqueous solvent, wherein the clear aqueous solution has pH value from about 7 to about 7.5. In some embodiments, the composition forms a clear aqueous solution, when the composition is dissolved in an aqueous solvent wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5. In some embodiments, the aqueous solution is substantially free of solvent other than water. In some embodiments, the aqueous solution is free of solvent other than water.

In some embodiments, the composition forms a clear aqueous solution, when the composition is dissolved in water, wherein the clear aqueous solution has pH value from about 5 to about 8. In some embodiments, the composition forms a clear aqueous solution, when the composition is dissolved in water, wherein the clear aqueous solution has pH value from about 5.5 to about 7.8. In some embodiments, the composition forms a clear aqueous solution, when the composition is dissolved in water, wherein the clear aqueous solution has pH value from about 6 to about 7.5. In some embodiments, the composition forms a clear aqueous solution, when the composition is dissolved in water, wherein the clear aqueous solution has pH value from about 6.5 to about 7.5. In some embodiments, the composition forms a clear aqueous solution, when the composition is dissolved in water, wherein the clear aqueous solution has pH value from about 6 to about 6.5. In some embodiments, the composition forms a clear aqueous solution, when the composition is dissolved in water, wherein the clear aqueous solution has pH value from about 6.5 to about 7. In some embodiments, the composition forms a clear aqueous solution, when the composition is dissolved in water, wherein the clear aqueous solution has pH value from about 7 to about 7.5. In some embodiments, the composition forms a clear aqueous solution, when the composition is dissolved in water, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5.

In some embodiments, the composition forms a clear aqueous solution, when the composition is dissolved in 0.9% saline, wherein the clear aqueous solution has pH value from about 5 to about 8. In some embodiments, the composition forms a clear aqueous solution, when the composition is dissolved in 0.9% saline, wherein the clear aqueous solution has pH value from about 5.5 to about 7.8. In some embodiments, the composition forms a clear aqueous solution, when the composition is dissolved in 0.9% saline, wherein the clear aqueous solution has pH value from about 6 to about 7.5. In some embodiments, the composition forms a clear aqueous solution, when the composition is dissolved in 0.9% saline, wherein the clear aqueous solution has pH value from about 6.5 to about 7.5. In some embodiments, the composition forms a clear aqueous solution, when the composition is dissolved in 0.9% saline, wherein the clear aqueous solution has pH value from about 6 to about 6.5. In some embodiments, the composition forms a clear aqueous solution, when the composition is dissolved in 0.9% saline, wherein the clear aqueous solution has pH value from about 6.5 to about 7. In some embodiments, the composition forms a clear aqueous solution, when the composition is dissolved in 0.9% saline, wherein the clear aqueous solution has pH value from about 7 to about 7.5. In some embodiments, the composition forms a clear aqueous solution, when the composition is dissolved in 0.9% saline, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5.

In some embodiments, the composition forms a clear aqueous solution, when the composition is dissolved in 5% dextrose solution, wherein the clear aqueous solution has pH value from about 5 to about 8. In some embodiments, the composition forms a clear aqueous solution, when the composition is dissolved in 5% dextrose solution, wherein the clear aqueous solution has pH value from about 5.5 to about 7.8. In some embodiments, the composition forms a clear aqueous solution, when the composition is dissolved in 5% dextrose solution, wherein the clear aqueous solution has pH value from about 6 to about 7.5. In some embodiments, the composition forms a clear aqueous solution, when the composition is dissolved in 5% dextrose solution, wherein the clear aqueous solution has pH value from about 6.5 to about 7.5. In some embodiments, the composition forms a clear aqueous solution, when the composition is dissolved in 5% dextrose solution, wherein the clear aqueous solution has pH value from about 6 to about 6.5. In some embodiments, the composition forms a clear aqueous solution, when the composition is dissolved in 5% dextrose solution, wherein the clear aqueous solution has pH value from about 6.5 to about 7. In some embodiments, the composition forms a clear aqueous solution, when the composition is dissolved in 5% dextrose solution, wherein the clear aqueous solution has pH value from about 7 to about 7.5. In some embodiments, the composition forms a clear aqueous solution, when the composition is dissolved in 5% dextrose solution, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5.

In some embodiments, the composition is a clear aqueous solution when the composition is dissolved in an aqueous solvent (e.g. water, 0.9% saline, or 5% dextrose solution), wherein after the clear aqueous solution is filtered by a 0.22 micron filter, the amount of cabazitaxel in the filtered aqueous solution is at least 95% of the total amount of cabazitaxel in the aqueous solution before the filtration. In some embodiments, the composition is a clear aqueous solution when the composition is dissolved in an aqueous solvent (e.g. water, 0.9% saline, or 5% dextrose solution), wherein after the clear aqueous solution is filtered by a 0.22 micron filter, the amount of cabazitaxel in the filtered aqueous solution is at least 96% of the total amount of cabazitaxel in the aqueous solution before the filtration. In some embodiments, the composition is a clear aqueous solution when the composition is dissolved in an aqueous solvent (e.g. water, 0.9% saline, or 5% dextrose solution), wherein after the clear aqueous solution is filtered by a 0.22 micron filter, the amount of cabazitaxel in the filtered aqueous solution is at least 97% of the total amount of cabazitaxel in the aqueous solution before the filtration. In some embodiments, the composition is a clear aqueous solution when the composition is dissolved in an aqueous solution (e.g. water, 0.9% saline, or 5% dextrose solution), wherein after the clear aqueous solution is filtered by a 0.22 micron filter, the amount of cabazitaxel in the filtered aqueous solution is at least 98% of the total amount of cabazitaxel in the aqueous solution before the filtration. In some embodiments, the composition is a clear aqueous solution when the composition is dissolved in an aqueous solution (e.g. water, 0.9% saline, or 5% dextrose solution), wherein after the clear aqueous solution is filtered by a 0.22 micron filter, the amount of cabazitaxel in the filtered aqueous solution is at least 99% of the total amount of cabazitaxel in the aqueous solution before the filtration. In some embodiments, the composition is a clear aqueous solution when the composition is dissolved in an aqueous solution (e.g. water, 0.9% saline, or 5% dextrose solution), wherein after the clear aqueous solution is filtered by a 0.22 micron filter, the amount of cabazitaxel in the filtered aqueous solution is at least 99.5% of the total amount of cabazitaxel in the aqueous solution before the filtration. In some embodiments, the aqueous solution is free of solvent other than water. In some embodiments, the aqueous solution is substantially free of solvent other than water.

In some embodiments, the composition is a clear aqueous solution when the composition is dissolved in an aqueous solution, wherein after the clear aqueous solution is filtered by a 0.22 micron filter, the amount of cabazitaxel in the filtered aqueous solution is at least 95%, 96%, 97%, 98%, 99%, or 99.5% of the total amount of cabazitaxel in the aqueous solution before the filtration, wherein the clear aqueous solution has pH value from about 5 to about 8, and wherein the clear aqueous solution is substantially free of solvent other than water. In some embodiments, the composition is a clear aqueous solution when the composition is dissolved in an aqueous solution, wherein after the clear aqueous solution is filtered by a 0.22 micron filter, the amount of cabazitaxel in the filtered aqueous solution is at least 95%, 96%, 97%, 98%, 99%, or 99.5% of the total amount of cabazitaxel in the aqueous solution before the filtration, wherein the clear aqueous solution has pH value from about 6 to about 7.5, and wherein the clear aqueous solution is substantially free of solvent other than water. In some embodiments, the composition is a clear aqueous solution when the composition is dissolved in an aqueous solution, wherein after the clear aqueous solution is filtered by a 0.22 micron filter, the amount of cabazitaxel in the filtered aqueous solution is at least 95%, 96%, 97%, 98%, 99%, or 99.5% of the total amount of cabazitaxel in the aqueous solution before the filtration, wherein the clear aqueous solution has pH value from about 5 to about 8, and wherein the clear aqueous solution is free of solvent other than water. In some embodiments, the composition is a clear aqueous solution when the composition is dissolved in an aqueous solution, wherein after the clear aqueous solution is filtered by a 0.22 micron filter, the amount of cabazitaxel in the filtered aqueous solution is at least 95%, 96%, 97%, 98%, 99%, or 99.5% of the total amount of cabazitaxel in the aqueous solution before the filtration, wherein the clear aqueous solution has pH value from about 6 to about 7.5, and wherein the clear aqueous solution is free of solvent other than water.

In some embodiments, the amount of cabazitaxel that is bound to the HSA (e.g., non-covalently) in the aqueous solution (e.g., clear aqueous solution) comprising the composition consisting essentially of cabazitaxel and HSA (as described herein) is at least 40%, at least 50%, at least 60%, at least 70%, at least 80%, at least 90%, at least 95%, at least 99%, or about 100% of the total about of cabazitaxel in the aqueous solution.

In some embodiments, the composition is an aqueous solution, wherein after the aqueous solution is filtered by a 0.22 micron filter, the amount of cabazitaxel in the filtered aqueous solution is at least 80% of the total amount of cabazitaxel in the aqueous solution before the filtration. In some embodiments, the composition is an aqueous solution, wherein after the aqueous solution is filtered by a 0.22 micron filter, the amount of cabazitaxel in the filtered aqueous solution is at least 85% of the total amount of cabazitaxel in the aqueous solution before the filtration. In some embodiments, the composition is an aqueous solution, wherein after the aqueous solution is filtered by a 0.22 micron filter, the amount of cabazitaxel in the filtered aqueous solution is at least 90% of the total amount of cabazitaxel in the aqueous solution before the filtration. In some embodiments, the aqueous solution is free of solvent other than water. In some embodiments, the aqueous solution is substantially free of solvent other than water.

In some embodiments, the composition is a clear aqueous solution for at least 1 hour when the composition is dissolved in an aqueous solution (e.g. water, 0.9% saline, or 5% dextrose solution). In some embodiments, the composition is a clear aqueous solution for at least 2 hours when the composition is dissolved in an aqueous solution (e.g. water, 0.9% saline, or 5% dextrose solution). In some embodiments, the composition is a clear aqueous solution for at least 3 hours when the composition is dissolved in an aqueous solution (e.g. water, 0.9% saline, or 5% dextrose solution). In some embodiments, the composition is a clear aqueous solution for at least 4 hours when the composition is dissolved in an aqueous solution (e.g. water, 0.9% saline, or 5% dextrose solution). In some embodiments, the composition is a clear aqueous solution for at least 5 hours when the composition is dissolved in an aqueous solution (e.g. water, 0.9% saline, or 5% dextrose solution). In some embodiments, the composition is a clear aqueous solution for at least 6 hours when the composition is dissolved in an aqueous solution (e.g. water, 0.9% saline, or 5% dextrose solution). In some embodiments, the composition is a clear aqueous solution for at least 8 hours when the composition is dissolved in an aqueous solution (e.g. water, 0.9% saline, or 5% dextrose solution). In some embodiments, the composition is a clear aqueous solution for at least 24 hours when the composition is dissolved in an aqueous solution (e.g. water, 0.9% saline, or 5% dextrose solution). In some embodiments, the composition is a clear aqueous solution for at least 3 days when the composition is dissolved in an aqueous solution (e.g. water, 0.9% saline, or 5% dextrose solution). In some embodiments, the aqueous solution is substantially free of solvent other than water. In some embodiments, the aqueous solution is free of solvent other than water.

In some embodiments, the composition is a solid formulation. For example, the solid formulation can be produced in a uniform manner by lyophilization. A skilled artisan would recognize other methods, such as rotary evaporation, that can also produce solid formulations.

In some embodiments, the composition is an aqueous formulation. In some embodiments, the aqueous formulation is substantially free of solvent other than water. In some embodiments, the aqueous formulation is free of solvent other than water. In some embodiments, the aqueous formulation includes water and water-miscible organic solvents including at least one of polyethylene glycol 300, polyethylene glycol 400, ethanol, methanol, propylene glycol, glycerin, N-methyl-2-pyrrolidone, dimethylacetamide, and dimethylsulfoxide. For example, the water-miscible organic solvent can include ethanol. In some embodiments, the aqueous formulation includes water and ethanol. In some embodiments, the water-miscible organic solvent can be a mixture of water-miscible organic solvents. In some embodiments, the pH of the aqueous formulation (e.g., clear aqueous solution) is neutral (e.g., pH of the composition is from about 5 to about 8, from about 5.5 to about 7.5, or from about 6 to about 7, or the pH od the composition is about 5, about 5.5, about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5 or about 8).

In some embodiments, the aqueous formulation can be free of a surfactant, such as CREMOPHOR® surfactants and Polysorbate 80. In some embodiments, the aqueous formulation can be substantially free of a surfactant, such as CREMOPHOR® surfactants and Polysorbate 80. In some embodiments, the aqueous formulation can be substantially free of a surfactant selected from the group consisting of CREMOPHOR® surfactants and Polysorbate 80.

As used herein, the term "substantially free of surfactant" refers to a formulation containing less than 0.0005%, less than 0.0003%, or less than 0.0001% of surfactants and/or less than 0.0005%, less than 0.0003%, or less than 0.0001% of surfactant.

In some embodiments, the aqueous formulation is a clear aqueous solution. For example, the formulation can be a clear and stable aqueous solution reconstituted from a sterile lyophilized powder. In some embodiments, the aqueous formulation is a clear aqueous solution, wherein the aqueous formulation is substantially free of solvent other than water. In some embodiments, the aqueous formulation is a clear aqueous solution, wherein the aqueous formulation is free of solvent other than water.

In some embodiments, the aqueous formulation is a clear aqueous solution reconstituted from the solid formulation (e.g. the sterile lyophilized powder) in water. In some embodiments, the aqueous formulation is a clear aqueous solution reconstituted from the solid formulation (e.g. the sterile lyophilized powder) in 0.9% saline. In some embodiments, the aqueous formulation is a clear aqueous solution reconstituted from the solid formulation (e.g. the sterile lyophilized powder) in 5% dextrose solution.

In some embodiments, the aqueous formulation is a clear aqueous solution reconstituted from the solid formulation (e.g. the sterile lyophilized powder) in water, wherein the aqueous formulation has pH value from about 5 to about 8. In some embodiments, the aqueous formulation is a clear aqueous solution reconstituted from the solid formulation (e.g. the sterile lyophilized powder) in 0.9% saline, wherein the aqueous formulation has pH value from about 5 to about 8. In some embodiments, the aqueous formulation is a clear aqueous solution reconstituted from the solid formulation (e.g. the sterile lyophilized powder) in 5% dextrose solution, wherein the aqueous formulation has pH value from about 5 to about 8.

In some embodiments, the aqueous formulation is a clear aqueous solution reconstituted from the solid formulation (e.g. the sterile lyophilized powder) in water, wherein the pH of water is about 7, and wherein the aqueous formulation has pH value from about 5 to about 8. In some embodiments, the aqueous formulation is a clear aqueous solution reconstituted from the solid formulation (e.g. the sterile lyophilized powder) in 0.9% saline solution, wherein the pH of 0.9% saline solution is about 5.4, and wherein the aqueous formulation has pH value from about 5 to about 8. In some embodiments, the aqueous formulation is a clear aqueous solution reconstituted from the solid formulation (e.g. the sterile lyophilized powder) in 5% dextrose water solution, wherein the pH of 5% dextrose solution is about 4.4, and wherein the aqueous formulation has pH value from about 5 to about 8. In some aspects of the aforementioned embodiments, the concentration of the reconstituted solid in the aqueous formulation is about 25 mg, about 50 mg, about 75 mg, about 100 mg, about 150 mg or 200 mg per 1 mL of the aqueous solvent.

In some embodiments, the aqueous formulation is a clear aqueous solution reconstituted from the solid formulation (e.g. the sterile lyophilized powder) in water, wherein the aqueous formulation has pH value from about 6 to about 7.5. In some embodiments, the aqueous formulation is a clear aqueous solution reconstituted from the solid formulation (e.g. the sterile lyophilized powder) in 0.9% saline, wherein the aqueous formulation has pH value from about 6 to about 7.5. In some embodiments, the aqueous formulation is a clear aqueous solution reconstituted from the solid formulation (e.g. the sterile lyophilized powder) in 5% dextrose solution, wherein the aqueous formulation has pH value from about 6 to about 7.5.

In some embodiments, the aqueous formulation is a clear aqueous solution reconstituted from the solid formulation (e.g. the sterile lyophilized powder) in water, wherein the pH of water is about 7, and wherein the aqueous formulation has pH value from about 6 to about 7.5. In some embodiments, the aqueous formulation is a clear aqueous solution reconstituted from the solid formulation (e.g. the sterile lyophilized powder) in 0.9% saline solution, wherein the pH of 0.9% saline solution is about 5.4, and wherein the aqueous formulation has pH value from about 6 to about 7.5. In some embodiments, the aqueous formulation is a clear aqueous solution reconstituted from the solid formulation (e.g. the sterile lyophilized powder) in 5% dextrose water solution, wherein pH of the 5% dextrose solution is about 4.4, and wherein the aqueous formulation has pH value from about 6 to about 7.5.

In some embodiments, the aqueous formulation is a clear aqueous solution reconstituted from the solid formulation (e.g. the sterile lyophilized powder) in water, wherein the pH of water is about 7, and wherein the aqueous formulation has pH value of about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8. In some embodiments, the aqueous formulation is a clear aqueous solution reconstituted from the solid formulation (e.g. the sterile lyophilized powder) in 0.9% saline solution, wherein the pH of 0.9% saline solution is about 5.4, and wherein the aqueous formulation has pH value of about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8. In some embodiments, the aqueous formulation is a clear aqueous solution reconstituted from the solid formulation (e.g. the sterile lyophilized powder) in 5% dextrose water solution, wherein pH of the 5% dextrose solution is about 4.4, and wherein the aqueous formulation has pH value of about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8.

In some embodiments, the aqueous formulation has pH value from about 5 to about 8. In some embodiments, the aqueous formulation has pH value from about 5.5 to about 7.8. In some embodiments, the aqueous formulation has pH value from about 6 to about 7.5. In some embodiments, the aqueous formulation has pH value from about 6.5 to about 7.5. In some embodiments, the aqueous formulation has pH value from about 6 to about 6.5. In some embodiments, the aqueous formulation has pH value from about 6.5 to about 7. In some embodiments, the aqueous formulation has pH value from about 7 to about 7.5. In some embodiments, the aqueous formulation has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5. In some embodiments, the aqueous formulation is substantially free of solvent other than water. In some embodiments, the aqueous formulation is free of solvent other than water.

In some embodiments, the aqueous formulation is a clear aqueous solution, wherein the aqueous formulation has pH value from about 5 to about 8, and wherein the aqueous formulation is substantially free of solvent other than water. In some embodiments, the aqueous formulation is a clear aqueous solution, wherein the aqueous formulation has pH value from about 5 to about 8, and wherein the aqueous formulation is free of solvent other than water. In some embodiments, the aqueous formulation is a clear aqueous solution, wherein the aqueous formulation has pH value from about 5.5 to about 7.8, and wherein the aqueous formulation is substantially free of solvent other than water. In some embodiments, the aqueous formulation is a clear aqueous solution, wherein the aqueous formulation has pH value from about 5.5 to about 7.8, and wherein the aqueous formulation is free of solvent other than water. In some embodiments, the aqueous formulation is a clear aqueous solution, wherein the aqueous formulation has pH value from about 6 to about 7.5, and wherein the aqueous formulation is substantially free of solvent other than water. In some embodiments, the aqueous formulation is a clear aqueous solution, wherein the aqueous formulation has pH value from about 6 to about 7.5, and wherein the aqueous formulation is free of solvent other than water. In some embodiments, the aqueous formulation is a clear aqueous solution, wherein the aqueous formulation has pH value from about 6.5 to about 7.5, and wherein the aqueous formulation is substantially free of solvent other than water. In some embodiments, the aqueous formulation is a clear aqueous solution, wherein the aqueous formulation has pH value from about 6.5 to about 7.5, and wherein the aqueous formulation is free of solvent other than water. In some embodiments, the aqueous formulation is a clear aqueous solution, wherein the aqueous formulation has pH value from about 6 to about 6.5, and wherein the aqueous formulation is substantially free of solvent other than water. In some embodiments, the aqueous formulation is a clear aqueous solution, wherein the aqueous formulation has pH value from about 6 to about 6.5, and wherein the aqueous formulation is free of solvent other than water. In some embodiments, the aqueous formulation is a clear aqueous solution, wherein the aqueous formulation has pH value from about 6.5 to about 7, and wherein the aqueous formulation is substantially free of solvent other than water. In some embodiments, the aqueous formulation is a clear aqueous solution, wherein the aqueous formulation has pH value from about 6.5 to about 7, and wherein the aqueous formulation is free of solvent other than water. In some embodiments, the aqueous formulation is a clear aqueous solution, wherein the aqueous formulation has pH value from about 7 to about 7.5, and wherein the aqueous formulation is substantially free of solvent other than water. In some embodiments, the aqueous formulation is a clear aqueous solution, wherein the aqueous formulation has pH value from about 7 to about 7.5, and wherein the aqueous formulation is free of solvent other than water. In some embodiments, the aqueous formulation is a clear aqueous solution, wherein the aqueous formulation has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5, and wherein the aqueous formulation is substantially free of solvent other than water. In some embodiments, the aqueous formulation is a clear aqueous solution, wherein the aqueous formulation has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5, and wherein the aqueous formulation is free of solvent other than water.

In some embodiments, after the aqueous formulation is filtered by a 0.22 micron filter, the amount of cabazitaxel in the filtered aqueous solution is at least 95% of the total amount of cabazitaxel in the aqueous solution before the filtration. In some embodiments, after the aqueous formulation is filtered by a 0.22 micron filter, the amount of cabazitaxel in the filtered aqueous solution is at least 96% of the total amount of cabazitaxel in the aqueous solution before the filtration. In some embodiments, after the aqueous formulation is filtered by a 0.22 micron filter, the amount of cabazitaxel in the filtered aqueous solution is at least 97% of the total amount of cabazitaxel in the aqueous solution before the filtration. In some embodiments, after the aqueous formulation is filtered by a 0.22 micron filter, the amount of cabazitaxel in the filtered aqueous solution is at least 98% of the total amount of cabazitaxel in the aqueous solution before the filtration. In some embodiments, after the aqueous formulation is filtered by a 0.22 micron filter, the amount of cabazitaxel in the filtered aqueous solution is at least 99% of the total amount of cabazitaxel in the aqueous solution before the filtration. In some embodiments, after the aqueous formulation is filtered by a 0.22 micron filter, the amount of cabazitaxel in the filtered aqueous solution is at least 99.5% of the total amount of cabazitaxel in the aqueous solution before the filtration. In some aspects of these embodiments, the aqueous formulation is filtered by a 0.22-micron filter at a time period selected from 1 hour, 2 hours, 3, hours, 4 hours, 5 hours, 6 hours, 8 hours, 12 hours, 18 hours and 24 hours. In some embodiments, the aqueous formulation is free of solvent other than water. In some embodiments, the aqueous formulation is substantially free of solvent other than water.

In some embodiments, after the aqueous formulation (e.g. a clear aqueous solution) is filtered by a 0.22 micron filter, the amount of cabazitaxel in the filtered aqueous solution is at least 95%, 96%, 97%, 98%, 99%, or 99.5% of the total amount of cabazitaxel in the aqueous solution before filtration, wherein the clear aqueous solution has pH value from about 5 to about 8, and wherein the clear aqueous solution is substantially free of solvent other than water. In some embodiments, after the aqueous formulation (e.g. a clear aqueous solution) is filtered by a 0.22 micron filter, the amount of cabazitaxel in the filtered aqueous solution is at least 95%, 96%, 97%, 98%, 99%, or 99.5% of the total amount of cabazitaxel in the aqueous solution before filtration, wherein the clear aqueous solution has pH value from about 6 to about 7.5, and wherein the clear aqueous solution is substantially free of solvent other than water. In some embodiments, after the aqueous formulation (e.g. a clear aqueous solution) is filtered by a 0.22 micron filter, the amount of cabazitaxel in the filtered aqueous solution is at least 95%, 96%, 97%, 98%, 99%, or 99.5% of the total amount of cabazitaxel in the aqueous solution before filtration, wherein the clear aqueous solution has pH value from about 5 to about 8, and wherein the clear aqueous solution is free of solvent other than water. In some embodiments, after the aqueous formulation (e.g. a clear aqueous solution) is filtered by a 0.22 micron filter, the amount of cabazitaxel in the filtered aqueous solution is at least 95%, 96%, 97%, 98%, 99%, or 99.5% of the total amount of cabazitaxel in the aqueous solution before filtration, wherein the clear aqueous solution has pH value from about 6 to about 7.5, and wherein the clear aqueous solution is free of solvent other than water. In some aspects of these embodiments, the aqueous formulation is filtered by a 0.22-micron filter at a time period selected from 1 hour, 2 hours, 3, hours, 4 hours, 5 hours, 6 hours, 8 hours, 12 hours, 18 hours and 24 hours.

In some embodiments, after the aqueous formulation is filtered by a 0.22 micron filter, the amount of cabazitaxel in the filtered aqueous solution is at least 80% of the total amount of cabazitaxel in the aqueous solution before the filtration. In some embodiments, after the aqueous formulation is filtered by a 0.22 micron filter, the amount of cabazitaxel in the filtered aqueous solution is at least 85% of the total amount of cabazitaxel in the aqueous solution before the filtration. In some embodiments, after the aqueous formulation is filtered by a 0.22 micron filter, the amount of cabazitaxel in the filtered aqueous solution is at least 90% of the total amount of cabazitaxel in the aqueous solution before the filtration. In some aspects of these embodiments, the aqueous formulation is filtered by a 0.22-micron filter at a time period selected from 1 hour, 2 hours, 3, hours, 4 hours, 5 hours, 6 hours, 8 hours, 12 hours, 18 hours and 24 hours. In some embodiments, the aqueous formulation is free of solvent other than water. In some embodiments, the aqueous formulation is substantially free of solvent other than water.

In some embodiments, when the composition consisting essentially of cabazitaxel and HSA as described herein (e.g., sterile solid powder) is dissolved in an aqueous solvent (e.g., water, 0.9% saline or 5% dextrose), the resultant aqueous solution, when filtered using a 0.22 micron filter, comprises at least 99% at the time of preparation, at least 99% after 1 hour, at least 99% after 2 hours, at least 98% after 3 hours, at least 98% after 4 hours, at least 98% after 5 hours, at least 98% after 6 hours, or at least 98% after 24 hours of the amount of cabazitaxel used to prepare the composition.

In some embodiments, when the composition consisting essentially of cabazitaxel and HSA as described herein (e.g., sterile solid powder) is dissolved in an aqueous solvent (e.g., water, 0.9% saline or 5% dextrose), the resultant aqueous solution, when filtered using a 0.22 micron filter, comprises at least 99% at the time of preparation, at least 99% after 1 hour, at least 99% after 2 hours, at least 99% after 3 hours, at least 99% after 4 hours, at least 99% after 5 hours, at least 99% after 6 hours, or at least 99% after 24 hours of the amount of cabazitaxel used to prepare the composition.

In some embodiments, when the composition consisting essentially of cabazitaxel and HSA as described herein (e.g., sterile solid powder) is dissolved in an aqueous solvent (e.g., water, 0.9% saline or 5% dextrose), the resultant aqueous solution, when filtered using a 0.22 micron filter, comprises at least 98% at the time of preparation, at least 98% after 1 hour, at least 98% after 2 hours, at least 98% after 3 hours, at least 98% after 4 hours, at least 98% after 5 hours, at least 98% after 6 hours, or at least 98% after 24 hours of the amount of cabazitaxel used to prepare the composition.

In some embodiments, when the composition consisting essentially of cabazitaxel and HSA as described herein (e.g., sterile solid powder) is dissolved in an aqueous solvent (e.g., water, 0.9% saline or 5% dextrose), the resultant aqueous solution, when filtered using a 0.22 micron filter, comprises at least 97% at the time of preparation, at least 97% after 1 hour, at least 97% after 2 hours, at least 97% after 3 hours, at least 97% after 4 hours, at least 97% after 5 hours, at least 97% after 6 hours, or at least 97% after 24 hours of the amount of cabazitaxel used to prepare the composition.

In some embodiments, when the composition consisting essentially of cabazitaxel and HSA as described herein (e.g., sterile solid powder) is dissolved in an aqueous solvent (e.g., water, 0.9% saline or 5% dextrose), the resultant aqueous solution, when filtered using a 0.22 micron filter, comprises at least 96% at the time of preparation, at least 96% after 1 hour, at least 96% after 2 hours, at least 96% after 3 hours, at least 96% after 4 hours, at least 96% after 5 hours, at least 96% after 6 hours, or at least 96% after 24 hours of the amount of cabazitaxel used to prepare the composition.

In some embodiments, when the composition consisting essentially of cabazitaxel and HSA as described herein (e.g., sterile solid powder) is dissolved in an aqueous solvent (e.g., water, 0.9% saline or 5% dextrose), the resultant aqueous solution, when filtered using a 0.22 micron filter, comprises at least 95% at the time of preparation, at least 95% after 1 hour, at least 95% after 2 hours, at least 95% after 3 hours, at least 95% after 4 hours, at least 95% after 5 hours, at least 95% after 6 hours, or at least 95% after 24 hours of the amount of cabazitaxel used to prepare the composition.

In some embodiments, the aqueous formulation is a clear aqueous solution for at least 1 hour. In some embodiments, the aqueous formulation is a clear aqueous solution for at least 2 hours. In some embodiments, the aqueous formulation is a clear aqueous solution for at least 3 hours. In some embodiments, the aqueous formulation is a clear aqueous solution for at least 4 hours. In some embodiments, the aqueous formulation is a clear aqueous solution for at least 5 hours. In some embodiments, the aqueous formulation is a clear aqueous solution for at least 6 hours. In some embodiments, the aqueous formulation is a clear aqueous solution for at least 8 hours. In some embodiments, the aqueous formulation is a clear aqueous solution for at least 24 hours. In some embodiments, the aqueous formulation is a clear aqueous solution for at least 6 hours at a concentration of from about 5 mg/mL to about 250 mg/mL, from about 10 mg/mL to about 200 mg/mL, from about 25 mg/mL to about 150 mg/mL, from about 10 mg/mL to about 50 mg/mL, from about 50 mg/mL to about 100 mg/mL, from about 100 mg/mL to about 150 mg/mL, from about 150 mg/mL to about 200 mg/mL, or about 5 mg/mL, about 10 mg/mL, about 20 mg/mL, about 30 mg/mL, about 40 mg/mL, about 50 mg/mL, about 60 mg/mL, about 70 mg/mL, about 80 mg/mL, about 90 mg/mL, or about 100 mg/mL at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 24 hours. In some embodiments, the aqueous formulation is a transparent aqueous solution for at least 24 hours at a concentration of from about 5 mg/mL to about 250 mg/mL, from about 10 mg/mL to about 200 mg/mL, from about 25 mg/mL to about 150 mg/mL, from about 10 mg/mL to about 50 mg/mL, from about 50 mg/mL to about 100 mg/mL, from about 100 mg/mL to about 150 mg/mL, from about 150 mg/mL to about 200 mg/mL, or about 5 mg/mL, about 10 mg/mL, about 20 mg/mL, about 30 mg/mL, about 40 mg/mL, about 50 mg/mL, about 60 mg/mL, about 70 mg/mL, about 80 mg/mL, about 90 mg/mL, or about 100 mg/mL at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 3 days. In some embodiments, the aqueous formulation is a transparent aqueous solution for at least 3 days when dissolved in an aqueous solution at a concentration of from about 5 mg/mL to about 250 mg/mL, from about 10 mg/mL to about 200 mg/mL, from about 25 mg/mL to about 150 mg/mL, from about 10 mg/mL to about 50 mg/mL, from about 50 mg/mL to about 100 mg/mL, from about 100 mg/mL to about 150 mg/mL, from about 150 mg/mL to about 200 mg/mL, or about 5 mg/mL, about 10 mg/mL, about 20 mg/mL, about 30 mg/mL, about 40 mg/mL, about 50 mg/mL, about 60 mg/mL, about 70 mg/mL, about 80 mg/mL, about 90 mg/mL, or about 100 mg/mL at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is substantially free of solvent other than water. In some embodiments, the aqueous formulation is free of solvent other than water.

In some embodiments, after the aqueous formulation is filtered by a 0.22 micron filter, the amount of cabazitaxel in the filtered aqueous solution is at least 96% of the total amount of cabazitaxel in the aqueous solution before the filtration. In some embodiments, after the aqueous formulation is filtered by a 0.22 micron filter, the amount of cabazitaxel in the filtered aqueous solution is at least 97% of the total amount of cabazitaxel in the aqueous solution before the filtration. In some embodiments, after the aqueous formulation is filtered by a 0.22 micron filter, the amount of cabazitaxel in the filtered aqueous solution is at least 98% of the total amount of cabazitaxel in the aqueous solution before the filtration. In some embodiments, after the aqueous formulation is filtered by a 0.22 micron filter, the amount of cabazitaxel in the filtered aqueous solution is at least 99% of the total amount of cabazitaxel in the aqueous solution before the filtration. In some embodiments, after the aqueous formulation is filtered by a 0.22 micron filter, the amount of cabazitaxel in the filtered aqueous solution is at least 99.5% of the total amount of cabazitaxel in the aqueous solution before the filtration. In some aspects of these embodiments, the aqueous formulation is filtered by a 0.22-micron filter at a time period selected from 1 hour, 2 hours, 3, hours, 4 hours, 5 hours, 6 hours, 8 hours, 12 hours, 18 hours and 24 hours. In some embodiments, the aqueous formulation is free of solvent other than water. In some embodiments, the aqueous formulation is substantially free of solvent other than water.

In some embodiments, after the aqueous formulation (e.g. a clear aqueous solution) is filtered by a 0.22 micron filter, the amount of cabazitaxel in the filtered aqueous solution is at least 96%, 97%, 98%, 99%, or 99.5% of the total amount of cabazitaxel in the aqueous solution before filtration, wherein the clear aqueous solution has pH value from about 5 to about 8, and wherein the clear aqueous solution is substantially free of solvent other than water. In some embodiments, after the aqueous formulation (e.g. a clear aqueous solution) is filtered by a 0.22 micron filter, the amount of cabazitaxel in the filtered aqueous solution is at least 96%, 97%, 98%, 99%, or 99.5% of the total amount of cabazitaxel in the aqueous solution before filtration, wherein the clear aqueous solution has pH value from about 6 to about 7.5, and wherein the clear aqueous solution is substantially free of solvent other than water. In some embodiments, after the aqueous formulation (e.g. a clear aqueous solution) is filtered by a 0.22 micron filter, the amount of cabazitaxel in the filtered aqueous solution is at least 96%, 97%, 98%, 99%, or 99.5% of the total amount of cabazitaxel in the aqueous solution before filtration, wherein the clear aqueous solution has pH value from about 5 to about 8, and wherein the clear aqueous solution is free of solvent other than water. In some embodiments, after the aqueous formulation (e.g. a clear aqueous solution) is filtered by a 0.22 micron filter, the amount of cabazitaxel in the filtered aqueous solution is at least 96%, 97%, 98%, 99%, or 99.5% of the total amount of cabazitaxel in the aqueous solution before filtration, wherein the clear aqueous solution has pH value from about 6 to about 7.5, and wherein the clear aqueous solution is free of solvent other than water. In some aspects of these embodiments, the aqueous formulation is filtered by a 0.22-micron filter at a time period selected from 1 hour, 2 hours, 3, hours, 4 hours, 5 hours, 6 hours, 8 hours, 12 hours, 18 hours and 24 hours.

In some embodiments, after the aqueous formulation is filtered by a 0.22 micron filter, the amount of cabazitaxel in the filtered aqueous solution is at least 80% of the total amount of cabazitaxel in the aqueous solution before the filtration. In some embodiments, after the aqueous formulation is filtered by a 0.22 micron filter, the amount of cabazitaxel in the filtered aqueous solution is at least 85% of the total amount of cabazitaxel in the aqueous solution before the filtration. In some embodiments, after the aqueous formulation is filtered by a 0.22 micron filter, the amount of cabazitaxel in the filtered aqueous solution is at least 90% of the total amount of cabazitaxel in the aqueous solution before the filtration. In some aspects of these embodiments, the aqueous formulation is filtered by a 0.22-micron filter at a time period selected from 1 hour, 2 hours, 3, hours, 4 hours, 5 hours, 6 hours, 8 hours, 12 hours, 18 hours and 24 hours. In some embodiments, the aqueous formulation is free of solvent other than water. In some embodiments, the aqueous formulation is substantially free of solvent other than water.

Also, provided herein is a pharmaceutical composition comprising the composition consisting essentially of the cabazitaxel and the human serum albumin as described herein, and a pharmaceutically acceptable carrier.

In some embodiments, the pharmaceutical composition further comprises at least one anti-cancer drug (e.g., any one of the anti-cancer drugs as described herein).

In some embodiments, the pharmaceutical composition is free of a surfactant, such as CREMOPHOR® surfactants and Polysorbate 80. In some embodiments, the pharmaceutical composition is substantially free of a surfactant, such as CREMOPHOR® surfactants and Polysorbate 80. In some embodiments, the pharmaceutical composition can be substantially free of a surfactant selected from the group consisting of CREMOPHOR® surfactants and Polysorbate 80.

Also, provided herein is a method of treating a proliferative disease comprising the step of administering to a subject in need thereof a pharmaceutical composition comprising the composition consisting essentially of the cabazitaxel and the human serum albumin as described herein, and a pharmaceutically acceptable carrier.

Also, provided herein is a method of treating a cancer (e.g., any one of cancers described herein), the method comprising the step of administering to a subject in need thereof of a therapeutically effective amount of a pharmaceutical composition comprising the composition consisting essentially of the cabazitaxel and the human serum albumin as described herein, and a pharmaceutically acceptable carrier.

In some embodiments, the cancer is a solid tumor cancer. In some embodiments, the cancer is a prostate cancer.

In some embodiments, the method of treating a prostate cancer comprises the step of administering to a subject in need thereof of a therapeutically effective amount of a pharmaceutical composition comprising the composition consisting essentially of the cabazitaxel and the human serum albumin as described herein, prednisone, and a pharmaceutically acceptable carrier.

In some embodiments, the method of treating cancer (e.g., any one of cancers described herein) comprises the step of administering to a subject in need thereof a therapeutically effective amount of a pharmaceutical composition comprising the composition consisting essentially of the cabazitaxel and the human serum albumin as described herein, and a therapeutically effective amount of at least one inhibitor of the kinases for the treatment of cancer described herein.

In some embodiments, the method of treating cancer (e.g. any one of cancers described herein) comprises the step of administering to a subject in need thereof a therapeutically effective amount of a pharmaceutical composition comprising the composition consisting essentially of the cabazitaxel and the human serum albumin as described herein, and a therapeutically effective amount of at least one anti-cancer drug described herein.

In some embodiments, a composition consisting essentially of the cabazitaxel and the human serum albumin as described herein and an anti-cancer drug are administered simultaneously.

In some embodiments, a composition consisting essentially of the cabazitaxel and the human serum albumin as described herein and an anti-cancer drug are administered consecutively.

The compositions consisting essentially of the cabazitaxel and the human serum albumin described herein can be administered to an individual, such as human, via various routes, such as parenterally, including intravenous, intra-arterial, intraperitoneal, intrapulmonary, oral, inhalation, intravesicular, intramuscular, intra-tracheal, subcutaneous, intraocular, intrathecal, or transdermal. For example, the composition can be administered by inhalation to treat conditions of the respiratory tract. The composition can be used to treat respiratory conditions such as pulmonary fibrosis, broncheolitis obliterans, lung cancer, bronchoalveolar carcinoma, and the like. In some embodiments, the composition is administrated intravenously.

The methods described herein may be performed alone or in conjunction with another therapy, such as surgery, radiation, chemotherapy, immunotherapy, gene therapy, and the like. Additionally, a person having a greater risk of developing the proliferative disease may receive treatments to inhibit or and/or delay the development of the disease.

As will be understood by those of ordinary skill in the art, the appropriate doses of cabazitaxel will be approximately those already employed in clinical therapies wherein cabazitaxel is administered alone or in combination with other chemotherapeutic agents. Variation in dosage will likely occur depending on the condition being treated. Appropriate effective doses will also vary, as recognized by those skilled in the art, depending on the severity of the disease, the route of administration, the sex, age and general health condition of the subject, excipient usage, the possibility of co-usage with other therapeutic treatments such as use of other agents, and the judgment of the treating physician. For example, guidance for selecting an effective dose can be determined by reference to the prescribing information for cabazitaxel.

Methods of Making

Also, provided herein are several methods to prepare a composition comprising non-covalently bound complexes comprising the cabazitaxel and the human serum albumin as described herein, a composition comprising the cabazitaxel and the human serum albumin as described herein, or a composition consisting essentially of the cabazitaxel and the human serum albumin as described herein.

In some embodiments, the method comprises the steps of:
(i) obtaining an organic solution of cabazitaxel in a polar water-miscible organic solvent;
(ii) obtaining a first aqueous solution of human serum albumin; and
(iii) mixing the organic solution of cabazitaxel and the first aqueous solution of human serum albumin to obtain a second aqueous solution comprising the composition comprising cabazitaxel and human serum albumin as described herein.

A non-limiting embodiments of the disclosed methods are as follows.

Formation of the Organic Solution

Cabazitaxel is dissolved in a polar organic solvent (e.g., an alcohol such as methanol, ethanol, isopropanol, and/or n-butanol; THF, $CH_3CN$; DMF; or mixtures thereof) to form an organic solution.

As used herein, the term "organic solution" refers to a solution wherein at least one solvent is a non-aqueous solvent and the weight % of the non-aqueous solvent in the mixture of solvents is at least 50%, at least 60%, at least 70% or at least 90%. In some embodiments, organic solution is a solution in which does not comprise water as a solvent.

In some embodiments, the terms "organic solvent" and "non-aqueous solvent" are used interchangeably and refer to a liquid comprising is at least 50%, at least 60%, at least 70%, at least 90%, or at least 95% of a solvent other than water.

The polar organic solvent is miscible in water. In some embodiments, the polar organic solvent is an alcohol. In some embodiments, the polar organic solvent is ethanol or methanol, or mixtures thereof. For example, the polar organic solvent can be ethanol. In some embodiments, the polar organic solvent is methanol.

In some embodiments, the amount of polar organic solvent is from about 0.05 mL to about 50 mL per mg of cabazitaxel. In some embodiments, the amount of polar organic solvent is from about 0.1 mL to about 20 mL per mg of cabazitaxel. In some embodiments, the amount of polar organic solvent is from about 0.5 mL to about 10 mL per mg of cabazitaxel. In some embodiments, the amount of polar organic solvent is from about 1 mL to about 5 mL per mg of cabazitaxel. In some embodiments, the concentration of cabazitaxel in the polar organic solvent is from about 0.1 mM to about 5 mM, from about 0.1 mM to about 2 mM, from about 0.1 mM to about 1 mM, or from about 0.2 mM to about 1 mM.

Formation of the First Aqueous Solution

A defined amount of human serum albumin is dissolved in an amount of aqueous solvent (e.g., any one of aqueous solvents described herein such as water, 0.9% saline or 5% dextrose) to form a first aqueous solution.

In some embodiments, the amount of aqueous solvent (e.g., water) to prepare the first aqueous solution is from about 1 mL to about 10000 L, from about 2 mL to about 1000 L, from about 3 mL to about 100 L, from about 4 mL to about 10 L, from about 5 mL to about 2 L, from about 6 mL to about 1 L.

In some embodiments, the amount of HSA prepare the first aqueous solution is from about 100 mg to about 1000 kg, from about 150 mg to about 1000 kg, from about 200 mg to about 100 kg, from about 300 mg to about 5 kg, from about 200 mg to about 500 g, or from about 200 mg to about 100 g.

In some embodiments, the amount of aqueous solvent in the first aqueous solution is from about 0.005 mL to about 10 mL per 1 mg of human serum albumin. In some embodiments, the amount of aqueous solvent in the first aqueous solution is from about 0.01 mL to about 5 mL per 1 mg of human serum albumin. In some embodiments, the amount of aqueous solvent in the first aqueous solution is from about 0.01 mL to about 1 mL per 1 mg of human serum albumin. In some embodiments, the amount of aqueous solvent in the first aqueous solution is from about 0.01 mL to about 0.5 mL per 1 mg of human serum albumin. In some embodiments, the amount of aqueous solvent in the first aqueous solution is from about 0.01 mL to about 0.1 mL per 1 mg of human serum albumin. In some embodiments, the amount of aqueous solvent in the first aqueous solution is from about 0.01 mL to about 0.05 mL per 1 mg of human serum albumin. In some embodiments, the amount of aqueous solvent in the first aqueous solution is from about 0.01 mL to about 0.025 mL per 1 mg of human serum albumin. In some embodiments, the amount of aqueous solvent in the first aqueous solution is from about 0.013 mL to about 0.022 mL per 1 mg of human serum albumin. In some embodiments, the amount of aqueous solvent in the first aqueous solution is from about 0.015 mL to about 0.04 mL per 1 mg of human serum albumin. In some embodiments, the amount of aqueous solvent in the first aqueous solution is about 0.007 mL, about 0.01 mL, about 0.015 mL, about 0.02 mL, about 0.025 mL, about 0.03 mL, about 0.035 mL, about 0.04 mL, about 0.045 mL, or about 0.05 mL per 1 mg of human serum albumin. In some embodiments, the amount of aqueous solvent in the first aqueous solution is about 0.02 mL per 1 mg of human serum albumin. In some embodiments, the amount of aqueous solvent (e.g., water) to prepare the first aqueous solution is from about or from about 0.005 mL to about 1 mL, from about 0.015 mL to about 0.5 mL, from about 0.015 mL to about 0.2 mL, from about 0.015 mL to about 0.1 mL, or from about 0.015 mL to about 0.05 mL per 1 mg of HSA. In some embodiments, the amount of aqueous solvent (e.g., water) to prepare the first aqueous solution is about 0.01 mL, about 0.011 mL, about 0.012 mL, about 0.013 mL, about 0.015 mL, about 0.017 mL, about 0.018 mL, about 0.019 mL about 0.02 mL, about 0.021 mL, about 0.022 mL, about 0.023 mL, about 0.024 mL, about 0.025 mL, about 0.026 mL, about 0.027 mL, about 0.028 mL, about 0.029 mL or about 0.03 mL per 1 mg of HSA.

In some embodiments, the amount of HSA in the first aqueous solution is from about 10% w/w to about 25% w/w, or from about 13% w/w to about 22% w/w. In some embodiments, the amount of HSA in the first aqueous solution is about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w or about 25% w/w. In some embodiments, the preparation of the organic solution and the preparation of the first aqueous solution are performed concurrently.

In some embodiments, the preparation of the organic solution and the preparation of the first aqueous solution are performed sequentially. In some embodiments, the preparation of the organic solution is performed before the preparation of the first aqueous solution. In some embodiments, the preparation of the first aqueous solution is performed before the preparation of the organic solution.

In some embodiments, the range of pH in the first aqueous solution is from about 3 to about 9, from about 4 to about 8, from about 5 to about 7, from about 6 to about 7, from about 3 to about 5, from about 3 to about 7, from about 4 to about 6, from about 5 to about 6, or from about 6 to about 6.5. In some embodiments, the pH of the first aqueous solution is about 4, about 5, about 6, about 6.1, about 6.2, about 6.3, about 6.4, about 6.5, about 6.6, about 6.7, about 6.8, about 6.9, about 7, about 7.5, or about 8.

Formation of the Second Aqueous Solution

The organic solution of cabazitaxel is mixed with the first aqueous solution of human serum albumin to form a second aqueous solution. In some embodiments, the second aqueous solution is a clear aqueous solution with no precipitation of cabazitaxel.

In some embodiments, the volume ratio of the amount of aqueous solvent (e.g., water) to the amount of the polar organic solvent (e.g., methanol) is in a range from about 1:1 to about 1000:1. In some embodiments, the volume ratio of the amount of aqueous solvent (e.g., water) to the amount of the polar organic solvent (e.g., methanol) is in a range from about 1.5:1 to about 100:1. In some embodiments, the volume ratio of the amount of aqueous solvent (e.g., water) to the amount of the polar organic solvent (e.g., methanol) is in a range from about 1.5:1 to about 20:1. In some embodiments, the volume ratio of the amount of aqueous solvent (e.g., water) to the amount of the polar organic solvent (e.g., methanol) is in a range from about 1.5:1 to about 10:1. In some embodiments, the volume ratio of the amount of aqueous solvent (e.g., water) to the amount of the polar organic solvent (e.g., methanol) is in a range from about 1:1 to about 10:1. In some embodiments, the volume ratio of the amount of aqueous solvent (e.g., water) to the amount of the polar organic solvent (e.g., methanol) is in a range from about 1:1 to about 3:1. In some embodiments, the volume ratio of the amount of aqueous solvent (e.g., water) to the amount of the polar organic solvent (e.g., methanol) is about 1.5:1, about 2:1, about 2.2:1, about 2.3:1, about 2.4:1, about 2.5:1, about 3:1, about 4:1, about 5:1, about 6:1, about 7:1, about 8:1, about 9:1, or about 10:1.

In some embodiments, the organic solution is added to the first aqueous solution to form a second aqueous solution. In some embodiments, the organic solution is added dropwise to the first aqueous solution to form a second aqueous solution. In some embodiments, the first aqueous solution is added to the organic solution to form a second aqueous solution. In some embodiments, the mixing is performed with agitation. In some embodiments, the mixing is performed with stirring. In some embodiments, the mixing is performed with shaking.

In some embodiments, the addition is done at the temperature from about 0° C. to about 35° C. In some embodiments, the addition is done at the temperature from about 0° C. to about 25° C. In some embodiments, the addition is done at the temperature from about 0° C. to about 10° C. In some embodiments, the addition is done at the temperature about 0° C. In some embodiments, the addition is done at the temperature about 5° C. In some embodiments, the addition is done at the temperature about 10° C. In some embodiments, the addition is done at ambient temperature (e.g., room temperature).

In some embodiments, the time of addition is in a range from about 0.1 min to about 24 hours. In some embodiments, the time of addition is in a range from about 1 min to about 2 hour. In some embodiments, the time of addition is in a range from about 1 min to about 1 hour. In some embodiments, the time of addition is in a range from about 5 min to about 30 min.

In some embodiments, the rate of addition of organic solution to the first aqueous solution is from about 0.01 mL/min to about 100 mL/min, from about 0.02 mL/min to about 50 mL/min, from about 0.05 mL/min to about 20 mL/min, from about 1 mL/min to about 10 mL/min, or from about 0.01 mL/min to about 10 mL/min, from about 0.01 mL/min to about 5 mL/min, from about 0.01 mL/min to about 2 mL/min, from about 0.01 mL/min to about 1 mL/min, from about 0.01 mL/min to about 0.5 mL/min, or from about 0.01 mL/min to about 0.1 mL/min.

In some embodiments, the rate of addition of organic solution to the first aqueous solution is about 0.01 mL/min, 0.02 mL/min, 0.03 mL/min, 0.04 mL/min, 0.05 mL/min, 0.1 mL/min, 0.2 mL/min, 0.3 mL/min, 0.5 mL/min, 0.6 mL/min, 0.8 mL/min, 1 mL/min, 1.5 mL/min, 2 mL/min, 3 mL/min, 5 mL/min or 10 mL/min.

In some embodiments, the range of pH in the second aqueous solution is from about 3 to about 9, from about 4 to about 8, from about 5 to about 7, from about 6 to about 7, from about 3 to about 5, from about 3 to about 7, from about 4 to about 6, from about 5 to about 6, or from about 6 to about 6.5. In some embodiments, the pH of the second aqueous solution is about 4, about 5, about 6, about 6.1, about 6.2, about 6.3, about 6.4, about 6.5, about 6.6, about 6.7, about 6.8, about 6.9, about 7, about 7.5, or about 8.

Optionally, the solvents including both water and organic solvent are removed from the second aqueous solution to provide a solid without removal of organic solvent first. In some embodiments, the solvents are removed under a vacuum. In some embodiments, the solvents are removed using rotary evaporation. In some embodiments, the solvents are removed by lyophilization. In some embodiments, the second aqueous solution was filtered before removal of the solvents.

Removal of Organic Solvent

Upon completion of mixing of the organic solution with the first aqueous solution to form the second aqueous solution, the polar organic solvent is removed from the second aqueous solution.

In some embodiments, the polar organic solvent is removed under reduced pressure. In some embodiments, the polar organic solvent is removed using rotary evaporation. In some embodiments, the polar organic solvent is removed under a vacuum.

In some embodiments, the removal of the polar organic solvent yields a transparent aqueous solution.

Removal of Water from the Second Aqueous Solution

Upon removal of the organic solvent from the second aqueous solution, the water can be removed from the second aqueous solution to provide a solid.

In some embodiments, the second aqueous solution is filtered before removal of water. For example, the second aqueous solution can be filtered by a 0.22 micron filter before removal of water.

As used herein, the term "micron" refers to a unit of measure of one one-thousandth of a millimeter.

In some embodiments, the water is removed under a vacuum. In some embodiments, the water is removed using rotary evaporation. In some embodiments, the water is removed by lyophilization.

In some embodiments, the solvents including both water and organic solvent are removed from the second aqueous solution simultaneously to provide a solid composition. In some embodiments, the solvents are removed under a vacuum. In some embodiments, the solvents are removed using rotary evaporation. In some embodiments, the solvents are removed by lyophilization. In some embodiments, the second aqueous solution was filtered before removal of the solvents.

Reconstitution of the Solid

In some embodiments the solid composition comprising the cabazitaxel and the human serum albumin (e.g., the solid composition prepared by removing organic solvent from the second aqueous solution and removing water from the second aqueous solution) is mixed with a water solution. In some embodiments, the water solution is a saline solution. In some embodiments, the water solution is a 5% dextrose water solution. In some embodiments, the mixing is the addition of the water solution to the solid. In some embodiments, the mixing is the addition of the solid to the water solution. In some embodiments, the mixing reconstitutes the solid. In some embodiments, the mixing yields a clear aqueous solution. In some embodiments, the range of pH in the reconstituted solution is from about 5 to about 8, from about 5 to about 7, from about 6 to about 7, from about 6.5 to about 7.5, from about 4 to about 6, or from about 6 to about 6.5. In some embodiments, the pH of the reconstituted solution is about 5, about 6, about 6.4, about 6.5, about 6.6, about 6.7, about 6.8, about 6.9, about 7, about 7.1, about 7.5, or about 8.

Unless otherwise defined, all technical and scientific terms used herein have the same meaning as commonly understood by one of ordinary skill in the art to which this disclosure belongs. Methods and materials are described herein for use in the present disclosure; other suitable methods and materials known in the art can also be used. The materials, methods, and examples are illustrative only and not intended to be limiting. All publications, patent applications, patents, and other references mentioned herein are incorporated by reference in their entirety. In case of conflict, the present specification, including definitions, will control.

Composition Prepared by the Process

In some embodiments, the present disclosure provides a composition comprising cabazitaxel and human serum albumin, wherein a ratio by weight of cabazitaxel and the human serum albumin in the composition is from about 1:10 to about 1:3000, produced by a method comprising the steps of:

(i) obtaining an organic solution of cabazitaxel in a polar water-miscible organic solvent;

(ii) obtaining a first aqueous solution of human serum albumin; and (iii) mixing the organic solution of cabazitaxel and the first aqueous solution of human serum albumin to obtain a second aqueous solution comprising the composition comprising cabazitaxel and human serum albumin.

In some embodiments, the range of pH in the first aqueous solution is from about 3 to about 9, from about 4 to about 8, from about 5 to about 8, from about 5 to about 7, from about 6 to about 7, from about 3 to about 5, from about 3 to about 7, from about 4 to about 6, or from about 6 to about 6.5. In some embodiments, the pH of the first aqueous solution is about 4, about 5, about 6, about 6.4, about 6.5, about 6.6, about 6.7, about 6.8, about 6.9, about 7, about 7.1, about 7.5, or about 8.

In some embodiments, the range of pH in the second aqueous solution is from about 3 to about 9, from about 4 to about 8, from about 5 to about 8, from about 5 to about 7, from about 6 to about 7, from about 3 to about 5, from about 3 to about 7, from about 4 to about 6, or from about 6 to about 6.5. In some embodiments, the pH of the second aqueous solution is about 4, about 5, about 6, about 6.4, about 6.5, about 6.6, about 6.7, about 6.8, about 6.9, about 7, about 7.1, about 7.5, or about 8.

In some embodiments, the cabazitaxel and the human serum albumin in the composition have a ratio by weight from about 1:100 to about 1:2000. In some embodiments, the cabazitaxel and the human serum albumin in the composition have a ratio by weight from about 1:150 to about 1:1000. In some embodiments, the cabazitaxel and the human serum albumin in the composition have a ratio by weight from about 1:150 to about 1:800. In some embodiments, the cabazitaxel and the human serum albumin in the composition have a ratio by weight from about 1:150 to about 1:600. In some embodiments, the cabazitaxel and the human serum albumin in the composition have a ratio by weight from about 1:150 to about 1:500. In some embodiments, the cabazitaxel and the human serum albumin in the composition have a ratio by weight from about 1:150 to about 1:400. In some embodiments, the cabazitaxel and the human serum albumin in the composition have a ratio by weight from about 1:200 to about 1:1000. In some embodiments, the cabazitaxel and the human serum albumin in the composition have a ratio by weight from about 1:200 to about 1:800. In some embodiments, the cabazitaxel and the human serum albumin in the composition have a ratio by weight from about 1:200 to about 1:600. In some embodiments, the cabazitaxel and the human serum albumin in the composition have a ratio by weight from about 1:200 to about 1:500. In some embodiments, the cabazitaxel and the human serum albumin in the composition have a ratio by weight from about 1:200 to about 1:400. In some embodiments, the cabazitaxel and the human serum albumin in the composition have a ratio by weight from about 1:250 to about 1:1000. In some embodiments, the cabazitaxel and the human serum albumin in the composition have a ratio by weight from about 1:250 to about 1:800. In some embodiments, the cabazitaxel and the human serum albumin in the composition have a ratio by weight from about 1:250 to about 1:600. In some embodiments, the cabazitaxel and the human serum albumin in the composition have a ratio by weight from about 1:250 to about 1:500. In some embodiments, the cabazitaxel and the human serum albumin in the composition have a ratio by weight from about 1:250 to about 1:400. In some embodiments, the cabazitaxel and the human serum albumin in the composition have a ratio by weight from about 1:300 to about 1:600. In some embodiments, the cabazitaxel and the human serum albumin in the composition have a ratio by weight from about 1:300 to about 1:400. In some embodiments, the cabazitaxel and the human serum albumin in the composition have a ratio by weight from about 1:100 to about 1:1000. In some embodiments, the cabazitaxel and the human serum albumin in the composition have a ratio by weight from about 1:220 to about 1:600. In some embodiments, the cabazitaxel and the human serum albumin in the composition have a ratio by weight of about 1:200, 1:210, 1:220, about 1:230, about 1:240, about 1:250, about 1:260, about 1:270, about 1:280, about 1:290, about 1:300, about 1:310, about 1:320, about 1:330, about 1:340, about 1:350, about 1:360, about 1:370, about 1:380, about 1:390, about 1:400, about 1:450, about 1:460, about 1:500 or about 1:600.

In some embodiments, the present disclosure provides a composition comprising cabazitaxel and human serum albumin, wherein the weight ratio of cabazitaxel and the human serum albumin in the composition is from about 1:100 to about 1:3000, produced by a method comprising the steps of:

(i) obtaining an organic solution of cabazitaxel in a polar water-miscible organic solvent;

(ii) obtaining a first aqueous solution of human serum albumin; and (iii) mixing the organic solution of cabazitaxel and the first aqueous solution of human serum albumin to obtain a second aqueous solution comprising the composition comprising cabazitaxel and human serum albumin.

In some embodiments, the range of pH in the first aqueous solution is from about 3 to about 9, from about 4 to about 8, from about 5 to about 8, from about 5 to about 7, from about 6 to about 7, from about 3 to about 5, from about 3 to about 7, from about 4 to about 6, or from about 6 to about 6.5. In some embodiments, the pH of the first aqueous solution is about 4, about 5, about 6, about 6.4, about 6.5, about 6.6, about 6.7, about 6.8, about 6.9, about 7, about 7.1, about 7.5, or about 8.

In some embodiments, the range of pH in the second aqueous solution is from about 3 to about 9, from about 4 to about 8, from about 5 to about 8, from about 5 to about 7, from about 6 to about 7, from about 3 to about 5, from about 3 to about 7, from about 4 to about 6, or from about 6 to about 6.5. In some embodiments, the pH of the second aqueous solution is about 4, about 5, about 6, about 6.4, about 6.5, about 6.6, about 6.7, about 6.8, about 6.9, about 7, about 7.1, about 7.5, or about 8.

In some embodiments, the cabazitaxel can be a pharmaceutically acceptable salt of cabazitaxel. In some embodiments, cabazitaxel can be any one of crystal forms, amorphous forms, solvates and hydrates as described herein.

In some embodiments, the human serum albumin is essentially fatty acid free.

In some embodiments, the composition comprises a non-covalently bound complex comprising cabazitaxel and human serum albumin.

In some embodiments, the amount of the polar water-miscible organic solvent in the organic solution is from about 0.05 mL to about 50 mL per 1 mg of cabazitaxel.

In some embodiments, the amount of the polar water-miscible organic solvent in the organic solution is from about 0.1 mL to about 20 mL per 1 mg of cabazitaxel.

In some embodiments, the amount of the polar water-miscible organic solvent in the organic solution is from about 1 mL to about 5 mL per 1 mg of cabazitaxel.

In some embodiments, the concentration of cabazitaxel in the polar water-miscible organic solvent in the organic solution is from about 0.3 mM to about 1 mM.

In some embodiments, the amount of aqueous solvent in the first aqueous solution is from about 0.005 mL to about 0.05 mL per 1 mg of human serum albumin.

In some embodiments, the amount of aqueous solvent in the first aqueous solution is from about 0.01 mL to about 0.05 mL per 1 mg of human serum albumin.

In some embodiments, the amount of aqueous solvent in the first aqueous solution is from about 0.015 mL to about 0.04 mL per 1 mg of human serum albumin.

In some embodiments, the amount of aqueous solvent in the first aqueous solution is from about 0.01 mL to about 0.025 mL per 1 mg of human serum albumin.

In some embodiments, the amount of aqueous solvent in the first aqueous solution is from about 0.01 mL to about 10 mL per 1 mg of human serum albumin. In some embodiments, the amount of aqueous solvent in the first aqueous solution is from about 0.01 mL to about 5 mL per 1 mg of human serum albumin. In some embodiments, the amount of aqueous solvent in the first aqueous solution is from about 0.01 mL to about 1 mL per 1 mg of human serum albumin. In some embodiments, the amount of aqueous solvent in the first aqueous solution is from about 0.01 mL to about 0.5 mL per 1 mg of human serum albumin. In some embodiments, the amount of aqueous solvent in the first aqueous solution is from about 0.01 mL to about 0.1 mL per 1 mg of human serum albumin. In some embodiments, the amount of aqueous solvent in the first aqueous solution is from about 0.01 mL to about 0.05 mL per 1 mg of human serum albumin. In some embodiments, the amount of aqueous solvent in the first aqueous solution is from about 0.015 mL to about 0.04 mL per 1 mg of human serum albumin. In some embodiments, the amount of aqueous solvent in the first aqueous solution is about 0.01 mL, about 0.015 mL, about 0.02 mL, about 0.025 mL, about 0.03 mL, about 0.035 mL, about 0.04 mL, about 0.045 mL, or about 0.05 mL per 1 mg of human serum albumin. In some embodiments, the amount of aqueous solvent in the first aqueous solution about 0.02 mL per 1 mg of human serum albumin.

In some embodiments, the polar water-miscible organic solvent is an alcohol selected from the group consisting of methanol, ethanol, isopropanol, n-butanol, and mixtures thereof.

In some embodiments, the polar water-miscible organic solvent is selected from methanol, ethanol, and mixtures thereof.

In some embodiments, the polar water-miscible organic solvent is methanol.

In some embodiments, the aqueous solvent is water.

In some embodiments, the mixing comprises adding the organic solution to the first aqueous solution. In some embodiments, wherein the mixing comprises adding the first aqueous solution to the organic solution. In some embodiments, the adding is carried out dropwise. In some embodiments, the adding is carried out for a period of time from several minutes to several hours. In some embodiments, the adding is carried out for a period of time from 2 min to 24 hours. In some embodiments, the adding is carried out for a period of time from 2 min minutes to 12 hours, from 2 min to 6 hours, from 3 min to 3 hours, from 2 min to 1 hour, from 2 min to 30 min, or from 2 min to 25 min.

In some embodiments, the mixing is carried out at a temperature from about 0° C. to about 25° C. In some embodiments, mixing is carried out at ambient temperature (e.g., about 25° C.). In some embodiments, the mixing is carried out at a temperature from about 0° C. to about 5° C. In some embodiments, the mixing is carried out at about 0° C. In some embodiments, the mixing is carried out at ambient temperature (e.g., room temperature).

In some embodiments, the volume ratio of the amount of aqueous solvent to the amount of the organic solvent in the second aqueous solution is in a range from about 2:1 to about 3:1 (e.g., from about 2.2:1 to about 2.4:1).

In some embodiments, the volume ratio of the amount of aqueous solvent to the amount of the organic solvent in the second aqueous solution is in a range from about 1:1 to about 1000:1. In some embodiments, the volume ratio of the amount of aqueous solvent to the amount of the organic solvent in the second aqueous solution is in a range from about 1.5:1 to about 100:1. In some embodiments, the volume ratio of the amount of aqueous solvent to the amount of the organic solvent in the second aqueous solution is in a range from about 1.5:1 to about 20:1. In some embodiments, the volume ratio of the amount of aqueous solvent to the amount of the organic solvent in the second aqueous solution is in a range from about 1.5:1 to about 10:1. In some embodiments, the volume ratio of the amount of aqueous solvent to the amount of the organic solvent in the second aqueous solution is in a range from about 2:1 to about 10:1. In some embodiments, the volume ratio of the amount of aqueous solvent to the amount of the organic solvent in the second aqueous solution is about 1.5:1, about 2:1, about 2.2:1, about 2.3:1, about 2.4:1, about 2.5:1, about 3:1, about 4:1, about 5:1, about 6:1, about 7:1, about 8:1, about 9:1, or about 10:1. In some embodiments, the aqueous solvent is water. In some embodiments, the aqueous solvent is water and the organic solvent is an alcohol. In some embodiments, the aqueous solvent is water and the organic solvent is methanol. In some embodiments, the aqueous solvent is water and the organic solvent is methanol, and the volume ration of water to methanol is from about 2:1 to about 2.5:1.

In some embodiments, the composition further comprises removing the polar water-miscible organic solvent from the second aqueous solution to obtain a third aqueous solution comprising the composition comprising cabazitaxel and human serum albumin. In some embodiments, the composition comprises removing aqueous solvent from the third aqueous solution to obtain the composition comprising cabazitaxel and human serum albumin.

In some embodiments, the composition further comprises removing the organic solvent (e.g. methanol) and the aqueous solvent (e.g., water) from the second aqueous solution to obtain the composition comprising cabazitaxel and human serum albumin.

In some embodiments, the removing as carried out in vacuum (e.g., using the rotovap). In some embodiments, the removing is carried out by lyophilization.

In some embodiments, the composition forms a clear aqueous solution when the composition is dissolved in an aqueous solvent, and wherein the solubility of the composition in the aqueous solution is at least 10 mg/mL.

In some embodiments, the composition is a solid formulation

In some embodiments, the composition is an aqueous formulation. In some embodiments, the aqueous formulation is substantially free of solvent other than water. In some embodiments, the aqueous formulation is free of a surfactant. In some embodiments, the surfactant is selected from the group consisting of CREMOPHOR® surfactants and Polysorbate 80. In some embodiments, the aqueous formulation is a clear aqueous solution. In some embodiments, the aqueous formulation is a clear aqueous solution for at least 2 hours, at least 4 hours, at least 6 hours, at least 8 hours, at least 24 hours, at least 48 hours, or at least 72 hours.

In some embodiments, the present disclosure provides a pharmaceutical composition comprising the composition as prepared by a process as described herein, and a pharmaceutically acceptable carrier.

In some embodiments, the present disclosure provides a method of treating a cancer, the method comprising the step of administering to a subject in need thereof a therapeutically effective amount of the pharmaceutical composition as described herein.

In some embodiments, the cancer is a solid tumor. In some embodiments, the cancer is a prostate cancer.

EXAMPLES

HPLC analysis: The HPLC system used herein is a SHIMADZU LC-10AT vp series system, which consists of a SHIMADZU LC-10AT vp pump, a manual injector, a SHIMADZU CTO-10AS vp column oven, a SHIMADZU SPD-10A vp wavelength detector, and a SHIMADZU LC solution workstation. Waters XTERRA RP10 column (4.6 mm×150 mm, 5 µm) is used as an analytical column. The column oven temperature is 30° C. Mobile phase is composed of methanol and water (70:30 v/v) and pumped at a flow rate of 1 ml/minute. The effluent is detected at a wavelength of 233 nm using a UV detector. The sample injection amount is 20 µl.

Example 1

Composition Comprising Cabazitaxel and Human Serum Albumin (HSA)

The ratio by weight of cabazitaxel to HSA prepared was about 1:300.

Cabazitaxel (4 mg) was dissolved in methanol (10 mL) in a flask to give a clear solution. HSA (1200 mg) (native fatty acid free human serum albumin purchased from SeraCare Life Sciences, product code: HS-455-80, which contains fatty acids <0.2 mg/gm) was dissolved in 22 ml of water in a round bottom flask. The methanol solution of cabazitaxel was added slowly dropwise into the flask of the HSA solution with rapid stirring. Upon completion of the addition, a clear solution was obtained. The methanol was removed under vacuum until the volume of the solution was about 20 mL to give a clear solution. The clear aqueous solution was filtered by a 0.22 micron aqueous phase filter. The resulting clear aqueous solution was lyophilized overnight to give a white solid.

A sample of 100 mg of the lyophilized solid was reconstituted by adding 2 mL water to give a clear aqueous solution. This clear aqueous solution stays clear and is free of visible precipitation of the undissolved cabazitaxel when visually observed after 6 hours at room temperature. This clear aqueous solution stays clear and is free of visible precipitation of the undissolved cabazitaxel when visually observed after 24 hours at room temperature. This clear aqueous solution stays clear and is free of visible precipitation of the undissolved cabazitaxel when visually observed after 3 days at room temperature.

A sample of 100 mg of the lyophilized solid was reconstituted by adding 2 mL water to give a clear aqueous solution. This clear aqueous solution stays clear and is free of visible precipitation of the undissolved cabazitaxel when visually observed after 6 hours at 4° C. This clear aqueous solution stays clear and is free of visible precipitation of the undissolved cabazitaxel when visually observed after 24 hours at 4° C. This clear aqueous solution stays clear and is free of visible precipitation of the undissolved cabazitaxel when visually observed after 3 days at 4° C.

Example 2

Composition Comprising Cabazitaxel and Human Serum Albumin (Recombinant Human Serum Albumin)

The ratio by weight of cabazitaxel to recombinant human serum albumin prepared was about 1:300.

Cabazitaxel (2 mg) was dissolved in methanol (5 mL) in a flask to give a clear solution. Recombinant human serum albumin (600 mg) (fatty acid free recombinant human serum albumin (no fatty acids detected) purchased from Wuhan Healthgen Biotechnology Corp.) was dissolved in 12 mL of water in a round bottom flask. The methanol solution of cabazitaxel was added slowly dropwise into the flask of the recombinant human serum albumin solution with rapid stirring. Upon completion of the addition, a clear solution was obtained. The methanol was removed under vacuum until the volume of the solution was about 10 mL to give a clear solution. The clear aqueous solution was filtered by a 0.22 micron aqueous phase filter. The resulting clear aqueous solution was lyophilized overnight to give a white solid.

A sample of 100 mg of the lyophilized solid was reconstituted by adding 2 mL water to give a clear aqueous solution. This clear aqueous solution stays clear and is free of visible precipitation of the undissolved cabazitaxel when visually observed after 6 hours at room temperature. This clear aqueous solution stays clear and is free of visible precipitation of the undissolved cabazitaxel when visually observed after 24 hours at room temperature. This clear aqueous solution stays clear and is free of visible precipitation of the undissolved cabazitaxel when visually observed after 3 days at room temperature.

A sample of 100 mg of the lyophilized solid was reconstituted by adding 2 mL water to give a clear aqueous solution. This clear aqueous solution stays clear and is clear of visible precipitation of the undissolved cabazitaxel when visually observed after 6 hours at 4° C. This clear aqueous solution stays clear and is free of visible precipitation of the undissolved cabazitaxel when visually observed after 24 hours at 4° C. This clear aqueous solution stays clear and is free of visible precipitation of the undissolved cabazitaxel when visually observed after 3 days at 4° C.

Example 3

Composition Comprising Cabazitaxel and Human Serum Albumin (HSA)

The ratio by weight of cabazitaxel to HSA prepared was about 1:350.

Cabazitaxel (2 mg) was dissolved in methanol (6 mL) in a flask to give a clear solution. HSA (700 mg) (native fatty acid free human serum albumin purchased from SeraCare Life Sciences, product code: HS-455-80, which contains fatty acids <0.2 mg/gm) was dissolved in 14 mL of water in a round bottom flask. The methanol solution of cabazitaxel was added slowly dropwise into the flask of the HSA solution with rapid stirring. Upon completion of the addition, a clear solution was obtained. The methanol was removed under vacuum until the volume of the solution was about 12 mL to give a clear solution. The clear aqueous solution was filtered by a 0.22 micron aqueous phase filter. The resulting clear aqueous solution was lyophilized overnight to give a white solid.

A sample of 100 mg of the lyophilized solid was reconstituted by adding 2 mL water to give a clear aqueous solution. This clear aqueous solution stays clear and is free of visible precipitation of the undissolved cabazitaxel when visually observed after 6 hours at room temperature. This clear aqueous solution stays clear and is free of visible precipitation of the undissolved cabazitaxel when visually observed after 24 hours at room temperature. This clear aqueous solution stays clear and is free of visible precipitation of the undissolved cabazitaxel when visually observed after 3 days at room temperature.

A sample of 100 mg of the lyophilized solid was reconstituted by adding 2 mL water to give a clear aqueous solution. This clear aqueous solution stays clear and is free of visible precipitation of the undissolved cabazitaxel when visually observed after 6 hours at 4° C. This clear aqueous solution stays clear and is free of visible precipitation of the undissolved cabazitaxel when visually observed after 24 hours at 4° C. This clear aqueous solution stays clear and is free of visible precipitation of the undissolved cabazitaxel when visually observed after 3 days at 4° C.

Example 4

Composition Comprising Cabazitaxel and Human Serum Albumin (HSA)

The ratio by weight of cabazitaxel to HSA prepared was about 1:250.

Cabazitaxel (2 mg) was dissolved in methanol (4.2 mL) in a flask to give a clear solution. HSA (500 mg) (native fatty acid free human serum albumin purchased from SeraCare Life Sciences, product code: HS-455-80, which contains fatty acids <0.2 mg/gm) was dissolved in 10 mL of water in a round bottom flask. The methanol solution of cabazitaxel was added slowly dropwise into the flask of the HSA solution with rapid stirring. Upon completion of the addition, a clear solution was obtained. The methanol was removed under vacuum until the volume of the solution was about 8-9 mL to give a clear solution. The clear aqueous solution was filtered by a 0.22 micron aqueous phase filter. The resulting clear aqueous solution was lyophilized overnight to give a white solid.

A sample of 100 mg of the lyophilized solid was reconstituted by adding 2 mL water to give a clear aqueous solution. This clear aqueous solution stays clear and is free of visible precipitation of the undissolved cabazitaxel when visually observed after 6 hours at room temperature. This clear aqueous solution stays clear and is free of visible precipitation of the undissolved cabazitaxel when visually observed after 24 hours at room temperature. This clear aqueous solution stays clear and is free of visible precipitation of the undissolved cabazitaxel when visually observed after 3 days at room temperature.

A sample of 100 mg of the lyophilized solid was reconstituted by adding 2 mL water to give a clear aqueous solution. This clear aqueous solution stays clear and is free of visible precipitation of the undissolved cabazitaxel when visually observed after 6 hours at 4° C. This clear aqueous solution stays clear and is free of visible precipitation of the undissolved cabazitaxel when visually observed after 24 hours at 4° C. This clear aqueous solution stays clear and is free of visible precipitation of the undissolved cabazitaxel when visually observed after 3 days at 4° C.

Example 5

Composition Comprising Cabazitaxel and Human Serum Albumin (Recombinant Human Serum Albumin)

The ratio by weight of cabazitaxel to recombinant human serum albumin prepared was about 1:400.

Cabazitaxel (1 mg) was dissolved in methanol (3.4 mL) in a flask to give a clear solution. Recombinant human serum albumin (400 mg) (fatty acid free recombinant human serum albumin (no fatty acids detected) purchased from Wuhan Healthgen Biotechnology Corp.) was dissolved in 8 mL of water in a round bottom flask. The methanol solution of cabazitaxel was added slowly dropwise into the flask of the recombinant human serum albumin solution with rapid stirring. Upon completion of the addition, a clear solution was obtained. The methanol was removed under vacuum until the volume of the solution was about 7 mL to give a clear solution. The clear aqueous solution was filtered by a 0.22 micron aqueous phase filter. The resulting clear aqueous solution was lyophilized overnight to give a white solid.

A sample of 100 mg of the lyophilized solid was reconstituted by adding 2 mL water to give a clear aqueous solution. This clear aqueous solution stays clear and is free of visible particles or precipitation of the undissolved cabazitaxel when visually observed after 6 hours at room temperature. This clear aqueous solution stays clear and is free of visible precipitation of the undissolved cabazitaxel when visually observed after 24 hours at room temperature. This clear aqueous solution stays clear and is free of visible precipitation of the undissolved cabazitaxel when visually observed after 3 days at room temperature.

A sample of 100 mg of the lyophilized solid was reconstituted by adding 2 mL water to give a clear aqueous solution. This clear aqueous solution stays clear and is free of visible precipitation of the undissolved cabazitaxel when visually observed after 6 hours at 4° C. This clear aqueous solution stays clear and is free of visible precipitation of the undissolved cabazitaxel when visually observed after 24 hours at 4° C. This clear aqueous solution stays clear and is free of visible precipitation of the undissolved cabazitaxel when visually observed after 3 days at 4° C.

Example 6

Composition Comprising Cabazitaxel and Human Serum Albumin (HSA)

The ratio by weight of cabazitaxel to HSA prepared was about 1:600.

Cabazitaxel (1 mg) was dissolved in methanol (4.2 mL) in a flask to give a clear solution. HSA (600 mg) (native human serum albumin purchased from Golden West Biologicals, Inc., catalog #: HA1000) was dissolved in 10 mL of water in a round bottom flask. The methanol solution of cabazitaxel was added slowly dropwise into the flask of the HSA solution with rapid stirring. Upon completion of the addition, a clear solution was obtained. The methanol was removed under vacuum until the volume of the solution was about 8-9 mL to give a clear solution. The clear aqueous solution was filtered by a 0.22 micron aqueous phase filter. The resulting clear aqueous solution was lyophilized overnight to give a white solid.

A sample of 100 mg of the lyophilized solid was reconstituted by adding 2 mL water to give a clear aqueous solution. This clear aqueous solution stays clear and is free of visible particles or precipitation of the undissolved cabazitaxel when visually observed after 6 hours at room temperature. This clear aqueous solution stays clear and is free of visible precipitation of the undissolved cabazitaxel when visually observed after 24 hours at room temperature. This clear aqueous solution stays clear and is free of visible precipitation of the undissolved cabazitaxel when visually observed after 3 days at room temperature.

A sample of 100 mg of the lyophilized solid was reconstituted by adding 2 mL water to give a clear aqueous solution. This clear aqueous solution stays clear and is free of visible precipitation of the undissolved cabazitaxel when visually observed after 6 hours at 4° C. This clear aqueous solution stays clear and is free of visible precipitation of the undissolved cabazitaxel when visually observed after 24 hours at 4° C. This clear aqueous solution stays clear and is free of visible precipitation of the undissolved cabazitaxel when visually observed after 3 days at 4° C.

Example 7

Measure the Correlation Between HPLC Peak Area and the Cabazitaxel Concentration Methanol solutions of cabazitaxel in 8 different concentrations, 0.025 mg/mL, 0.0375 mg/mL, 0.05 mg/mL. 0.075 mg/mL, 0.1 mg/mL, 0.15 mg/mL, 0.2 mg/mL and 0.25 mg/mL, were prepared. The 8 cabazitaxel methanol solutions were analyzed in HPLC. The peak area and concentration of cabazitaxel were correlated using linear regression. The linear regression data is shown as below.

$Y(\text{peak area})=8680+2.854E7*X(\text{concentration})$,
$R=0.99998, P<0.0001$.

Example 8

Measure the Absorption of the Composition Comprising the Cabazitaxel and HSA by the 0.22 Micron Aqueous Phase Filter in the Filtration 300 mg of the lyophilized powder from the example 1 (the ratio by weight of cabazitaxel to HSA is about 1:300) was dissolved in 6 mL of water to form a clear solution. To this clear aqueous solution, 1 mL solution was taken out to give the solution F0; additional 1 mL solution was taken out and filtered by a 0.22 micron aqueous phase filter to give the solution F1; additional 1 mL solution was taken out and filtered through the same 0.22 micron aqueous phase filter used for the solution F1 to give the solution F2; additional 1 mL solution was taken out and filtered through the same 0.22 micron aqueous phase filter used for the solutions F1 and F2 to give the solution F3; additional 1 mL solution was taken out and filtered by the same 0.22 micron aqueous phase filter used for the solutions F1, F2, and F3 to give the solution F4; and additional 1 mL solution was taken out and filtered by the same 0.22 micron aqueous phase filter used for the solutions F1, F2, F3, and F4 to give the solution F5;

To 200 µl of the solutions F0, F1, F2, F3, F4, and F5 were added 800 µl of acetonitrile. The mixtures were vortexed for seconds and then centrifuged at 4,000 g for 5 minutes. The supernatants were removed and collected followed by injection on HPLC. Based on the HPLC data, the concentrations of the solutions of F0, F1, F2, F3, F4, and F5 have been calculated and shown in the Table 1. The concentration of the solution F1 is significantly lower than the concentration of the solution of F0, which indicated that the filter membrane absorption was very significant in the beginning. The concentrations of the follow-up solutions F2, F3, F4, and F5 were increasing, which indicated that the filter membrane absorption became saturated.

TABLE 1

| Solution Number | Concentration (mg/mL) |
|---|---|
| F0 | 0.1419 |
| F1 | 0.1147 |
| F2 | 0.1400 |
| F3 | 0.1417 |
| F4 | 0.1423 |
| F5 | 0.1424 |

Example 9

Measure the Cabazitaxel Concentrations in the Clear Aqueous Solutions Before and After the Filtration at 0 Hour, 6 Hours, 24 Hours, and 72 Hours Cabazitaxel (20 mg) was dissolved in methanol (43 mL) in a flask to give a clear solution. HSA (6 g) (native fatty acid free human serum albumin purchased from SeraCare Life Sciences, product code: HS-455-80, which contains fatty acids <0.2 mg/gm) was dissolved in 100 mL of water in a round bottom flask. The methanol solution of cabazitaxel was added slowly dropwise into the flask of the HSA solution at 0° C. with stirring. Upon completion of the addition, a clear solution was obtained. The methanol was removed under vacuum to give a clear solution. The clear aqueous solution was filtered by a 0.22 micron aqueous phase filter. The resulting clear aqueous solution was lyophilized overnight to give a white solid.

4 vials each with 300 mg of the lyophilized solid were added with 6 mL of water. After the lyophilized solid was dissolved in water, one vial was used for the experiment immediately, and other 3 vials were keep in the room temperature and used for the experiment in the 3 different time points, 6 hours, 24 hours, and 72 hours. For the vial used the immediately, 1 mL of the solution was taken out from the 6 mL transparent aqueous solution to give the solution CA-0-0h, and the remaining 5 mL of the solution was filtered by the same 0.22 micron aqueous phase filter at 1 mL at a time to give the solutions CA-1-0h, CA-2-0h, CA-3-0h, CA-4-0h, and CA-5-0h, similar to the method used in the example 8. To 200 µl of the solutions CA-0-0h and CA-5-0h were added 800 µl of acetonitrile separately. The mixtures were vortexed for seconds and then centrifuged at 4,000 g for 5 minutes. The supernatants were removed and collected followed by injection on HPLC. The same procedure was repeated 2 more times for each of solutions CA-0-0h and CA-5-0h. Based on the HPLC data, the concentrations of the solutions of CA-0-0h, and CA-5-0h have been calculated and shown in the Table 2. At 0 hour, the concentration of the clear aqueous solution after the filtration was about 98.6% of the concentration of the clear aqueous solution before the filtration.

TABLE 2

| Solution Number | Concentration (mg/mL) | Average Concentration (mg/mL) |
|---|---|---|
| CA-0-0h-1 | 0.1461 | 0.1460 |
| CA-0-0h-2 | 0.1460 | |
| CA-0-0h-3 | 0.1458 | |
| CA-5-0h-1 | 0.1438 | 0.1440 |
| CA-5-0h-1 | 0.1438 | |
| CA-5-0h-1 | 0.1445 | |

At 6 hours, the experiments were done for the second 6 mL of the clear aqueous solution using the same protocol as for the first 6 mL of the transparent aqueous solution at 0 hour. Based on the HPLC data, the concentrations of the solutions of CA-0-6h, and CA-5-6h have been calculated and shown in the Table 3. At 6 hours, the concentration of the clear aqueous solution after the filtration was about 96.9% of the concentration of the clear aqueous solution before the filtration.

TABLE 3

| Solution Number | Concentration (mg/mL) | Average Concentration (mg/mL) |
|---|---|---|
| CA-0-6h-1 | 0.1480 | 0.1482 |
| CA-0-6h-2 | 0.1484 | |
| CA-0-6h-3 | 0.1482 | |
| CA-5-6h-1 | 0.1434 | 0.1436 |
| CA-5-6h-1 | 0.1441 | |
| CA-5-6h-1 | 0.1433 | |

At 24 hours, the experiments were done for the third 6 mL of the clear aqueous solution using the same protocol as for the first 6 mL of the transparent aqueous solution at 0 hour. Based on the HPLC data, the concentrations of the solutions of CA-0-24h, and CA-5-24h have been calculated and shown in the Table 4. At 24 hours, the concentration of the clear aqueous solution after the filtration was about 97.8% of the concentration of the clear aqueous solution before the filtration.

TABLE 4

| Solution Number | Concentration (mg/mL) | Average Concentration (mg/mL) |
|---|---|---|
| CA-0-24h-1 | 0.1436 | 0.1436 |
| CA-0-24h-2 | 0.1429 | |
| CA-0-24h-3 | 0.1444 | |
| CA-5-24h-1 | 0.1406 | 0.1405 |
| CA-5-24h-1 | 0.1407 | |
| CA-5-24h-1 | 0.1402 | |

At 72 hours, the experiments were done for the 4th 6 mL of the clear aqueous solution using the same protocol as for the first 6 mL of the transparent aqueous solution at 0 hour. Based on the HPLC data, the concentrations of the solutions of CA-0-72h, and CA-5-72h have been calculated and shown in the Table 5. At 72 hours, the concentration of the clear aqueous solution after the filtration was about 98.8% of the concentration of the clear aqueous solution before the filtration.

TABLE 5

| Solution Number | Concentration (mg/mL) | Average Concentration (mg/mL) |
|---|---|---|
| CA-0-72h-1 | 0.1447 | 0.1445 |
| CA-0-72h-2 | 0.1450 | |
| CA-0-72h-3 | 0.1437 | |
| CA-5-72h-1 | 0.1429 | 0.1428 |
| CA-5-72h-1 | 0.1422 | |
| CA-5-72h-1 | 0.1433 | |

Example 10

Composition Comprising Cabazitaxel and Human Serum Albumin (HSA)

The ratio by weight of cabazitaxel to HSA prepared was about 1:220.

Cabazitaxel (2 mg) was dissolved in methanol (3.9 mL) in a glass vial to give a clear solution. HSA (440 mg) (native fatty acid free human serum albumin purchased from Sera-Care Life Sciences, product code: HS-455-80, which contains fatty acids <0.2 mg/gm) as a powder was dissolved in 9 mL of water in a round bottom flask. The methanol solution of cabazitaxel was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a cloudy solution.

Example 11

Composition Comprising Cabazitaxel and Human Serum Albumin (HSA)

The ratio by weight of cabazitaxel to HSA prepared was about 1:240.

Cabazitaxel (2 mg) was dissolved in methanol (3.9 mL) in a glass vial to give a clear solution. HSA (480 mg) (native fatty acid free human serum albumin purchased from Sera-Care Life Sciences, product code: HS-455-80, which contains fatty acids <0.2 mg/gm) as a powder was dissolved in 9 mL of water in a round bottom flask. The methanol solution of cabazitaxel was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a clear solution.

Example 12

Composition Comprising Cabazitaxel and Human Serum Albumin (HSA)

The ratio by weight of cabazitaxel to HSA prepared was about 1:400.

Cabazitaxel (1 mg) was dissolved in methanol (3.4 mL) in a vial to give a clear solution. A solution of HSA (400 mg, 2 mL) (20% human serum albumin solution for infusion (product name: AlbuRx) from CSL Behring) was added into 6 mL of water to give a HSA solution (8 mL) in a round bottom flask. The methanol solution of cabazitaxel was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a clear solution. White precipitation was formed in the solution in 2 hours.

Example 13

Composition Comprising Cabazitaxel and Human Serum Albumin (HSA)

The ratio by weight of cabazitaxel to HSA prepared was about 1:460.

Cabazitaxel (1 mg) was dissolved in methanol (3.9 mL) in a vial to give a clear solution. A solution of HSA (460 mg, 2.3 mL) (20% human serum albumin solution for infusion (product name: AlbuRx) from CSL Behring) was added into 6.9 mL of water to give a HSA solution (9.2 mL) in a round bottom flask. The methanol solution of cabazitaxel was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a clear solution. The clear aqueous solution stayed clear without precipitation after 24 hours.

Example 14

Composition Comprising Cabazitaxel and Human Serum Albumin (HSA)

The ratio by weight of cabazitaxel to HSA prepared was about 1:250.

Cabazitaxel (20 mg) was dissolved in methanol (28.3 mL) in a glass vial to give a clear solution. HSA (5 g) (native fatty acid free human serum albumin purchased from SeraCare Life Sciences, product code: HS-455-80, which contains fatty acids <0.2 mg/gm) as a powder was dissolved in 66 mL of water in a round bottom flask. The methanol solution of cabazitaxel was added slowly dropwise into the flask of the HSA solution with rapid stirring at 0° C. Upon completion of the addition, a clear solution was obtained. Then, the methanol in the solution was removed under vacuum to give a clear solution. The clear aqueous solution was filtered by a 0.22 micron aqueous phase filter. The resulting clear aqueous solution was lyophilized overnight to give a white solid.

A sample of 100 mg of the lyophilized solid was reconstituted by adding 2 mL water to give a clear solution.

Example 15

Composition Comprising Cabazitaxel and Human Serum Albumin (HSA)

The ratio by weight of cabazitaxel to HSA prepared was about 1:300.

Cabazitaxel (15 mg) was dissolved in methanol (25.7 mL) in a glass vial to give a clear solution. HSA (4.5 g) (native fatty acid free human serum albumin purchased from Sera-Care Life Sciences, product code: HS-455-80, which contains fatty acids <0.2 mg/gm) as a powder was dissolved in 60 mL of water in a round bottom flask. The methanol solution of cabazitaxel was added slowly dropwise into the flask of the HSA solution with rapid stirring at 0° C. Upon completion of the addition, a clear solution was obtained. Then, the methanol in the solution was removed under vacuum to give a clear solution. The clear aqueous solution was filtered by a 0.22 micron aqueous phase filter. The resulting clear aqueous solution was lyophilized overnight to give a white solid.

A sample of 100 mg of the lyophilized solid was reconstituted by adding 2 mL water to give a clear solution.

Example 16

Composition Comprising Cabazitaxel and Human Serum Albumin (HSA)

The ratio by weight of cabazitaxel to HSA prepared was about 1:330.

Cabazitaxel (15 mg) was dissolved in methanol (28.3 mL) in a glass vial to give a clear solution. HSA (4.95 g) (native fatty acid free human serum albumin purchased from Sera-Care Life Sciences, product code: HS-455-80, which contains fatty acids <0.2 mg/gm) as a powder was dissolved in 66 mL of water in a round bottom flask. The methanol solution of cabazitaxel was added slowly dropwise into the flask of the HSA solution with rapid stirring at 0° C. Upon completion of the addition, a clear solution was obtained. Then, the methanol in the solution was removed under vacuum to give a clear solution. The clear aqueous solution was filtered by a 0.22 micron aqueous phase filter. The resulting clear aqueous solution was lyophilized overnight to give a white solid.

A sample of 100 mg of the lyophilized solid was reconstituted by adding 2 mL water to give a clear solution.

Example 17

Measure pH Value of the Clear Aqueous Solution of Composition Comprising Cabazitaxel and Human Serum Albumin (HSA)

250 mg of the lyophilized solid of the composition comprising cabazitaxel and HSA (the ratio by weight about 1:330) from Example 16 was dissolved in 10 mL of water to give a clear aqueous solution. The clear aqueous solution was kept at about 25° C. and measured for pH value. The pH value of the clear aqueous solution is 6.87 (3 measurements: 6.88, 6.87, and 6.86).

500 mg of the lyophilized solid of the composition comprising cabazitaxel and HSA (the ratio by weight about 1:330) from Example 16 was dissolved in 10 mL of water to give a clear aqueous solution. The clear aqueous solution was kept at about 25° C. and measured for pH value. The pH value of the clear aqueous solution is 6.80 (3 measurements: 6.80, 6.81, and 6.80).

250 mg of the lyophilized solid of the composition comprising cabazitaxel and HSA (the ratio by weight about 1:330) from Example 16 was dissolved in 10 mL of 0.9% saline solution, which had pH value about 5.41, to give a clear aqueous solution. The clear aqueous solution was kept at about 25° C. and measured for pH value. The pH value of the clear aqueous solution is 6.76 (3 measurements: 6.76, 6.76, and 6.77).

250 mg of the lyophilized solid of the composition comprising cabazitaxel and HSA (the ratio by weight about 1:330) from Example 16 was dissolved in 10 mL of 5% dextrose solution, which had pH value about 4.40, to give a clear aqueous solution. The clear aqueous solution was kept at about 25° C. and measured for pH value. The pH value of the clear aqueous solution is 6.79 (3 measurements: 6.78, 6.79, and 6.79).

Example 18

Measure pH Value of the Clear Aqueous Solution of Composition Comprising Cabazitaxel and Human Serum Albumin (HSA)

500 mg of the lyophilized solid of the composition comprising cabazitaxel and HSA (the ratio by weight about 1:250) from Example 14 was dissolved in 10 mL of water to give a clear aqueous solution. The clear aqueous solution was kept at about 25° C. and measured for pH value. The pH value of the clear aqueous solution is 6.76 (3 measurements: 6.77, 6.76, and 6.74).

Example 19

Measure the Cabazitaxel Concentrations in the Clear Aqueous Solutions Before and After the Filtration at 0 Hour, and after the Filtration at 1 Hour, 2 Hours, 3 Hours, 4 Hours, 5 Hours, 6 Hours, and 24 Hours 2.5 g of the lyophilized solid of the composition comprising cabazitaxel and HSA (the ratio by weight about 1:330) from Example 16 was dissolved in 50 mL of water to give a clear aqueous solution, which was kept at about 20° C. Immediately after the lyophilized solid was dissolved in water, 6 mL of the clear aqueous solution was taken out from the 50 mL solution. Then 1 mL of the solution was taken out from the 6 mL clear aqueous solution to give the solution CA-0-0h, and the remaining 5 mL of the solution was filtered by the same 0.22 micron aqueous phase filter at 1 mL at a time to give the solutions CA-1-0h, CA-2-0h, CA-3-0h, CA-4-0h, and CA-5-0h. To 200 µl of the solutions CA-0-0h and CA-5-0h were added 800 µl of acetonitrile separately. The mixtures were vortexed for seconds and then centrifuged at 4,000 g for 5 minutes. The supernatants were removed and collected followed by injection on HPLC. The same procedure was repeated 2 more times for each of solutions CA-0-0h and CA-5-0h. Based on the HPLC data and the measurement data of Example 7, the cabazitaxel concentrations of the solutions of CA-0-0h, and CA-5-0h have been calculated and shown in the Table 6. At 0 hour, the cabazitaxel concentration of the clear aqueous solution after the filtration was about 99.63% of the cabazitaxel concentration of the clear aqueous solution before the filtration.

TABLE 6

| Solution Number | Cabazitaxel Concentration (mg/mL) | Average Cabazitaxel Concentration (mg/mL) |
|---|---|---|
| CA-0-0h-1 | 0.1367 | 0.1366 |
| CA-0-0h-2 | 0.1367 | |
| CA-0-0h-3 | 0.1363 | |

TABLE 6-continued

| Solution Number | Cabazitaxel Concentration (mg/mL) | Average Cabazitaxel Concentration (mg/mL) |
|---|---|---|
| CA-5-0h-1 | 0.1357 | 0.1361 |
| CA-5-0h-2 | 0.1365 | |
| CA-5-0h-3 | 0.1361 | |

At 1 hour, 5 mL of the clear aqueous solution was taken out from the remaining 44 mL of the aqueous solution. Then 1 mL of the solution was taken out from the 5 mL clear aqueous solution and filtered by a 0.22 micron aqueous phase filter to give the solution CA-1-1h, and the remaining 4 mL of the solution was filtered by the same 0.22 micron aqueous phase filter at 1 mL at a time to give the solutions CA-2-1h, CA-3-1h, CA-4-1h, and CA-5-1h. To 200 µl of the solution CA-5-1h was added 800 µl of acetonitrile. The mixture was vortexed for seconds and then centrifuged at 4,000 g for 5 minutes. The supernatant was removed and collected followed by injection on HPLC. The same procedure was repeated 2 more times for the solution CA-5-1h. Based on the HPLC data and the measurement data of Example 7, the cabazitaxel concentrations of the solution CA-5-1h have been calculated and shown in the Table 7. At 1 hour, the cabazitaxel concentration of the clear aqueous solution after the filtration was about 99.63% of the cabazitaxel concentration of the clear aqueous solution at 0 hour before the filtration.

TABLE 7

| Solution Number | Cabazitaxel Concentration (mg/mL) | Average Cabazitaxel Concentration (mg/mL) |
|---|---|---|
| CA-5-1h-1 | 0.1362 | 0.1361 |
| CA-5-1h-2 | 0.1363 | |
| CA-5-1h-3 | 0.1359 | |

At 2 hours, 5 mL of the clear aqueous solution was taken out from the remaining 39 mL of the aqueous solution. The experiments were done for the 5 mL of the clear aqueous solution taken out at 2 hours using the same protocol as for the 5 mL of the clear aqueous solution taken out at 1 hour. Based on the HPLC data and the measurement data of Example 7, the cabazitaxel concentrations of the solution CA-5-2h have been calculated and shown in the Table 8. At 2 hours, the cabazitaxel concentration of the clear aqueous solution after the filtration was about 99.41% of the cabazitaxel concentration of the clear aqueous solution at 0 hour before the filtration.

TABLE 8

| Solution Number | Cabazitaxel Concentration (mg/mL) | Average Cabazitaxel Concentration (mg/mL) |
|---|---|---|
| CA-5-2h-1 | 0.1364 | 0.1358 |
| CA-5-2h-2 | 0.1359 | |
| CA-5-2h-3 | 0.1351 | |

At 3 hours, 5 mL of the clear aqueous solution was taken out from the remaining 34 mL of the aqueous solution. The experiments were done for the 5 mL of the clear aqueous solution taken out at 3 hours using the same protocol as for the 5 mL of the clear aqueous solution taken out at 1 hour. Based on the HPLC data and the measurement data of Example 7, the cabazitaxel concentrations of the solution CA-5-3h have been calculated and shown in the Table 9. At 3 hours, the cabazitaxel concentration of the clear aqueous solution after the filtration was about 98.98% of the cabazitaxel concentration of the clear aqueous solution at 0 hour before the filtration.

TABLE 9

| Solution Number | Cabazitaxel Concentration (mg/mL) | Average Cabazitaxel Concentration (mg/mL) |
|---|---|---|
| CA-5-3h-1 | 0.1353 | 0.1352 |
| CA-5-3h-2 | 0.1353 | |
| CA-5-3h-3 | 0.1349 | |

At 4 hours, 5 mL of the clear aqueous solution was taken out from the remaining 29 mL of the aqueous solution. The experiments were done for the 5 mL of the clear aqueous solution taken out at 4 hours using the same protocol as for the 5 mL of the clear aqueous solution taken out at 1 hour. Based on the HPLC data and the measurement data of Example 7, the cabazitaxel concentrations of the solution CA-5-4h have been calculated and shown in the Table 10. At 4 hours, the cabazitaxel concentration of the clear aqueous solution after the filtration was about 98.76% of the cabazitaxel concentration of the clear aqueous solution at 0 hour before the filtration.

TABLE 10

| Solution Number | Cabazitaxel Concentration (mg/mL) | Average Cabazitaxel Concentration (mg/mL) |
|---|---|---|
| CA-5-4h-1 | 0.1355 | 0.1349 |
| CA-5-4h-2 | 0.1349 | |
| CA-5-4h-3 | 0.1343 | |

At 5 hours, 5 mL of the clear aqueous solution was taken out from the remaining 24 mL of the aqueous solution. The experiments were done for the 5 mL of the clear aqueous solution taken out at 5 hours using the same protocol as for the 5 mL of the clear aqueous solution taken out at 1 hour. Based on the HPLC data and the measurement data of Example 7, the cabazitaxel concentrations of the solution DC-5-5h have been calculated and shown in the Table 11. At 5 hours, the cabazitaxel concentration of the clear aqueous solution after the filtration was about 98.24% of the cabazitaxel concentration of the clear aqueous solution at 0 hour before the filtration.

TABLE 11

| Solution Number | cabazitaxel Concentration (mg/mL) | Average cabazitaxel Concentration (mg/mL) |
|---|---|---|
| CA-5-5h-1 | 0.1347 | 0.1342 |
| CA-5-5h-2 | 0.1341 | |
| CA-5-5h-3 | 0.1337 | |

At 6 hours, 5 mL of the clear aqueous solution was taken out from the remaining 19 mL of the aqueous solution. The experiments were done for the 5 mL of the clear aqueous solution taken out at 6 hours using the same protocol as for the 5 mL of the clear aqueous solution taken out at 1 hour. Based on the HPLC data and the measurement data of Example 7, the cabazitaxel concentrations of the solution CA-5-6h have been calculated and shown in the Table 12. At 6 hours, the cabazitaxel concentration of the clear aqueous solution after the filtration was about 98.46% of the cabazitaxel concentration of the clear aqueous solution at 0 hour before the filtration.

TABLE 12

| Solution Number | cabazitaxel Concentration (mg/mL) | Average cabazitaxel Concentration (mg/mL) |
|---|---|---|
| CA-5-6h-1 | 0.1347 | 0.1345 |
| CA-5-6h-2 | 0.1347 | |
| CA-5-6h-3 | 0.1341 | |

At 24 hours, 5 mL of the clear aqueous solution was taken out from the remaining 14 mL of the aqueous solution. The experiments were done for the 5 mL of the clear aqueous solution taken out at 24 hours using the same protocol as for the 5 mL of the clear aqueous solution taken out at 1 hour. Based on the HPLC data and the measurement data of Example 7, the cabazitaxel concentrations of the solution CA-5-24h have been calculated and shown in the Table 13. At 24 hours, the cabazitaxel concentration of the clear aqueous solution after the filtration was about 98.83% of the cabazitaxel concentration of the clear aqueous solution at 0 hour before the filtration.

TABLE 13

| Solution Number | Cabazitaxel Concentration (mg/mL) | Average Cabazitaxel Concentration (mg/mL) |
|---|---|---|
| CA-5-24h-1 | 0.1353 | 0.1350 |
| CA-5-24h-2 | 0.1352 | |
| CA-5-24h-3 | 0.1345 | |

Example 20

Measure the Cabazitaxel Concentrations in the Clear Aqueous Solutions Before and After the Filtration at 0 Hour, and after the Filtration at 1 Hour, 2 Hours, 3 Hours, 4 Hours, 6 Hours, and 24 Hours 2.25 g of the lyophilized solid of the composition comprising cabazitaxel and HSA (the ratio by weight about 1:300) from Example 15 was dissolved in 45 mL of water to give a clear aqueous solution, which was kept at about 20° C. Immediately after the lyophilized solid was dissolved in water, 6 mL of the clear aqueous solution was taken out from the 45 mL solution. Then 1 mL of the solution was taken out from the 6 mL clear aqueous solution to give the solution CA-0-0h, and the remaining 5 mL of the solution was filtered by the same 0.22 micron aqueous phase filter at 1 mL at a time to give the solutions CA-1-0h, CA-2-0h, CA-3-0h, CA-4-0h, and CA-5-0h. To 200 µl of the solutions CA-0-0h and CA-5-0h were added 800 µl of acetonitrile separately. The mixtures were vortexed for seconds and then centrifuged at 4,000 g for 5 minutes. The supernatants were removed and collected followed by injection on HPLC. The same procedure was repeated 2 more times for each of solutions CA-0-0h and CA-5-0h. Based on the HPLC data and the measurement data of Example 7, the cabazitaxel concentrations of the solutions of CA-0-0h, and CA-5-0h have been calculated and shown in the Table 14. At 0 hour, the cabazitaxel concentration of the clear aqueous solution after the filtration was about 98.75% of the cabazitaxel concentration of the clear aqueous solution before the filtration.

TABLE 14

| Solution Number | Cabazitaxel Concentration (mg/mL) | Average Cabazitaxel Concentration (mg/mL) |
|---|---|---|
| CA-0-0h-1 | 0.1514 | 0.1522 |
| CA-0-0h-2 | 0.1527 | |
| CA-0-0h-3 | 0.1526 | |
| CA-5-0h-1 | 0.1509 | 0.1503 |
| CA-5-0h-2 | 0.1498 | |
| CA-5-0h-3 | 0.1503 | |

At 1 hour, 5 mL of the clear aqueous solution was taken out from the remaining 39 mL of the aqueous solution. Then 1 mL of the solution was taken out from the 5 mL clear aqueous solution and filtered by a 0.22 micron aqueous phase filter to give the solution CA-1-1h, and the remaining 4 mL of the solution was filtered by the same 0.22 micron aqueous phase filter at 1 mL at a time to give the solutions CA-2-1h, CA-3-1h, CA-4-1h, and CA-5-1h. To 200 µl of the solution CA-5-1h was added 800 µl of acetonitrile. The mixture was vortexed for seconds and then centrifuged at 4,000 g for 5 minutes. The supernatant was removed and collected followed by injection on HPLC. The same procedure was repeated 2 more times for the solution CA-5-1h. Based on the HPLC data and the measurement data of Example 7, the cabazitaxel concentrations of the solution CA-5-1h have been calculated and shown in the Table 15. At 1 hour, the cabazitaxel concentration of the clear aqueous solution after the filtration was about 97.77% of the cabazitaxel concentration of the clear aqueous solution at 0 hour before the filtration.

TABLE 15

| Solution Number | Cabazitaxel Concentration (mg/mL) | Average Cabazitaxel Concentration (mg/mL) |
|---|---|---|
| CA-5-1h-1 | 0.1492 | 0.1488 |
| CA-5-1h-2 | 0.1488 | |
| CA-5-1h-3 | 0.1484 | |

At 2 hours, 5 mL of the clear aqueous solution was taken out from the remaining 34 mL of the aqueous solution. The experiments were done for the 5 mL of the clear aqueous solution taken out at 2 hours using the same protocol as for the 5 mL of the clear aqueous solution taken out at 1 hour. Based on the HPLC data and the measurement data of Example 7, the cabazitaxel concentrations of the solution CA-5-2h have been calculated and shown in the Table 16. At 2 hours, the cabazitaxel concentration of the clear aqueous solution after the filtration was about 98.16% of the cabazitaxel concentration of the clear aqueous solution at 0 hour before the filtration.

TABLE 16

| Solution Number | Cabazitaxel Concentration (mg/mL) | Average Cabazitaxel Concentration (mg/mL) |
|---|---|---|
| CA-5-2h-1 | 0.1497 | 0.1494 |
| CA-5-2h-2 | 0.1496 | |
| CA-5-2h-3 | 0.1490 | |

At 3 hours, 5 mL of the clear aqueous solution was taken out from the remaining 29 mL of the aqueous solution. The experiments were done for the 5 mL of the clear aqueous solution taken out at 3 hours using the same protocol as for the 5 mL of the clear aqueous solution taken out at 1 hour. Based on the HPLC data and the measurement data of Example 7, the cabazitaxel concentrations of the solution CA-5-3h have been calculated and shown in the Table 17. At 6 hours, the cabazitaxel concentration of the clear aqueous solution after the filtration was about 98.16% of the cabazitaxel concentration of the clear aqueous solution at 0 hour before the filtration.

TABLE 17

| Solution Number | Cabazitaxel Concentration (mg/mL) | Average Cabazitaxel Concentration (mg/mL) |
|---|---|---|
| CA-5-3h-1 | 0.1496 | 0.1494 |
| CA-5-3h-2 | 0.1497 | |
| CA-5-3h-3 | 0.1490 | |

At 4 hours, 5 mL of the clear aqueous solution was taken out from the remaining 24 mL of the aqueous solution. The experiments were done for the 5 mL of the clear aqueous solution taken out at 4 hours using the same protocol as for the 5 mL of the clear aqueous solution taken out at 1 hour. Based on the HPLC data and the measurement data of Example 7, the cabazitaxel concentrations of the solution CA-5-4h have been calculated and shown in the Table 18. At 4 hours, the cabazitaxel concentration of the clear aqueous solution after the filtration was about 97.63% of the cabazitaxel concentration of the clear aqueous solution at 0 hour before the filtration.

TABLE 18

| Solution Number | Cabazitaxel Concentration (mg/mL) | Average Cabazitaxel Concentration (mg/mL) |
|---|---|---|
| CA-5-4h-1 | 0.1488 | 0.1486 |
| CA-5-4h-2 | 0.1493 | |
| CA-5-4h-3 | 0.1478 | |

At 6 hours, 5 mL of the clear aqueous solution was taken out from the remaining 19 mL of the aqueous solution. The experiments were done for the 5 mL of the clear aqueous solution taken out at 6 hours using the same protocol as for the 5 mL of the clear aqueous solution taken out at 1 hour. Based on the HPLC data and the measurement data of Example 7, the cabazitaxel concentrations of the solution CA-5-6h have been calculated and shown in the Table 19. At 6 hours, the cabazitaxel concentration of the clear aqueous solution after the filtration was about 97.90% of the cabazitaxel concentration of the clear aqueous solution at 0 hour before the filtration.

TABLE 19

| Solution Number | cabazitaxel Concentration (mg/mL) | Average cabazitaxel Concentration (mg/mL) |
|---|---|---|
| CA-5-6h-1 | 0.1490 | 0.1490 |
| CA-5-6h-2 | 0.1493 | |
| CA-5-6h-3 | 0.1488 | |

At 24 hours, 5 mL of the clear aqueous solution was taken out from the remaining 14 mL of the aqueous solution. The experiments were done for the 5 mL of the clear aqueous solution taken out at 24 hours using the same protocol as for the 5 mL of the clear aqueous solution taken out at 1 hour. Based on the HPLC data and the measurement data of Example 7, the cabazitaxel concentrations of the solution CA-5-24h have been calculated and shown in the Table 20. At 24 hours, the cabazitaxel concentration of the clear aqueous solution after the filtration was about 97.63% of the cabazitaxel concentration of the clear aqueous solution at 0 hour before the filtration.

TABLE 20

| Solution Number | Cabazitaxel Concentration (mg/mL) | Average Cabazitaxel Concentration (mg/mL) |
|---|---|---|
| CA-5-24h-1 | 0.1483 | 0.1486 |
| CA-5-24h-2 | 0.1494 | |
| CA-5-24h-3 | 0.1481 | |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for the preparation of a composition comprising cabazitaxel and human serum albumin, wherein the cabazitaxel and the human serum albumin in the composition have a ratio by weight from about 1:100 to about 1:1000, said method comprising:
    (i) obtaining an organic solution of cabazitaxel in a polar water-miscible organic solvent;
    (ii) obtaining a first aqueous solution of human serum albumin; and
    (iii) adding the organic solution of cabazitaxel to the first aqueous solution of human serum albumin to obtain a second aqueous solution comprising the composition comprising cabazitaxel and human serum albumin, wherein the second aqueous solution is a clear aqueous solution with no precipitation of cabazitaxel, and the addition is done at ambient temperature.

2. The method of claim 1, wherein the ambient temperature is room temperature.

3. The method of claim 1, wherein the polar water-miscible organic solvent is an alcohol.

4. The method of claim 1, wherein the polar water-miscible organic solvent is ethanol.

5. The method of claim 1, wherein the solvents of the second aqueous solution are further removed to provide a solid by lyophilization.

6. The method of claim 1, wherein the range of pH in the second aqueous solution is from about 4 to about 8.

7. The method of claim 1, wherein the human serum albumin is a native human serum albumin.

8. The method of claim 1, wherein the human serum albumin is a recombinant human serum albumin.

* * * * *